United States Patent
Andreassi, II et al.

(10) Patent No.: US 8,921,360 B2
(45) Date of Patent: Dec. 30, 2014

(54) HETEROBICYCLE-SUBSTITUTED AZOLYL BENZENE FUNGICIDES

(76) Inventors: John Lawrence Andreassi, II, Wilmington, DE (US); Andrew Edmund Taggi, Newark, DE (US)

( * ) Notice: Subject to any disclaimer, the term of this patent is extended or adjusted under 35 U.S.C. 154(b) by 107 days.

(21) Appl. No.: 13/500,928

(22) PCT Filed: Oct. 12, 2010

(86) PCT No.: PCT/US2010/052228
§ 371 (c)(1),
(2), (4) Date: Apr. 9, 2012

(87) PCT Pub. No.: WO2011/059619
PCT Pub. Date: May 19, 2011

(65) Prior Publication Data
US 2012/0202815 A1    Aug. 9, 2012

Related U.S. Application Data

(60) Provisional application No. 61/255,996, filed on Oct. 29, 2009.

(51) Int. Cl.
| | |
|---|---|
| *A01N 43/50* | (2006.01) |
| *A01N 43/647* | (2006.01) |
| *A01N 43/32* | (2006.01) |
| *C07D 265/36* | (2006.01) |
| *C07D 231/02* | (2006.01) |
| *C07D 405/04* | (2006.01) |
| *A01N 43/56* | (2006.01) |
| *A01N 47/18* | (2006.01) |
| *A01N 47/28* | (2006.01) |

(52) U.S. Cl.
CPC ............. *C07D 405/04* (2013.01); *A01N 43/56* (2013.01); *A01N 47/18* (2013.01); *A01N 47/28* (2013.01)
USPC ........ 514/230.5; 514/249; 514/359; 514/434; 514/406; 544/105; 548/364.4

(58) Field of Classification Search
None
See application file for complete search history.

(56) References Cited

U.S. PATENT DOCUMENTS

2010/0120714 A1    5/2010    Finkelstein et al.

FOREIGN PATENT DOCUMENTS

| WO | 2005/051932 A1 | 6/2005 |
|---|---|---|
| WO | 2008/124092 A2 | 10/2008 |

*Primary Examiner* — Savitha Rao
*Assistant Examiner* — Gregg Polansky
(74) *Attorney, Agent, or Firm* — Renee M. Lett

(57) ABSTRACT

Disclosed are compounds of Formula 1, including all stereoisomers, N-oxides, and salts thereof,

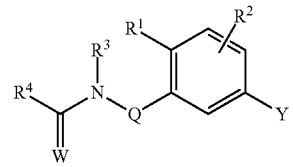

wherein Y is a 5-membered, fully or partially unsaturated heterocyclic ring containing 2-4 carbon atoms and 2-3 nitrogen atoms as ring members, the ring substituted with Z on a ring member atom connected through an adjacent single ring member atom to the ring member atom attaching the heterocyclic ring to the phenyl ring of Formula 1, and optionally further substituted with up to 2 substituents independently selected from $R^5$ on carbon atom ring members and from $R^6$ on nitrogen atom ring members;

Z is an 8-, 9-, 10- or 11-membered fused heterobicyclic ring system containing ring members selected from carbon atoms and 1 to 4 heteroatoms independently selected from up to 2 O, up to 2 S and up to 4 N atoms, wherein up to 3 carbon atom ring members are independently selected from C(=O) and C(=S), and the sulfur atom ring members are independently selected from $S(=O)_u(=NR^7)_z$, the ring system optionally substituted with substituents independently selected from $R^8$ on carbon atom ring members and from $R^9$ on nitrogen atom ring members;

and $R^1$, $R^2$, $R^3$, $R^4$, $R^5$, $R^6$, $R^7$, $R^8$, $R^9$, u and z are as defined in the disclosure.

Also disclosed are compositions containing the compounds of Formula 1 and methods for controlling plant disease caused by a fungal pathogen comprising applying an effective amount of a compound or a composition of the invention.

10 Claims, No Drawings

HETEROBICYCLE-SUBSTITUTED AZOLYL BENZENE FUNGICIDES

FIELD OF THE INVENTION

This invention relates to certain heterobicycle-substituted azolyl benzene compounds, their N-oxides, salts and compositions, and methods of their use as fungicides.

BACKGROUND OF THE INVENTION

The control of plant diseases caused by fungal plant pathogens is extremely important in achieving high crop efficiency. Plant disease damage to ornamental, vegetable, field, cereal, and fruit crops can cause significant reduction in productivity and thereby result in increased costs to the consumer. Many products are commercially available for these purposes, but the need continues for new compounds that are more effective, less costly, less toxic, environmentally safer or have different sites of action.

PCT Patent Publication WO2008/124092 discloses fungicidal compounds of Formula i

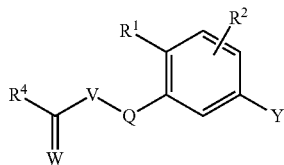

i wherein Y is, inter alia, selected from twenty-four 5- or 6-membered heteroaromatic rings optionally substituted with a phenyl ring or a 5- or 6-membered heteroaromatic ring. The heterobicycle-substituted azolyl benzene compounds of the present invention are not disclosed in this publication.

SUMMARY OF THE INVENTION

This invention is directed to compounds of Formula 1 (including all stereoisomers), N-oxides, and salts thereof, agricultural compositions containing them and their use as fungicides:

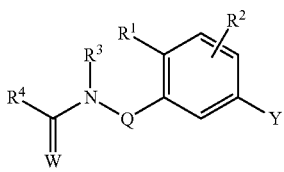

1 wherein
Y is a 5-membered, fully or partially unsaturated heterocyclic ring containing 2-4 carbon atoms and 2-3 nitrogen atoms as ring members, the ring substituted with Z on a ring member atom connected through an adjacent single ring member atom to the ring member atom attaching the heterocyclic ring to the phenyl ring of Formula 1, and optionally further substituted with up to 2 substituents independently selected from $R^5$ on carbon atom ring members and from $R^6$ on nitrogen atom ring members;
Z is an 8-, 9-, 10- or 11-membered fused heterobicyclic ring system containing ring members selected from carbon atoms and 1 to 4 heteroatoms independently selected from up to 2 O, up to 2 S and up to 4 N atoms, wherein up to 3 carbon atom ring members are independently selected from C(=O) and C(=S), and the sulfur atom ring members are independently selected from $S(=O)_t(=NR^7)_z$, the ring system optionally substituted with substituents independently selected from $R^8$ on carbon atom ring members and from $R^9$ on nitrogen atom ring members;
W is O or S;
Q is $CR^{10a}R^{10b}$, O or $NR^{11}$;
$R^1$ is halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_6$ cycloalkyl;
$R^2$ is H, halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_6$ cycloalkyl;
$R^3$ is H, $C_1$-$C_3$ alkyl, $C_1$-$C_3$ haloalkyl, $C_3$-$C_4$ cycloalkyl, $C_3$-$C_4$ halocycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;
$R^4$ is H, hydroxy, amino, $C_1$-$C_3$ alkyl, $C_1$-$C_4$ haloalkyl, $C_3$-$C_4$ cycloalkyl, $C_3$-$C_4$ halocycloalkyl, $C_1$-$C_4$ alkoxy, $C_1$-$C_4$ haloalkoxy, $C_3$-$C_4$ cycloalkoxy, $C_1$-$C_4$ alkylamino, $C_1$-$C_4$ haloalkylamino, $C_2$-$C_6$ dialkylamino, $C_2$-$C_6$ halodialkylamino or $C_3$-$C_4$ cycloalkylamino;
each $R^5$ is independently halogen, cyano, hydroxy, amino, nitro, $C_1$-$C_6$ alkyl, $C_3$-$C_5$ cycloalkyl, $C_3$-$C_5$ halocycloalkyl, $C_2$-$C_6$ alkenyl, $C_2$-$C_6$ alkynyl or $C_1$-$C_6$ haloalkyl;
each $R^6$ is independently cyano, hydroxy, $C_1$-$C_6$ alkyl, $C_1$-$C_6$ haloalkyl, $C_3$-$C_5$ cycloalkyl, $C_3$-$C_5$ halocycloalkyl, $C_2$-$C_6$ alkenyl or $C_3$-$C_6$ alkynyl;
each $R^8$ is independently halogen, cyano, hydroxy, amino, nitro, —CH(=O), —C(=O)OH, —C(=O)NH$_2$, —C($R^{12}$)=N—O—$R^{13}$, —C($R^{12}$)=N—$R^{13}$, $C_1$-$C_4$ alkyl, $C_1$-$C_4$ haloalkyl, $C_3$-$C_4$ cycloalkyl, $C_2$-$C_4$ alkenyl, $C_2$-$C_4$ alkynyl, $C_2$-$C_5$ alkylcarbonyl, $C_2$-$C_5$ haloalkylcarbonyl, $C_4$-$C_5$ cycloalkylcarbonyl, $C_2$-$C_5$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_5$ cycloalkylaminocarbonyl, $C_1$-$C_4$ alkoxy, $C_1$-$C_4$ haloalkoxy, $C_3$-$C_4$ cycloalkoxy, $C_3$-$C_4$ halocycloalkoxy, $C_4$-$C_5$ cycloalkylalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_4$ alkylthio, $C_1$-$C_4$ haloalkylthio, $C_3$-$C_6$ cycloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_3$-$C_5$ cycloalkylsulfonyl, $C_3$-$C_7$ trialkylsilyl, $C_1$-$C_4$ alkylamino, $C_2$-$C_8$ dialkylamino, $C_1$-$C_4$ haloalkylamino, $C_2$-$C_8$ halodialkylamino, $C_3$-$C_6$ cycloalkylamino, $C_2$-$C_5$ alkylcarbonylamino or $C_2$-$C_5$ haloalkylcarbonylamino;
each $R^9$ is independently cyano, hydroxy, —CH(=O), —C(=O)NH$_2$, —C($R^{12}$)=N—O—$R^{13}$, —C($R^{12}$)=N—$R^{13}$, $C_1$-$C_4$ alkyl, $C_3$-$C_4$ cycloalkyl, $C_2$-$C_4$ alkenyl, $C_2$-$C_4$ alkynyl, $C_1$-$C_4$ haloalkyl, $C_2$-$C_5$ alkylcarbonyl, $C_2$-$C_5$ haloalkylcarbonyl, $C_4$-$C_5$ cycloalkylcarbonyl, $C_2$-$C_5$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_5$ cycloalkylaminocarbonyl, $C_1$-$C_4$ alkoxy, $C_1$-$C_4$ haloalkoxy, $C_3$-$C_4$ cycloalkoxy, $C_3$-$C_4$ halocycloalkoxy, $C_4$-$C_5$ cycloalkylalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_2$-$C_8$ alkylcarbonyloxy, $C_2$-$C_8$ haloalkylcarbonyloxy, $C_4$-$C_{10}$ cycloalkylcarbonyloxy, $C_1$-$C_6$ alkylthio, benzylthio, $C_1$-$C_6$ haloalkylthio, $C_3$-$C_8$ cycloalkylthio, $C_1$-$C_4$ alkylsulfonyl, $C_1$-$C_4$ haloalkylsulfonyl, $C_3$-$C_6$ cycloalkylsulfonyl or $C_3$-$C_{10}$ trialkylsilyl;

each $R^7$ and $R^{13}$ is independently H, $C_1$-$C_3$ alkyl, $C_1$-$C_3$ haloalkyl, $C_2$-$C_3$ alkylcarbonyl or $C_2$-$C_3$ haloalkylcarbonyl;

$R^{10a}$ is H, OH, halogen, cyano, $C_1$-$C_3$ alkyl, $C_1$-$C_3$ haloalkyl, $C_2$-$C_3$ alkoxyalkyl, $C_1$-$C_3$ alkoxy, $C_1$-$C_3$ haloalkoxy or $C_1$-$C_3$ alkylsulfonyl;

$R^{10b}$ is H, $C_1$-$C_3$ alkyl, $C_1$-$C_3$ haloalkyl, $C_2$-$C_3$ alkoxyalkyl, $C_1$-$C_3$ alkoxy or $C_1$-$C_3$ haloalkoxy; or $R^{10a}$ and $R^{10b}$ are taken together with the carbon atom to which they are attached to form a $C_3$-$C_4$ cycloalkyl or $C_3$-$C_4$ halocycloalkyl ring;

$R^{11}$ is H, $C_1$-$C_3$ alkyl, $C_1$-$C_3$ haloalkyl, $C_2$-$C_3$ alkylcarbonyl or $C_2$-$C_3$ haloalkylcarbonyl;

each $R^{12}$ is independently H, $C_1$-$C_3$ alkyl, $C_3$-$C_5$ cycloalkyl or $C_1$-$C_3$ haloalkyl; and u and z in each instance of $S(=O)_u(=NR^7)_z$ are independently 0, 1 or 2, provided that the sum of u and z in each instance of $S(=O)_u(=NR^7)_z$ is 0, 1 or 2.

More particularly, this invention relates to a compound of Formula 1 (including all stereoisomers), an N-oxide, or a salt thereof.

This invention also relates to a fungicidal composition comprising (a) a compound of the invention (i.e. in a fungicidally effective amount); and (b) at least one additional component selected from the group consisting of surfactants, solid diluents and liquid diluents.

This invention also relates to a fungicidal composition comprising (a) a compound of the invention and (b) at least one other fungicide (e.g., at least one other fungicide having the same or different site of action).

This invention further relates to a method for controlling plant diseases caused by fungal plant pathogens comprising applying to the plant or portion thereof, or to the plant seed, a fungicidally effective amount of a compound of the invention (e.g., as a composition described herein).

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, a mixture, process, or method that comprises a list of elements is not necessarily limited to only those elements but may include other elements not expressly listed or inherent to such composition, mixture, process, or method.

The transitional phrase "consisting of" excludes any element, step, or ingredient not specified. If in the claim, such would close the claim to the inclusion of materials other than those recited except for impurities ordinarily associated therewith. When the phrase "consists of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkoxyalkoxy" denotes alkoxy substitution on alkoxy. "Alkenyloxy" includes straight-chain or branched alkenyloxy moieties. Examples of "alkenyloxy" include $H_2C=CHCH_2O$, $(CH_3)_2C=CHCH_2O$, $(CH_3)CH=CHCH_2O$, $(CH_3)CH=C(CH_3)CH_2O$ and $CH_2=CHCH_2CH_2O$. "Alkynyloxy" includes straight-chain or branched alkynyloxy moieties. Examples of "alkynyloxy" include $HC\equiv CCH_2O$, $CH_3C\equiv CCH_2O$ and $CH_3C\equiv CCH_2CH_2O$. "Alkylthio" includes branched or straight-chain alkylthio moieties such as methylthio, ethylthio, and the different propylthio, butylthio, pentylthio and hexylthio isomers. "Alkylsulfinyl" includes both enantiomers of an alkylsulfinyl group. Examples of "alkylsulfinyl" include $CH_3S(O)—$, $CH_3CH_2S(O)—$, $CH_3CH_2CH_2S(O)—$, $(CH_3)_2CHS(O)—$ and the different butylsulfonyl, pentylsulfinyl and hexylsulfinyl isomers. Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopropylmethyl and cyclobutylmethyl. The term "cycloalkoxy" denotes cycloalkyl linked through an oxygen atom such as cyclopentyloxy and cyclohexyloxy. "Cycloalkylalkoxy" denotes cycloalkylalkyl linked through an oxygen atom attached to the alkyl chain. Examples of "cycloalkylalkoxy" include cyclopropylmethoxy, cyclopropylethoxy and cyclobutylmethoxy.

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when used in descriptions such as "alkyl substituted with halogen" said alkyl may be partially or fully substituted with halogen atoms which may be the same or different. Examples of "haloalkyl" or "alkyl substituted with halogen" include $F_3C$—, $ClCH_2$—, $CF_3CH_2$— and $CF_3CCl_2$—. The terms "halocycloalkyl", "haloalkoxy", "haloalkylthio", "haloalkenyl", "haloalkynyl", and the like, are defined analogously to the term "haloalkyl". Examples of "haloalkoxy" include $CF_3O$—, $CCl_3CH_2O$—, $HCF_2CH_2CH_2O$— and $CF_3CH_2O$—. Examples of "haloalkylthio" include $CCl_3S$—, $CF_3S$—, $CCl_3CH_2S$— and $ClCH_2CH_2CH_2S$—. Examples of "haloalkylsulfinyl" include $CF_3S(O)$—, $CCl_3S(O)$—, $CF_3CH_2S(O)$— and $CF_3CF_2S(O)$—. Examples of "haloalkylsulfonyl" include $CF_3S(O)_2$—, $CCl_3S(O)_2$—, $CF_3CH_2S(O)_2$— and $CF_3CF_2S(O)_2$—. Examples of "haloalkenyl" include $(Cl)_2C=CHCH_2$— and $CF_3CH_2CH=CHCH_2$—. Examples of "haloalkynyl" include $HC\equiv CCHCl$—, $CF_3C\equiv C$—, $CCl_3C\equiv C$— and $FCH_2C\equiv CCH_2$—.

"Alkylcarbonyl" denotes a straight-chain or branched alkyl moieties bonded to a $C(=O)$ moiety. Examples of "alkylcarbonyl" include $CH_3C(=O)$—, $CH_3CH_2CH_2C(=O)$— and $(CH_3)_2CHC(=O)$—. Examples of "haloalkylcarbonyl" include $CF_3C(=O)$—, $CH_3CCl_2C(=O)$—, $CCl_3CH_2CH_2C(=O)$— and $CF_3CF_2C(=O)$—. Examples of "alkoxycarbonyl" include $CH_3C(=O)$—, $CH_3CH_2OC(=O)$—, $CH_3CH_2CH_2C(=O)$—, $(CH_3)_2CHOC(=O)$— and the different butoxy- or pentoxycarbonyl isomers. Examples of "alkylaminocarbonyl" include $CH_3NHC(=O)$—, $CH_3CH_2NHC(=O)$—, $CH_3CH_2CH_2NHC(=O)$—, $(CH_3)_2CHNHC(=O)$— and the different butylamino- or pentylaminocarbonyl isomers. Examples of "dialkylaminocarbonyl" include $(CH_3)_2NC(=O)$—, $(CH_3CH_2)_2NC(=O)$—, $CH_3CH_2(CH_3)NC(=O)$—, $(CH_3)_2CHN(CH_3)C(=O)$— and $CH_3CH_2CH_2(CH_3)NC(=O)$—.

"Alkylamino includes an NH radical substituted with straight-chain or branched alkyl. Examples of "alkylamino" include $CH_3CH_2NH$—, $CH_3CH_2CH_2NH$—, and $(CH_3)_2CHCH_2NH$—. Examples of "dialkylamino" include $(CH_3)_2N$—, $(CH_3CH_2CH_2)_2N$— and $CH_3CH_2(CH_3)N$—. The term "haloalkylamino" denotes at least one halogen group substituted on the alkyl moiety of the alkylamino group. Examples of "haloalkylamino" include $CH_2ClCH_2NH$— and $(CF_3)_2CHNH$— "Halodialkylamino" denotes at least one halogen group substituted on any alkyl moiety of the dialkylamino group. Examples of "halodialkylamino" include $CF_3(CH_3)N$—, $(CF_3)_2N$— and $CH_2Cl(CH_3)N$—. "Cycloalkylamino" means the amino nitrogen atom is attached to a cycloalkyl radical and a hydrogen atom. Examples of "cycloalkylamino" include cyclopropylamino, cyclobutylamino, cyclopentylamino and cyclohexylamino. "Alkylcarbonylamino" means the amino nitrogen atom is attached to a straight-chain or branched alkylcarbonyl group and a hydrogen atom. Examples of "alkylcarbonylamino" include $CH_3C(=O)NH$—, $CH_3CH_2C(=O)NH$—, $CH_3CH_2CH_2C(=O)NH$— and $(CH_3)_2CHC(=O)NH$—. The term "haloalkylcarbonylamino" denotes at least one halogen substituted on the alkyl moiety of the alkylcarbonylamino group. Examples of "haloalkylcarbonylamino" include $CH_2ClCH_2C(=O)NH$—, $(CH_3)_2CClC(=O)NH$— and $CH_2ClC(=O)NH$—. "Alkylsulfonylamino" and "haloalkylsulfonylamino" are defined analogously to the term "alkylcarbonylamino".

"Trialkylsilyl" includes 3 branched and/or straight-chain alkyl radicals attached to and linked through a silicon atom, such as trimethylsilyl, triethylsilyl and tert-butyldimethylsilyl.

The total number of carbon atoms in a substituent group is indicated by the "$C_i$-$C_j$" prefix where i and j are numbers from 1 to 10. For example, $C_1$-$C_4$ alkylsulfonyl designates methylsulfonyl through butylsulfonyl; $C_2$ alkoxyalkyl designates $CH_3OCH_2$—; $C_3$ alkoxyalkyl designates, for example, $CH_3CH(OCH_3)$—, $CH_3OCH_2CH_2$— or $CH_3CH_2OCH_2$—; and $C_4$ alkoxyalkyl designates the various isomers of an alkyl group substituted with an alkoxy group containing a total of four carbon atoms, examples including $CH_3CH_2CH_2OCH_2$— and $CH_3CH_2OCH_2CH_2$—.

When a compound is substituted with a substituent bearing a subscript that indicates the number of said substituents can exceed 1, said substituents (when they exceed 1) are independently selected from the group of defined substituents, e.g., $(R^5)_m$ in Y-1 of Exhibit 1 wherein m is 0, 1 or 2. When a group contains a substituent which can be hydrogen, for example $R^2$, then when this substituent is taken as hydrogen, it is recognized that this is equivalent to said group being unsubstituted. When one or more positions on a group are said to be "not substituted" or "unsubstituted", then hydrogen atoms are attached to take up any free valency.

As used herein, the following definitions shall apply unless otherwise indicated. The term "optionally substituted" is used interchangeably with the phrase "substituted or unsubstituted". Unless otherwise indicated, an optionally substituted group may be unsubstituted or be substituted at one or more positions, limited by the number of available positions, and furthermore each substitution is independent of the others. Therefore unless a limit is stated, an optionally substituted group may have a substituent at each substitutable position of the group.

Unless otherwise indicated, a "ring" or "ring system" as a component of Formula 1 is carbocyclic or heterocyclic. The ring of substituent Y and the ring system of substituent Z are both heterocyclic. The term "ring system" denotes two or more fused rings. The terms "bicyclic ring system" and "fused bicyclic ring system" denote a ring system consisting of two fused rings, in which either ring can be saturated, partially unsaturated, or fully unsaturated unless otherwise indicated. The term "fused heterobicyclic ring system" denotes a fused bicyclic ring system in which at least one ring atom is not carbon. The term "ring member" refers to an atom or other moiety (e.g., $C(=O)$, $C(=S)$, $S(O)$ or $S(O)_2$) forming the backbone of a ring or ring system. A ring or ring system may be attached to the remainder of Formula 1 through any available carbon or nitrogen ring atom, unless otherwise described.

The term "saturated" in reference to a ring or ring system means that the ring members of the ring or ring system are connected together by only single bonds. The term "unsaturated" means that the ring or ring system has at least two carbon and/or nitrogen atom ring members connected by a double bond. The term "partially unsaturated" (synonymous with "partially saturated") means that the unsubstituted ring or ring system has at least two carbon and/or nitrogen atom ring members connected by a double bond and also has at least two carbon and/or nitrogen atom ring members connected by a single bond from which hydrogen atoms could be conceptually removed to form a double bond without also forming a cumulated double bond moiety. The term "fully unsaturated" means that the unsubstituted ring or ring system has at least two carbon and/or nitrogen atom ring members connected by a double bond and that hydrogen atoms cannot be removed from any of the carbon and/or nitrogen atom ring members connected by a single bond without creating a cumulated double bond moiety. Therefore the term "partially or fully unsaturated" is synonymous with simply "unsaturated".

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Hückel's rule, then said ring is also called an "aromatic ring".

The terms "heterocyclic ring", "heterocycle" or "heterocyclic ring system" generally denote a ring or ring system in which at least one atom forming the ring backbone is not carbon, e.g., nitrogen, oxygen or sulfur. Typically a heterocyclic ring or ring system contains no more than 4 nitrogens, no more than 2 oxygens and no more than 2 sulfurs. A heterocyclic ring or ring system may be further defined; for example the heterocyclic ring of substituent Y of Formula 1 contains only carbon and nitrogen atoms as ring members. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring" or "aromatic heterocyclic ring". Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a p-orbital perpendicular to the ring plane, and that (4n+2) π electrons, where n is a positive integer, are associated with the ring to comply with Hückel's rule. The term "aromatic ring system" denotes a carbocyclic or heterocyclic ring system in which at least one ring of the ring system is aromatic.

The Y ring in Formula 1 is defined in the Summary of the Invention as:

Y is a 5-membered, fully or partially unsaturated heterocyclic ring containing 2-4 carbon atoms and 2-3 nitrogen atoms as ring members, the ring substituted with Z on a ring member atom connected through an adjacent single ring member atom to the ring member atom attaching the heterocyclic ring to the phenyl ring of Formula 1, . . . .

This definition is meant to specify that the Z ring is connected to the Y ring two atoms away from the location of the benzene ring connection to the Y ring as shown in the diagram below.

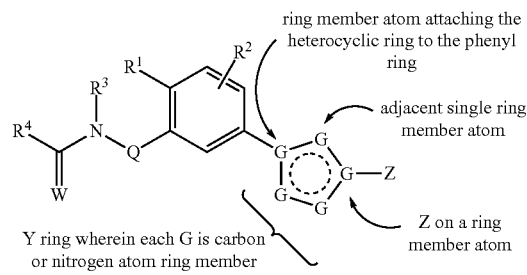

Exhibit 1 below illustrates 5-membered, fully or partially unsaturated heterocyclic rings relevant to substituent Y of Formula 1. Exhibits 2A and 2B below illustrate fused heterobicyclic ring systems relevant to substituent Z of Formula 1. The substituents $R^{8a}$ and $R^{8b}$ on heterobicyclic ring systems in Exhibit 2B are defined as $R^8$ wherein the substituent $R^{8a}$ is on the ring directly attached to the rest of Formula 1 (first ring of the heterobicyclic ring system) and $R^{8b}$ is on the terminal ring (second ring of the heterobicyclic ring system).

A wide variety of synthetic methods are known in the art to enable preparation of aromatic and nonaromatic heterocyclic rings and ring systems; for extensive reviews see the eight volume set of *Comprehensive Heterocyclic Chemistry*, A. R. Katritzky and C. W. Rees editors-in-chief, Pergamon Press, Oxford, 1984 and the twelve volume set of *Comprehensive Heterocyclic Chemistry II*, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

One skilled in the art will appreciate that not all nitrogen-containing heterocycles can form N-oxides since the nitrogen requires an available lone pair for oxidation to the oxide; one skilled in the art will recognize those nitrogen containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in*

*Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding non-salt forms, salts share the biological utility of the nonsalt forms. Thus a wide variety of salts of the compounds of Formula 1 are useful for control of plant diseases caused by fungal plant pathogens (i.e. are agriculturally suitable). When a compound of Formula 1 contains a basic moiety such as an amino substituent or a nitrogen atom ring member, salts of the compound include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of Formula 1 contains an acidic moiety such as a carboxylic acid or phenol, salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from Formula 1, N-oxides, and agriculturally suitable salts thereof.

Compounds selected from Formula 1, stereoisomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

Embodiments of the present invention as described in the Summary of the Invention include those described below. In the following Embodiments, Formula 1 includes N-oxides and salts thereof, and reference to "a compound of Formula 1" includes the definitions of the substituents specified in the Summary of the Invention unless further defined in the Embodiments.

Embodiment 1

A compound of Formula 1 wherein Y is a 5-membered heterocycle selected from Y-1 through Y-25 as shown in Exhibit 1

Exhibit 1

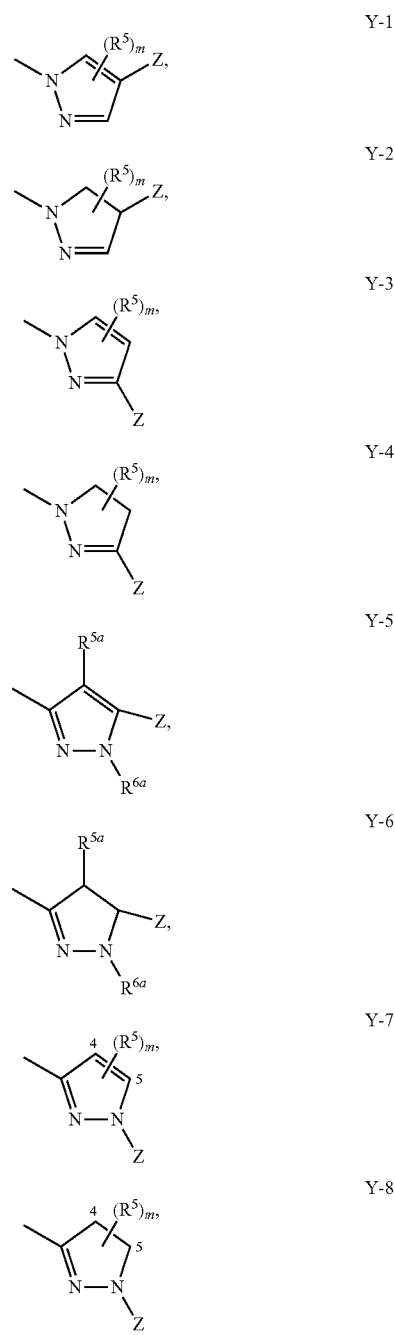

-continued
Y-9 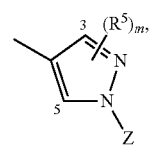
Y-10 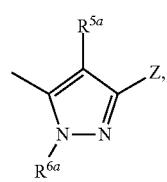
Y-11 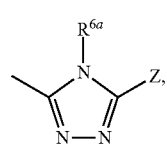
Y-12 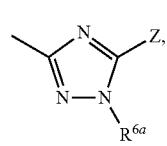
Y-13 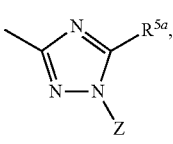
Y-14 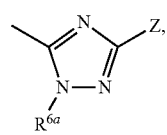
Y-15 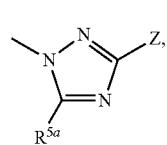
Y-16 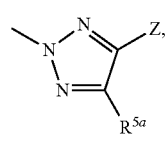
Y-17 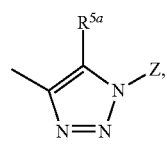
Y-18 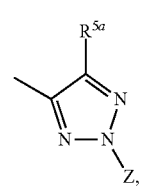
-continued
Y-19 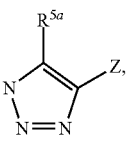
Y-20 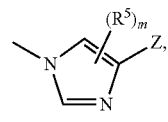
Y-21 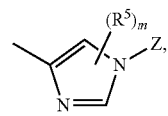
Y-22 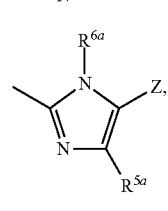
Y-23 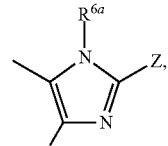
Y-24 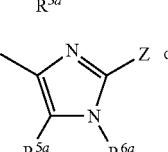
Y-25 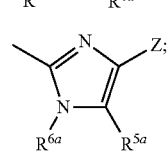
wherein
R$^{5a}$ is H or R$^5$;
R$^{6a}$ is H or R$^6$; and
m is 0, 1 or 2.
Embodiment 2
A compound of Embodiment 1 wherein Y is Y-1, Y-2, Y-3, Y-4, Y-5, Y-6, Y-7, Y-8, Y-13, Y-14, Y-15, Y-16, Y-18 or Y-25.
Embodiment 3
A compound of Embodiment 2 wherein Y is Y-1, Y-3, Y-4, Y-5, Y-7, Y-8, Y-13, Y-14, Y-15, Y-18 or Y-25.
Embodiment 4
A compound of Embodiment 3 wherein Y is Y-1, Y-3, Y-4, Y-5, Y-7, Y-8 or Y-25.

Embodiment 5

A compound of Embodiment 4 wherein Y is Y-3, Y-4, Y-7 or Y-8.

Embodiment 6

A compound of Formula 1 or any one of Embodiments 1 through 5 wherein each $R^5$ is independently halogen, cyano, $C_1$-$C_2$ alkyl or $C_1$-$C_2$ haloalkyl.

Embodiment 7

A compound of Embodiment 6 wherein each $R^5$ is independently halogen or methyl.

Embodiment 8

A compound of Formula 1 or any one of Embodiments 1 through 7 wherein each $R^6$ is independently $C_1$-$C_2$ alkyl or $C_1$-$C_2$ haloalkyl.

Embodiment 9

A compound of Embodiment 8 wherein each $R^6$ is independently methyl or trifluoromethyl.

Embodiment 10

A compound of Embodiment 9 wherein each $R^6$ is methyl.

Embodiment 11

A compound of Formula 1 or any one of Embodiments 1 through 5 wherein the heterocyclic ring of Y is unsubstituted (i.e. $R^{5a}$ and $R^{6a}$ are H and m is 0).

Embodiment 12

A compound of Formula 1 or any one of Embodiments 1 through 11 wherein the fused heterobicyclic ring system of Z is optionally substituted with up to 6 substituents independently selected from $R^8$ on carbon atom ring members and from $R^9$ on nitrogen atom ring members.

Embodiment 13

A compound of Formula 1 or any one of Embodiments 1 through 12 wherein in the fused heterobicyclic ring system of Z the ring that is directly bonded to Y is identified as a first ring, and the ring that is fused to the first ring is identified as a second ring.

Embodiment 14

A compound of Embodiment 13 wherein in the heterocyclic ring system of Z the second ring includes an O atom as a ring member directly bonded to a ring fusion atom shared with the first ring.

Embodiment 15

A compound of Embodiment 14 wherein said ring fusion atom (directly bonded to the O atom ring member in the second ring) is connected through no less than one intervening ring member atom (in the first ring) to the ring member atom (in the first ring) directly bonded to Y.

Embodiment 16

A compound of any one of Embodiments 14 through 15 wherein when in the heterocyclic ring system of Z the first ring is 6-membered, then said ring fusion atom (directly bonded to the O atom ring member) is para (i.e. 1,4 relationship) to the bond of Z to Y.

Embodiment 17

A compound of any one of Embodiments 13 through 16 wherein in the heterocyclic ring system of Z when the second ring contains 5 or fewer ring members then none of the ring members of the second ring not shared with the first ring are bonded to an adjacent ring member through a double bond, and when the second ring contains 6 or more ring members then at most two atom ring members of the second ring not shared with the first ring are bonded together through a double bond.

Embodiment 18

A compound of any one of Embodiments 13 through 17 wherein the first ring in the heterobicyclic ring system of Z is fully unsaturated.

Embodiment 19

A compound of Embodiment 18 wherein the first ring in the heterobicyclic ring system of Z is aromatic (including heteroaromatic).

Embodiment 20

A compound of Embodiment 19 wherein the first ring in the heterobicyclic ring system of Z is selected from phenyl, pyridinyl, pyridazinyl, pyrimidinyl, pyrazolyl and thiazolyl rings, each optionally substituted with up to 2 substituents independently selected from $R^8$ on carbon atom ring members and from $R^9$ on nitrogen atom ring members (in addition to the fusion of the second ring to the first ring).

Embodiment 21

A compound of Embodiment 20 wherein the first ring in the heterobicyclic ring system of Z is selected from phenyl and pyridinyl rings, each optionally substituted with up to 2 substituents independently selected from $R^8$ on carbon atom ring members and from $R^9$ on nitrogen atom ring members.

Embodiment 22

A compound of Embodiment 21 wherein the first ring in the heterobicyclic ring system of Z is a phenyl ring optionally substituted with up to 2 substituents independently selected from $R^8$ on carbon atom ring members and from $R^9$ on nitrogen atom ring members.

Embodiment 23

A compound of Formula 1 or any one of Embodiments 1 through 20 wherein Z is selected from Z-A through Z-F as shown in Exhibit 2A Exhibit 2A

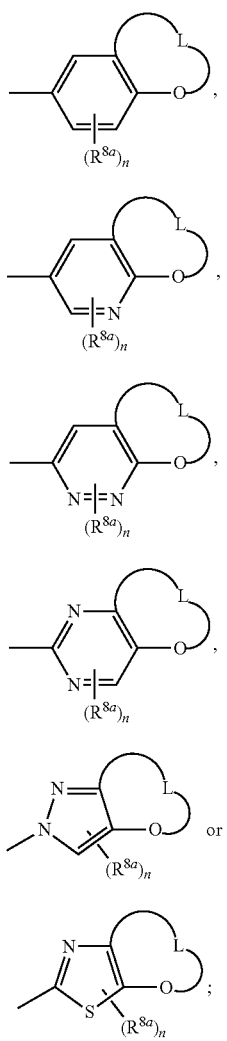

L is a linking chain containing 2-4 chain members selected from carbon atoms and up to 2 heteroatoms independently selected from up to 2 O, up to 1 S and up to 1 N atoms, wherein up to 2 carbon atom ring members are independently selected from C(=O) and C(=S), and the sulfur atom ring members are independently selected from $S(=O)_u(=NR^7)_z$, the linking chain optionally substituted with up to 4 substituents independently selected from $R^{8b}$ on carbon atom ring members and from $R^9$ on nitrogen atom ring members;

each $R^{8a}$ (depicted optionally bonded to the left (first) ring of the bicyclic ring system) and $R^{8b}$ is independently $R^8$; and n is 0, 1 or 2 (limited by the number of available bonding positions).

Embodiment 24

A compound of Embodiment 23 wherein L is a linking chain containing 2-4 chain members selected from carbon atoms and up to 1 oxygen atom, wherein up to 1 carbon atom ring member is selected from C(=O), the linking chain optionally substituted with up to 2 substituents independently selected from $R^{8b}$.

Embodiment 25

A compound of Embodiment 24 wherein Z is selected from Z-1 through Z-31 as shown in Exhibit 2B Exhibit 2B

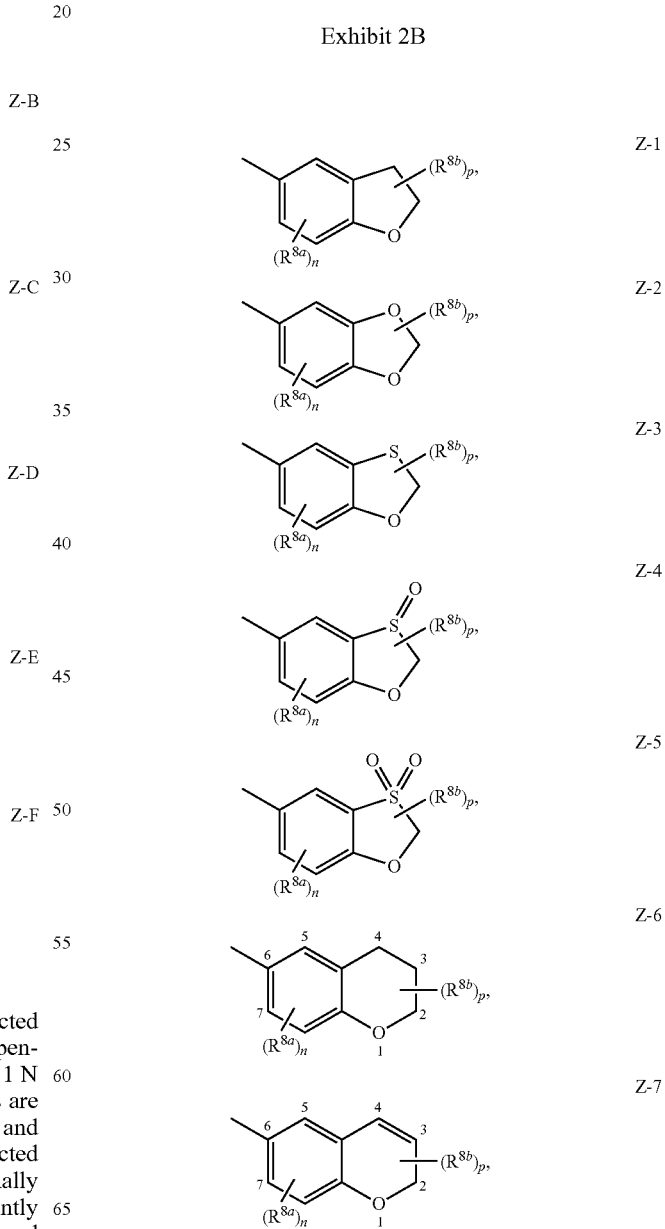

-continued
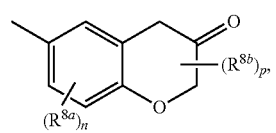
Z-8
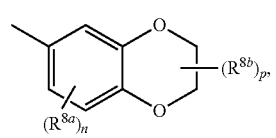
Z-9
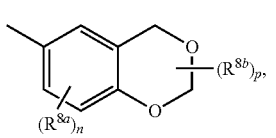
Z-10
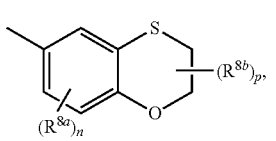
Z-11
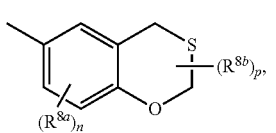
Z-12
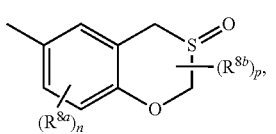
Z-13
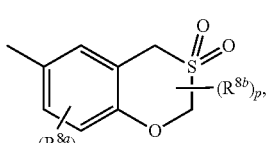
Z-14
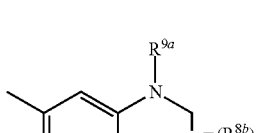
Z-15
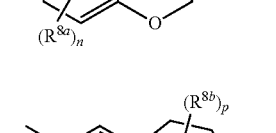
Z-16
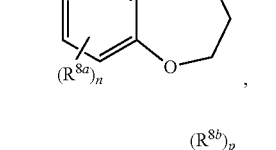
Z-17
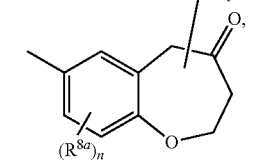
-continued
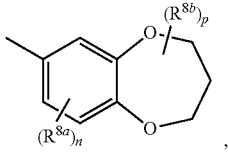
Z-18
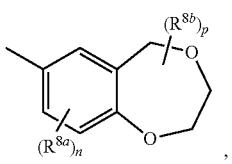
Z-19
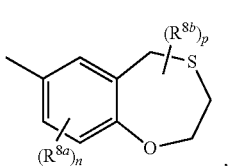
Z-20
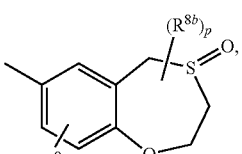
Z-21
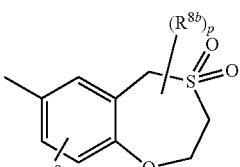
Z-22
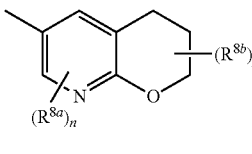
Z-23
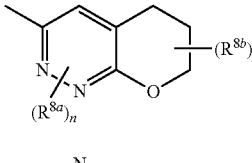
Z-24
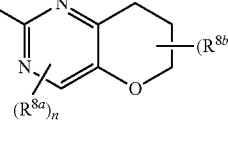
Z-25
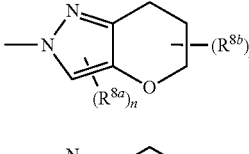
Z-26
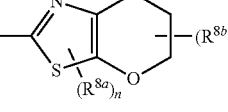
Z-27

-continued

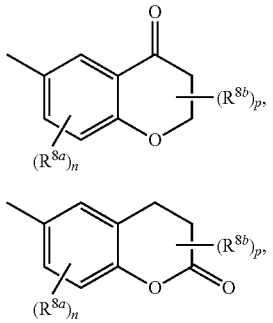

Z-28

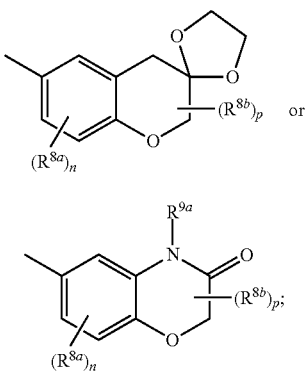

Z-29

Z-30

Z-31 wherein
R$^{9a}$ is independently H or R$^9$;
each R$^{8a}$ and R$^{8b}$ are independently R$^8$;
n is 0, 1 or 2; and
p is 0, 1 or 2.

Embodiment 26

A compound of Embodiment 25 wherein Z is Z-1, Z-2, Z-3, Z-4, Z-5, Z-6, Z-7, Z-8, Z-9, Z-10, Z-11, Z-12, Z-13, Z-14, Z-15, Z-16, Z-17, Z-18, Z-19, Z-20, Z-21 or Z-22.

Embodiment 27

A compound of Embodiment 26 wherein Z is Z-1, Z-2, Z-6, Z-7, Z-9, Z-10, Z-11 or Z-12.

Embodiment 28

A compound of Embodiment 27 wherein Z is Z-1, Z-2, Z-6, Z-9 or Z-10.

Embodiment 29

A compound of any one of Embodiments 13 through 28 wherein the second ring in the heterobicyclic ring system of Z is not substituted with R$^8$ or R$^9$ (i.e. p is 0 is in Embodiment 25).

Embodiment 30

A compound of the any one of Embodiments 13 through 29 wherein the first ring in the heterobicyclic ring system of Z is not substituted with R$^8$ or R$^9$ (i.e. n is 0 in Embodiments 23 through 25).

Embodiment 31

A compound of Formula 1 or any one of Embodiments 1 through 29 wherein each R$^8$ is independently halogen, cyano, hydroxy, amino, —CH(=O), —C(=O)NH$_2$, C$_1$-C$_4$ alkyl, C$_1$-C$_4$ haloalkyl, C$_3$-C$_4$ cycloalkyl, C$_2$-C$_5$ alkylcarbonyl, C$_2$-C$_5$ haloalkylcarbonyl, C$_1$-C$_4$ alkoxy, C$_1$-C$_4$ haloalkoxy or C$_3$-C$_4$ cycloalkoxy.

Embodiment 32

A compound of Embodiment 31 wherein each R$^8$ is independently halogen, cyano, hydroxy, amino, —CH(=O), —C(=O)NH$_2$, C$_1$-C$_3$ alkyl, C$_1$-C$_3$ haloalkyl, cyclopropyl, C$_2$-C$_3$ alkylcarbonyl, C$_2$-C$_3$ haloalkylcarbonyl, C$_1$-C$_3$ alkoxy, C$_1$-C$_3$ haloalkoxy or cyclopropoxy.

Embodiment 33

A compound of Embodiment 32 wherein each R$^8$ is independently halogen, C$_1$-C$_3$ alkyl, C$_1$-C$_2$ alkoxy or C$_2$-C$_3$ alkylcarbonyl.

Embodiment 34

A compound of Embodiment 33 wherein each R$^8$ is independently F, Cl, Br, methyl or methoxy.

Embodiment 35

A compound of Embodiment 34 wherein each R$^8$ is independently F, methyl or methoxy.

Embodiment 36

A compound of Embodiment 35 wherein each R$^8$ is independently F or methyl.

Embodiment 37

A compound of any one of Embodiments 23 through 28 wherein each R$^{8a}$ is independently halogen, C$_1$-C$_2$ alkyl or C$_1$-C$_2$ alkoxy.

Embodiment 38

A compound of Embodiment 37 wherein each R$^{8a}$ is independently F, Cl, Br, methyl or methoxy.

Embodiment 39

A compound of Embodiment 38 wherein each R$^{8a}$ is F.

Embodiment 40

A compound of any one of Embodiments 23 through 28 and 37 through 39 wherein each R$^{8b}$ is independently F, Cl, C$_1$-C$_3$ alkyl or C$_2$-C$_3$ alkylcarbonyl.

Embodiment 41

A compound of Embodiment 40 wherein each R$^{8b}$ is independently F or methyl.

Embodiment 42

A compound of Formula 1 or any one of Embodiments 1 through 41 wherein each R$^9$ is independently cyano, hydroxy, —CH(=O), —C(=O)NH$_2$, C$_1$-C$_4$ alkyl, C$_1$-C$_4$ haloalkyl, C$_3$-C$_4$ cycloalkyl, C$_2$-C$_5$ alkylcarbonyl, C$_2$-C$_5$ haloalkylcarbonyl, C$_1$-C$_4$ alkoxy, C$_1$-C$_4$ haloalkoxy or C$_3$-C$_4$ cycloalkoxy.

Embodiment 43

A compound of Embodiment 42 wherein each $R^9$ is independently cyano, hydroxy, —CH(=O), —C(=O)NH$_2$, $C_1$-$C_3$ alkyl, $C_1$-$C_3$ haloalkyl, cyclopropyl, $C_2$-$C_5$ alkylcarbonyl, $C_2$-$C_5$ haloalkylcarbonyl, $C_1$-$C_3$ alkoxy, $C_1$-$C_3$ haloalkoxy or cyclopropoxy.

Embodiment 44

A compound of Embodiment 43 wherein each $R^9$ is independently hydroxy, $C_1$-$C_2$ alkyl or $C_1$-$C_2$ alkoxy.

Embodiment 45

A compound of Embodiment 44 wherein each $R^9$ is independently $C_1$-$C_2$ alkyl.

Embodiment 46

A compound of Embodiment 45 wherein each $R^9$ is methyl.

Embodiment 47

A compound of Formula 1 or any one of Embodiments 1 through 46 wherein the fused heterobicyclic ring system is not substituted by $R^8$ or $R^9$ (including $R^{8a}$, $R^{8b}$ and $R^{9a}$).

Embodiment 48

A compound of Formula 1 or any one of Embodiments 1 through 47 wherein $R^1$ is halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_4$ cycloalkyl.

Embodiment 49

A compound of Embodiment 48 wherein $R^1$ is halogen, CN, $C_1$-$C_2$ alkyl, $C_1$-$C_2$ alkoxy, $C_1$-$C_2$ haloalkyl or $C_1$-$C_2$ haloalkoxy.

Embodiment 50

A compound of Embodiment 49 wherein $R^1$ is halogen, CN, $C_1$-$C_2$ alkyl or $C_1$-$C_2$ haloalkyl.

Embodiment 51

A compound of Embodiment 50 wherein $R^1$ is F, Cl, Br, CN, methyl or $C_1$ haloalkyl.

Embodiment 52

A compound of Embodiment 51 wherein $R^1$ is F, Cl, Br or methyl.

Embodiment 53

A compound of Embodiment 52 wherein $R^1$ is Cl, Br or methyl.

Embodiment 53a

A compound of Embodiment 52 wherein $R^1$ is F, Cl, or methyl.

Embodiment 54

A compound of Formula 1 or any one of Embodiments 1 through 53 wherein $R^2$ is H, halogen, CN, $C_1$-$C_3$ alkyl, $C_1$-$C_3$ alkoxy or $C_1$-$C_3$ haloalkyl.

Embodiment 55

A compound of Embodiment 54 wherein $R^2$ is H, halogen, CN, methyl or trifluoromethyl.

Embodiment 56

A compound of Embodiment 55 wherein $R^2$ is H or halogen.

Embodiment 57

A compound of Embodiment 56 wherein $R^2$ is H, F or Cl.

Embodiment 58

A compound of Embodiment 57 wherein $R^2$ is H.

Embodiment 59

A compound of Formula 1 or any one of Embodiments 1 through 58 wherein $R^3$ is H, $C_1$-$C_2$ alkyl, $C_1$-$C_2$ haloalkyl, $C_2$-$C_3$ alkylcarbonyl or $C_2$-$C_3$ haloalkylcarbonyl.

Embodiment 60

A compound of Embodiment 59 wherein $R^3$ is H, $C_1$-$C_2$ alkyl or $C_1$-$C_2$ haloalkyl.

Embodiment 61

A compound of Embodiment 60 wherein $R^3$ is H or methyl.

Embodiment 62

A compound of Embodiment 61 wherein $R^3$ is H.

Embodiment 63

A compound of Formula 1 or any one of Embodiments 1 through 62 wherein $R^4$ is H, $C_1$-$C_2$ alkyl, $C_1$-$C_2$ haloalkyl, $C_1$-$C_2$ alkoxy, $C_1$-$C_2$ haloalkoxy, $C_3$-$C_4$ cycloalkoxy, $C_1$-$C_2$ alkylamino, $C_1$-$C_2$ haloalkylamino, $C_2$-$C_4$ dialkylamino, $C_2$-$C_4$ halodialkylamino or $C_3$-$C_4$ cycloalkylamino.

Embodiment 64

A compound of Embodiment 63 wherein $R^4$ is H, $C_1$-$C_2$ alkyl, $C_1$-$C_2$ alkoxy, $C_1$-$C_2$ haloalkoxy, $C_1$-$C_2$ alkylamino or $C_2$-$C_4$ dialkylamino.

Embodiment 65

A compound of Embodiment 64 wherein $R^4$ is H, $C_1$-$C_2$ alkyl, $C_1$-$C_2$ alkoxy or $C_1$-$C_2$ haloalkoxy.

Embodiment 66

A compound of Embodiment 65 wherein $R^4$ is H, $C_1$-$C_2$ alkyl or methoxy.

Embodiment 67

A compound of Embodiment 66 wherein $R^4$ is H, methyl or methoxy.

Embodiment 68

A compound of Formula 1 or any one of Embodiments 1 through 67 wherein W is O.

Embodiment 69

A compound of Formula 1 or any one of Embodiments 1 through 68 wherein Q is $CR^{10a}R^{10b}$ or O.

Embodiment 70

A compound of Formula 1 or any one of Embodiments 1 through 68 wherein Q is $CR^{10a}R^{10b}$ or $NR^{11}$.

Embodiment 71

A compound of Formula 1 or any one of Embodiments 1 through 68 wherein Q is $CR^{10a}R^{10b}$.

Embodiment 72

A compound of Formula 1 or any one of Embodiments 1 through 68 wherein Q is O.

Embodiment 73

A compound of Formula 1 or any one of Embodiments 1 through 68 wherein Q is $NR^{11}$.

Embodiment 74

A compound of Formula 1 or any one of Embodiments 1 through 73 wherein when $R^{10a}$ is taken alone (i.e. $R^{10a}$ is not taken together with $R^{10b}$ and the carbon atom to which they are attached to form a ring) then $R^{10a}$ is H.

Embodiment 75

A compound of Formula 1 or any one of Embodiments 1 through 74 wherein when $R^{10b}$ is taken alone (i.e. $R^{10b}$ is not taken together with $R^{10a}$ and the carbon atom to which they are attached to form a ring) then $R^{10b}$ is H, methyl or cyclopropyl.

Embodiment 76

A compound of Embodiment 75 wherein when $R^{10b}$ is taken alone then $R^{10b}$ is H or methyl

Embodiment 77

A compound of Embodiment 76 wherein when $R^{10b}$ is taken alone then $R^{10b}$ is H.

Embodiment 78

A compound of Formula 1 or any one of Embodiments 1 through 77 wherein when $R^{10a}$ and $R^{10b}$ are taken together with the carbon atom to which they are attached to form a ring, the ring is a cyclopropyl ring.

Embodiment 79

A compound of Formula 1 or any one of Embodiments 1 through 77 wherein $R^{10a}$ and $R^{10b}$ are taken alone (i.e. $R^{10a}$ and $R^{10b}$ are not taken together with the carbon atom to which they are attached to form a ring).

Embodiment 80

A compound of Formula 1 or any one of Embodiments 1 through 79 wherein $R^{11}$ is H.

Embodiment 81

A compound of Formula 1 or any one of Embodiments 1 through 80 wherein z is 0.

Embodiment 82

A compound of Formula 1 or any one of Embodiments 1 through 81 wherein u is 0.

Embodiments of this invention, including Embodiments 1-82 above as well as any other embodiments described herein, can be combined in any manner, and the descriptions of variables in the embodiments pertain not only to the compounds of Formula 1 but also to the starting compounds and intermediate compounds useful for preparing the compounds of Formula 1. In addition, embodiments of this invention, including Embodiments 1-82 above as well as any other embodiments described herein, and any combination thereof, pertain to the compositions and methods of the present invention.

Combinations of Embodiments of 1-82 are illustrated by:

Embodiment A

A compound of Formula 1 wherein

Y is a 5-membered, fully or partially unsaturated heterocyclic ring containing 2-4 carbon atoms and 2-3 nitrogen atoms as ring members, the ring substituted with Z on a ring member atom connected through an adjacent single ring member atom to the ring member atom attaching the heterocyclic ring to the phenyl ring of Formula 1, and optionally further substituted with up to 2 substituents independently selected from $R^5$ on carbon atom ring members and from $R^6$ on nitrogen atom ring members;

Z is an 8-, 9-, 10- or 11-membered fused heterobicyclic ring system containing ring members selected from carbon atoms and 1 to 4 heteroatoms independently selected from up to 2 O, up to 2 S and up to 4 N atoms, wherein up to 3 carbon atom ring members are independently selected from C(=O) and C(=S), and the sulfur atom ring members are independently selected from $S(=O)_u(=NR^7)_z$, the ring system optionally substituted with substituents independently selected from $R^8$ on carbon atom ring members and from $R^9$ on nitrogen atom ring members;

W is O or S;

Q is $CR^{10a}R^{10b}$, O or $NR^{11}$;

$R^1$ is halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_6$ cycloalkyl;

$R^2$ is H, halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_6$ cycloalkyl;

$R^3$ is H, $C_1$-$C_3$ alkyl, $C_1$-$C_3$ haloalkyl, $C_3$-$C_4$ cycloalkyl, $C_3$-$C_4$ halocycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;

$R^4$ is H, hydroxy, amino, $C_1$-$C_4$ alkyl, $C_1$-$C_4$ haloalkyl, $C_3$-$C_4$ cycloalkyl, $C_3$-$C_4$ halocycloalkyl, $C_1$-$C_4$ alkoxy, $C_1$-$C_4$ haloalkoxy, $C_3$-$C_4$ cycloalkoxy, $C_1$-$C_4$ alkylamino, C$_1$-C$_4$ haloalkylamino, C$_2$-C$_6$ dialkylamino, C$_2$-C$_6$ halodialkylamino or C$_3$-C$_4$ cycloalkylamino;

each R$^5$ is independently halogen, cyano, hydroxy, amino, nitro, C$_1$-C$_6$ alkyl, C$_3$-C$_5$ cycloalkyl, C$_3$-C$_5$ halocycloalkyl, C$_2$-C$_6$ alkenyl, C$_2$-C$_6$ alkynyl or C$_1$-C$_6$ haloalkyl;

each R$^6$ is independently cyano, hydroxy, C$_1$-C$_6$ alkyl, C$_1$-C$_6$ haloalkyl, C$_3$-C$_5$ cycloalkyl, C$_3$-C$_5$ halocycloalkyl, C$_2$-C$_6$ alkenyl or C$_3$-C$_6$ alkynyl;

each R$^8$ is independently halogen, cyano, hydroxy, amino, nitro, —CH(=O), —C(=O)OH, —C(=O)NH$_2$, —C(R$^{12}$)=N—O—R$^{13}$, —C(R$^{12}$)=N—R$^{13}$, C$_1$-C$_4$ alkyl, C$_1$-C$_4$ haloalkyl, C$_3$-C$_4$ cycloalkyl, C$_2$-C$_4$ alkenyl, C$_2$-C$_4$ alkynyl, C$_2$-C$_5$ alkylcarbonyl, C$_2$-C$_5$ haloalkylcarbonyl, C$_4$-C$_5$ cycloalkylcarbonyl, C$_2$-C$_5$ alkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_5$ cycloalkylaminocarbonyl, C$_1$-C$_4$ alkoxy, C$_1$-C$_4$ haloalkoxy, C$_3$-C$_4$ cycloalkoxy, C$_3$-C$_4$ halocycloalkoxy, C$_4$-C$_5$ cycloalkylalkoxy, C$_2$-C$_4$ alkenyloxy, C$_2$-C$_4$ haloalkenyloxy, C$_2$-C$_4$ alkynyloxy, C$_3$-C$_4$ haloalkynyloxy, C$_2$-C$_4$ alkoxyalkoxy, C$_2$-C$_8$ alkylcarbonyloxy, C$_2$-C$_8$ haloalkylcarbonyloxy, C$_4$-C$_{10}$ cycloalkylcarbonyloxy, C$_1$-C$_4$ alkylthio, C$_1$-C$_4$ haloalkylthio, C$_3$-C$_6$ cycloalkylthio, C$_1$-C$_4$ alkylsulfonyl, C$_1$-C$_4$ haloalkylsulfinyl, C$_1$-C$_4$ alkylsulfonyl, C$_1$-C$_4$ haloalkylsulfonyl, C$_3$-C$_5$ cycloalkylsulfonyl, C$_3$-C$_7$ trialkylsilyl, C$_1$-C$_4$ alkylamino, C$_2$-C$_8$ dialkylamino, C$_1$-C$_4$ haloalkylamino, C$_2$-C$_8$ halodialkylamino, C$_3$-C$_6$ cycloalkylamino, C$_2$-C$_5$ alkylcarbonylamino or C$_2$-C$_5$ haloalkylcarbonylamino;

each R$^9$ is independently cyano, hydroxy, —CH(=O), —C(=O)NH$_2$, —C(R$^{12}$)=N—O—R$^{13}$, —C(R$^{12}$)=N—R$^{13}$, C$_1$-C$_4$ alkyl, C$_3$-C$_4$ cycloalkyl, C$_2$-C$_4$ alkenyl, C$_2$-C$_4$ alkynyl, C$_1$-C$_4$ haloalkyl, C$_2$-C$_5$ alkylcarbonyl, C$_2$-C$_5$ haloalkylcarbonyl, C$_4$-C$_5$ cycloalkylcarbonyl, C$_2$-C$_5$ alkoxycarbonyl, C$_4$-C$_{10}$ cycloalkoxycarbonyl, C$_2$-C$_8$ alkylaminocarbonyl, C$_3$-C$_{10}$ dialkylaminocarbonyl, C$_4$-C$_5$ cycloalkylaminocarbonyl, C$_1$-C$_4$ alkoxy, C$_1$-C$_4$ haloalkoxy, C$_3$-C$_4$ cycloalkoxy, C$_3$-C$_4$ halocycloalkoxy, C$_4$-C$_5$ cycloalkylalkoxy, C$_2$-C$_4$ alkenyloxy, C$_2$-C$_4$ haloalkenyloxy, C$_2$-C$_4$ alkynyloxy, C$_3$-C$_4$ haloalkynyloxy, C$_2$-C$_4$ alkoxyalkoxy, C$_2$-C$_8$ alkylcarbonyloxy, C$_2$-C$_8$ haloalkylcarbonyloxy, C$_4$-C$_{10}$ cycloalkylcarbonyloxy, C$_1$-C$_6$ alkylthio, benzylthio, C$_1$-C$_6$ haloalkylthio, C$_3$-C$_8$ cycloalkylthio, C$_1$-C$_4$ alkylsulfonyl, C$_1$-C$_4$ haloalkylsulfonyl, C$_3$-C$_6$ cycloalkylsulfonyl or C$_3$-C$_{10}$ trialkylsilyl;

each R$^7$ and R$^{13}$ is independently H, C$_1$-C$_3$ alkyl, C$_1$-C$_3$ haloalkyl, C$_2$-C$_3$ alkylcarbonyl or C$_2$-C$_3$ haloalkylcarbonyl;

R$^{10a}$ is H, OH, halogen, cyano, C$_1$-C$_3$ alkyl, C$_1$-C$_3$ haloalkyl, C$_2$-C$_3$ alkoxyalkyl, C$_1$-C$_3$ alkoxy, C$_1$-C$_3$ haloalkoxy or C$_1$-C$_3$ alkylsulfonyl;

R$^{10b}$ is H, C$_1$-C$_3$ alkyl, C$_1$-C$_3$ haloalkyl, C$_2$-C$_3$ alkoxyalkyl, C$_1$-C$_3$ alkoxy or C$_1$-C$_3$ haloalkoxy; or R$^{10a}$ and R$^{10b}$ are taken together with the carbon atom to which they are attached to form a C$_3$-C$_4$ cycloalkyl or C$_3$-C$_4$ halocycloalkyl ring;

R$^{11}$ is H, C$_1$-C$_3$ alkyl, C$_1$-C$_3$ haloalkyl, C$_2$-C$_3$ alkylcarbonyl or C$_2$-C$_3$ haloalkylcarbonyl;

each R$^{12}$ is independently H, C$_1$-C$_3$ alkyl, C$_3$-C$_5$ cycloalkyl or C$_1$-C$_3$ haloalkyl; and u and z in each instance of S(=O)$_u$(=NR$^7$)$_z$ are independently 0, 1 or 2, provided that the sum of u and z in each instance of S(=O)$_u$(=NR$^7$)$_z$ is 0, 1 or 2.

Embodiment A1

A compound of Formula 1 as described in the Summary of the Invention or Embodiment A wherein
R$^1$ is halogen, CN, C$_1$-C$_3$ alkyl, C$_1$-C$_3$ alkoxy, C$_1$-C$_3$ haloalkyl, C$_1$-C$_3$ haloalkoxy or C$_3$-C$_4$ cycloalkyl;
R$^2$ is H, halogen, CN C$_1$-C$_3$ alkyl, C$_1$-C$_3$ alkoxy or C$_1$-C$_3$ haloalkyl;
R$^3$ is H, C$_1$-C$_2$ alkyl, C$_1$-C$_2$ haloalkyl, C$_2$-C$_3$ alkylcarbonyl or C$_2$-C$_3$ haloalkylcarbonyl;
R$^4$ is H, C$_1$-C$_2$ alkyl, C$_1$-C$_2$ haloalkyl, C$_1$-C$_2$ alkoxy, C$_1$-C$_2$ haloalkoxy, C$_3$-C$_4$ cycloalkoxy, C$_1$-C$_2$ alkylamino, C$_1$-C$_2$ haloalkylamino, C$_2$-C$_4$ dialkylamino, C$_2$-C$_4$ halodialkylamino or C$_3$-C$_4$ cycloalkylamino;
each R$^5$ is independently halogen, cyano, C$_1$-C$_2$ alkyl or C$_1$-C$_2$ haloalkyl;
R$^{5a}$ is H or R$^5$;
R$^{6a}$ is H, C$_1$-C$_2$ alkyl, C$_1$-C$_2$ haloalkyl;
each R$^8$ is independently halogen, cyano, hydroxy, amino, —CH(=O), —C(=O)NH$_2$, C$_1$-C$_4$ alkyl, C$_1$-C$_4$ haloalkyl, C$_3$-C$_4$ cycloalkyl, C$_2$-C$_5$ alkylcarbonyl, C$_2$-C$_5$ haloalkylcarbonyl, C$_1$-C$_4$ alkoxy, C$_1$-C$_4$ haloalkoxy or C$_3$-C$_4$ cycloalkoxy;
each R$^9$ is independently cyano, hydroxy, —CH(=O), —C(=O)NH$_2$, C$_1$-C$_4$ alkyl, C$_1$-C$_4$ haloalkyl, C$_3$-C$_4$ cycloalkyl, C$_2$-C$_5$ alkylcarbonyl, C$_2$-C$_5$ haloalkylcarbonyl, C$_1$-C$_4$ alkoxy, C$_1$-C$_4$ haloalkoxy or C$_3$-C$_4$ cycloalkoxy;
R$^{10a}$ is H;
R$^{10b}$ is H, methyl or cyclopropyl; or
R$^{10a}$ and R$^{10b}$ are taken together with the carbon atom to which they are attached to form a cyclopropyl ring;
R$^{11}$ is H;
W is O; and
Y is a 5-membered heterocycle selected from Y-1 through Y-25 (depicted in Exhibit 1);
wherein in the fused heterobicyclic ring system of Z (defined in the Summary of the Invention) the ring that is directly bonded to Y is aromatic and is identified as a first ring, the ring that is fused to the first ring is identified as a second ring, the second ring includes an O atom as a ring member directly bonded to a ring fusion atom shared with the first ring, and said ring fusion atom is connected through no less than one intervening ring member atom (in the first ring) to the ring member atom (in the first ring) directly bonded to Y.

Embodiment A2

A compound of Embodiment A1 wherein
R$^1$ is halogen, CN, C$_1$-C$_2$ alkyl, C$_1$-C$_2$ alkoxy, C$_1$-C$_2$ haloalkyl or C$_1$-C$_2$ haloalkoxy;
R$^2$ is H, halogen, CN, methyl or trifluoromethyl;
R$^3$ is H or methyl;
R$^4$ is H, C$_1$-C$_2$ alkyl, C$_1$-C$_2$ alkoxy or C$_1$-C$_2$ haloalkoxy;
each R$^5$ is independently halogen or methyl;
R$^{6a}$ is H, methyl or trifluoromethyl;
R$^{10a}$ is H;
R$^{10b}$ is H, methyl or cyclopropyl;
Y is Y-1, Y-2, Y-3, Y-4, Y-5, Y-6, Y-7, Y-8, Y-13, Y-14, Y-15, Y-16, Y-18 or Y-25;
Z is selected from Z-A through Z-F (as shown in Exhibit 2A);
L is a linking chain containing 2-4 chain members selected from carbon atoms and up to 2 heteroatoms independently selected from up to 2 O, up to 1 S and up to 1 N atoms, wherein up to 2 carbon atom ring members are independently selected from C(=O) and C(=S), and the sulfur atom ring members are independently selected from $S(=O)_u(=NR^7)_z$, the linking chain optionally substituted with up to 4 substituents independently selected from $R^{8b}$ on carbon atom ring members and from $R^9$ on nitrogen atom ring members;
$R^9$ is hydroxy, $C_1$-$C_2$ alkyl or $C_1$-$C_2$ alkoxy; and
n is 0, 1 or 2 (limited by the number of available bonding positions).

Embodiment A3

A compound of Embodiment A2 wherein
$R^1$ is halogen, CN, $C_1$-$C_2$ alkyl or $C_1$-$C_2$ haloalkyl;
$R^2$ is H or halogen;
$R^3$ is H;
$R^4$ is H, $C_1$-$C_2$ alkyl or methoxy;
$R^{5a}$ is H;
$R^{6a}$ is H or methyl;
each $R^{8a}$ is independently halogen, $C_1$-$C_2$ alkyl or $C_1$-$C_2$ alkoxy;
each $R^{8b}$ is independently F, Cl, $C_1$-$C_3$ alkyl or $C_2$-$C_3$ alkylcarbonyl;
$R^{10b}$ is H or methyl;
Y is Y-1, Y-3, Y-4, Y-5, Y-7, Y-8 or Y-25;
Z is selected from Z-1 through Z-27 (as shown in Exhibit 2B);
$R^{9a}$ is H or $C_1$-$C_2$ alkyl;
m is 0;
n is 0, 1 or 2; and
p is 0, 1 or 2.

Embodiment A4

A compound of Embodiment A3 wherein
$R^1$ is F, Cl, Br or methyl;
$R^2$ is H, F or Cl;
$R^4$ is H, methyl or methoxy;
each $R^{8a}$ is independently F, Cl, Br, methyl or methoxy;
each $R^{8b}$ is independently F or methyl;
$R^{10b}$ is H;
Q is $CR^{10a}R^{10b}$;
Y is Y-3, Y-4, Y-7 or Y-8; and
Z is Z-1, Z-2, Z-6, Z-9 or Z-10.

Specific embodiments include compounds of Formula 1 selected from the group consisting of:
methyl N-[[2-chloro-5-[1-(3,4-dihydro-2H-1-benzopyran-6-yl)-1H-pyrazol-3-yl]-phenyl]methyl]carbamate;
methyl N-[[2-chloro-5-[3-(3,4-dihydro-2H-1-benzopyran-6-yl)-1H-pyrazol-1-yl]-phenyl]methyl]carbamate;
methyl N-[[5-[3-(1,3-benzodioxol-5-yl)-1H-pyrazol-1-yl]-2-chlorophenyl]-methyl]carbamate; and
methyl N-[[2-chloro-5-[3-(2,3-dihydro-1,4-benzodioxin-6-yl)-1H-pyrazol-1-yl]-phenyl]methyl]carbamate.

Further specific embodiments include compounds of Formula 1 selected from the group consisting of:
methyl N-[[5-[1-(3,4-dihydro-2H-1-benzopyran-6-yl)-1H-pyrazol-3-yl]-2-fluorophenyl]methyl]carbamate;
methyl N-[[5-[1-(3,4-dihydro-2H-1-benzopyran-6-yl)-1H-pyrazol-3-yl]-2-methylphenyl]methyl]carbamate;
methyl N-[[5-[3-(3,4-dihydro-2H-1-benzopyran-6-yl)-1H-pyrazol-1-yl]-2-fluorophenyl]methyl]carbamate; and
methyl N-[[5-[3-(3,4-dihydro-2H-1-benzopyran-6-yl)-1H-pyrazol-1-yl]-2-methylphenyl]methyl]carbamate.

This invention provides a fungicidal composition comprising a compound of Formula 1 (including all stereoisomers, N-oxides, and salts thereof), and at least one other fungicide. Of note as embodiments of such compositions are compositions comprising a compound corresponding to any of the compound embodiments described above.

This invention provides a fungicidal composition comprising a compound of Formula 1 (including all stereoisomers, N-oxides, and salts thereof) (i.e. in a fungicidally effective amount), and at least one additional component selected from the group consisting of surfactants, solid diluents and liquid diluents. Of note as embodiments of such compositions are compositions comprising a compound corresponding to any of the compound embodiments described above.

This invention provides a method for controlling plant diseases caused by fungal plant pathogens comprising applying to the plant or portion thereof, or to the plant seed, a fungicidally effective amount of a compound of Formula 1 (including all stereoisomers, N-oxides, and salts thereof). Of note as embodiment of such methods are methods comprising applying a fungicidally effective amount of a compound corresponding to any of the compound embodiments describe above. Of particular note are embodiments where the compounds are applied as compositions of this invention.

One or more of the following methods and variations as described in Schemes 1-19 can be used to prepare the compounds of Formula 1. The definitions of $R^1$, $R^2$, $R^3$, $R^4$, $R^{5a}$, Q, W, Y and Z in the compounds of Formulae 1-32 below are as defined above in the Summary of the Invention unless otherwise noted. Formulae 1a-1d are various subsets of Formula 1, and all substituents for Formulae 1a-1d are as defined above for Formula 1.

As shown in Scheme 1, compounds of Formula 1 can be prepared by the well-known Suzuki reaction via Pd-catalyzed cross-coupling of an aromatic iodide or bromide of Formula 2 wherein $X^1$ is Br or I with a substituted unsaturated heterocyclic boronic acid or ester of Formula 3. For typical Suzuki reactions conditions see, for example, Suzuki et al., *Chemical Review*, 1995, 95, 2457-2483. A wide variety of catalysts are useful for this type of transformation; particularly useful as a catalyst is tetrakis(triphenylphosphine)-palladium(0). Solvents such as tetrahydrofuran, acetonitrile, diethyl ether and dioxane are suitable. The boronic acids and esters of Formula 3 are either commercially available or can be prepared by known methods. Compounds of Formula 1 wherein Y is a N-linked substituted unsaturated heterocyclic ring can be prepared via a copper-catalyzed cross-coupling reaction using compounds of Formula 4. For leading references see, for example, Buchwald et al., *Accounts of Chemical Research*, 1998, 31(12), 805-818 and Hartwig, *Angew. Chem. Int. Ed.*, 1998, 37, 2046-2067.

Scheme 1

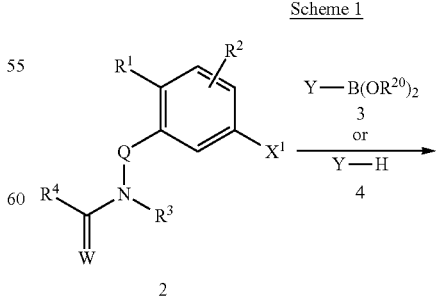

wherein $X^1$ is Br or I and $(OR^{20})_2$ is $(OH)_2$ or tetramethyldioxaborolane -continued

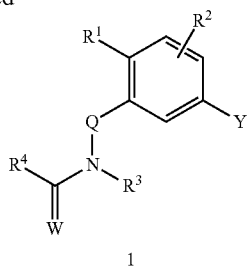

1

As shown in Scheme 2, compounds of Formula 2 can be prepared by reacting a substituted amine of Formula 5 with an acid chloride of Formula 6 in the presence of a base such as triethylamine or pyridine. The reaction can be carried out with or without solvent. Suitable solvents include dichloromethane, chloroform, diethyl ether or tetrahydrofuran at temperatures ranging from about 0 to about 50° C. For a related reference see European Patent Publication EP 1586552. For a general synthesis of compounds of Formula 6, see *Advanced Organic Synthesis*, 4th Edition, Wiley & Sons 1992, 437, and references cited therein. For synthesis of a compound of Formula 2 wherein Q is $NR^{11}$ and $R^{11}$ is H see World Patent Publication WO 2004/037770. Also, U.S. Pat. No. 6,313,071 describes the method of Scheme 2 when Q is $CH_2$. Additionally, U.S. Pat. No. 6,313,071 describes an alternative method for preparing certain compounds of Formula 2 when Q is $CH_2$, involving first preparing an isocyanate from the amine of Formula 5 and then reacting the isocyanate with a compound of Formula $R^4H$ wherein $R^4$ is alkoxy or alkylamino to provide a compound of Formula 2.

Scheme 2

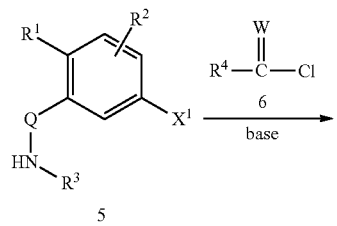

5
wherein $X^1$ is halogen

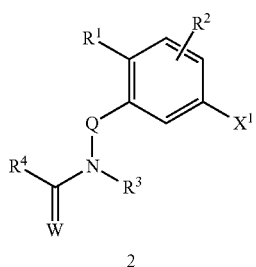

2

Compounds of Formula 5 are known or can be easily synthesized by general methods known to one skilled in the art. Many compounds of Formula 5 wherein Q is $CH_2$ are commercially available or are described in the chemical literature (U.S. Pat. No. 6,313,071 and European Patent 1,586, 552). Compounds of Formula 5a (Formula 5 wherein Q is O and $R^3$ is H) can be prepared from simple fluorobenzene derivatives of Formula 7 as shown in Scheme 3. The reaction of a compound of Formula 7 with a acetohydroxamate of Formula 8 is typically carried out in a polar aprotic solvent such as N,N-dimethylformamide in the presence of a suitable base such as potassium tert-butoxide or sodium hydride at temperatures ranging from about −10 to 120° C. The resulting compound of Formula 9 can then be deprotected using a strong acid such as perchloric acid at temperatures ranging from about −10 to about 40° C. to give a compound of Formula 5a (for a relevant reference see, for example, Kikugawa et al., *Organic Preparations and Procedures International* 1997, 29(5), 594-600).

Scheme 3

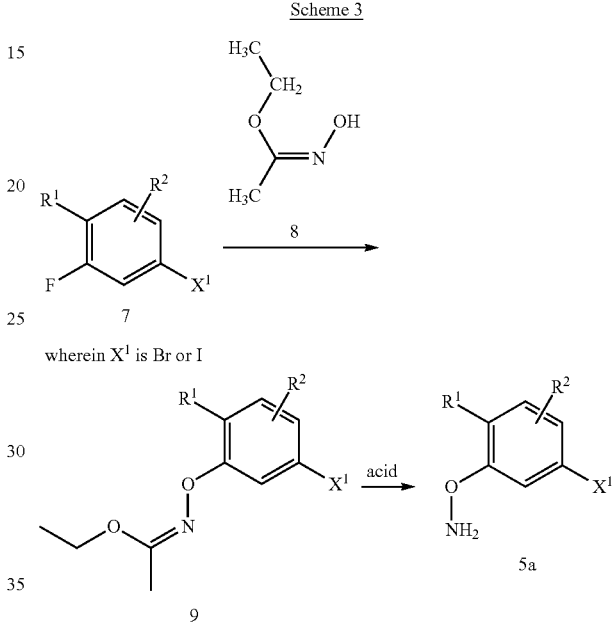

wherein $X^1$ is Br or I

A variety of general methods known in the art are useful for preparing compounds of Formula 3. Illustrative of these methods is the method depicted in Scheme 4 for preparing compounds of Formula 3a (i.e. Formula 3 wherein Y is Y-7 of Exhibit 1 and m is 0). In this method a sydnone of Formula 10 is contacted with an alkynyl boronate of Formula 11 in an aromatic solvent, such as mesitylene, at a temperature between 75° C. and the boiling point of the solvent. For a related reference, see D. Browne et al., *Angew Chem. Int. Ed.* 2007, 46, 8656-58. The compound of Formula 11 is commercially available or can be prepared according to A. Geny et al. *Chemistry—A European Journal* 2007, 13, 5408-25.

Scheme 4

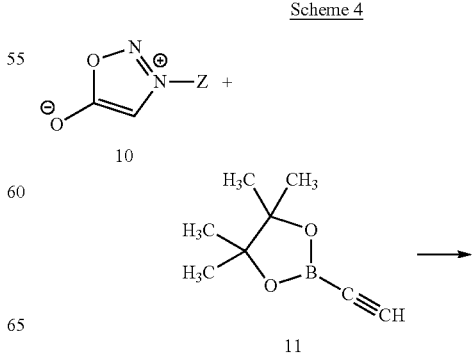

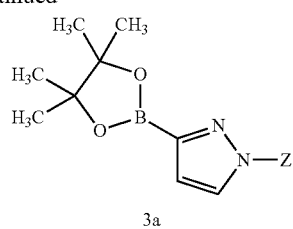

Sydnones of Formula 10 can be prepared as shown in Scheme 5. In this method, the intermediate compound of Formula 12 is prepared by a copper-catalyzed cross-coupling reaction between glycine (13) and a compound of Formula 14 wherein $X^2$ is bromine or iodine according to the general procedure of S. Roettger et al., *J. Combinatorial Chem.* 2007, 9, 204-9. The sydnone of Formula 10 can then prepared from the compound of Formula 12 by many procedures published in the literature, including C. J. Thoman et al., *Organic Syntheses* 1965, Vol. 45, pages 96-99.

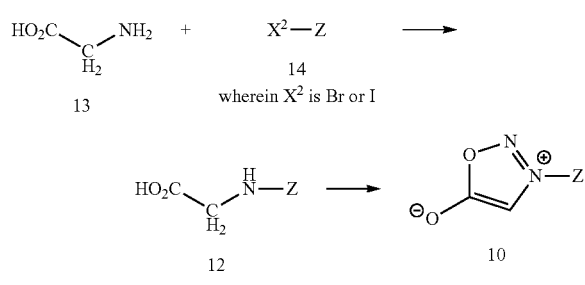

Compounds of Formula 14 are either commercially available or can be prepared by a variety of methodologies known in the art of organic synthesis. For example, compounds of Formula 14 can be prepared according to procedures in World Patent Publication WO 2009/062289 (Z-1, Z-6, Z-7, Z-8 and Z-15), T. Muraki et al., *Tetrahedron Lett.* 1996, 37, 2441-2444 (Z-6), T. Hideo et al., *J. Chem. Soc., Perkin Transactions 1* 1997, 5, 787-793 (Z-6 and Z-9), S. Cabiddu et al., *J. Het. Chem.* 1982, 19, 135-139 (Z-3 and Z-4), World Patent Publication WO 2007/067511 (Z-16 and Z-18), F. D. Chattaway, *J. Chem. Soc.* 1933, 699-700 (Z-10), R. Caputo et al., *Gazzetta Chimica Italiana* 1996, 126, 595-598 (Z-11), E. C. Taylor et al., *Tetrahedron* 1987, 43, 5145-5158 (Z-23), World Patent Publication WO 2003/059269 (Z-9 and Z-15), World Patent Publication WO 2002/098863 (Z-17), World Patent Publication WO 2009/000745 (Z-24), L Gavara et al., *Tetrahedron* 2008, 64, 4999-5004 (Z-2) and M. Kulka *Canadian J. Chem.* 1955, 33, 1442-49 (Z-20, Z-21 and Z-22). Compounds of Formula 14 are commercially available for Z-2, Z-6, Z-8, Z-9 and Z-16.

A variety of general methods known in the art are useful for preparing compounds of Formula 4. Illustrative of these methods is the method depicted in Scheme 6 for preparing compounds of Formula 4a (i.e. Formula 4 wherein Y is Y-3 of Exhibit 1 and m is 0). In this method, a compound of Formula 4a is prepared by the well-known Suzuki reaction involving palladium-catalyzed cross-coupling of an aromatic halide of Formula 14 wherein $X^2$ is Br or I with a commercially available pyrazole boronic acid of Formula 15. Although an pyrazole ring is used to illustrate the method of Scheme 6, one skilled in the art recognizes that the Suzuki reaction can be used with other unsaturated heterocyclic boronic acids. For typical Suzuki reaction conditions, see, for example, Suzuki et al., *Chemical Review* 1995, 95, 2457-2483. This method is demonstrated in Step A of Synthesis Example 1.

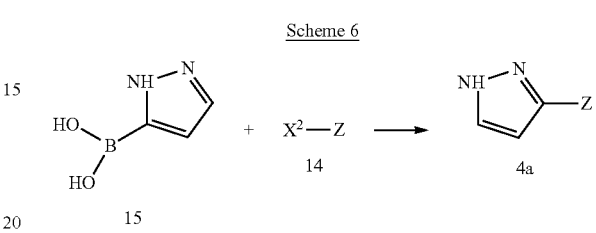

Another method for preparing compounds of Formula 1 utilizes the strategy of building the Y ring from an acyl group. Compounds of Formula 16 can be prepared from compounds of Formula 2 by reaction with acetic anhydride in the presence of a palladium catalysis as shown in Scheme 7. For a reference illustrating the method of Scheme 7 see, for example, Cacchi et al., *Organic Letters* 2003, 5(3), 289-291.

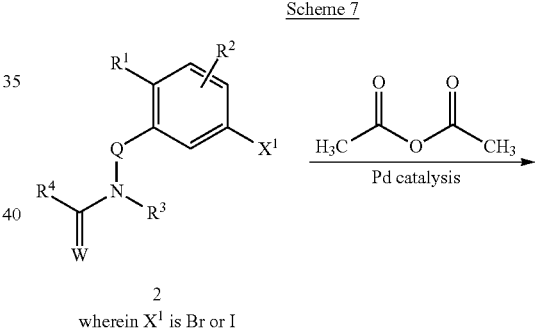

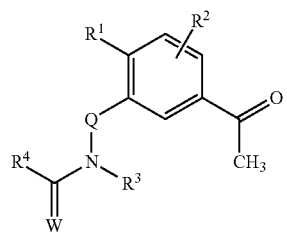

Compounds of Formula 16 can also be prepared as shown in Scheme 8. The method first involves reacting a compound of Formula 2 with a vinyl ether of Formula 17 in the presence of a palladium catalysis according to the general procedures reported in the literature (see, for example, Xiao et al., *J. Organic Chem.* 2006, 71, 7467-7470).

Scheme 8

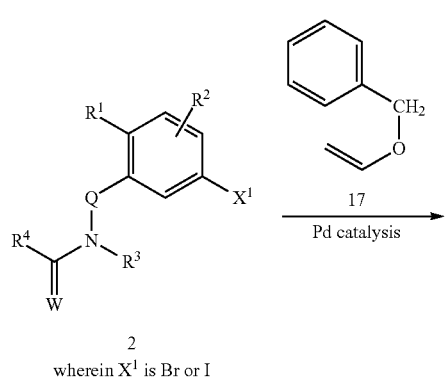

2
wherein X¹ is Br or I

As shown in Scheme 9, certain compounds of Formula 18 can be prepared by first reacting a compound of Formula 16 with N,N-dimethylformamide dimethyl acetal (DMF-DMA) at temperatures ranging from about 40 to about 100° C. in a lower alkanol solvent such as methanol or ethanol, which can optionally comprise water, to provide an intermediate compound of Formula 19. In a subsequent step, the compound of Formula 19 is reacted with hydrazine to provide a compound of Formula 18. One skilled in the art will recognize that there are other methods for performing transformations of this type, for example, the method described by Barrett et al., *Bioorganic and Medicinal Chemistry Letters* 2005, 15, 3540-3546. The method of Scheme 9 is illustrated in Steps A and B of Example 4.

Scheme 9

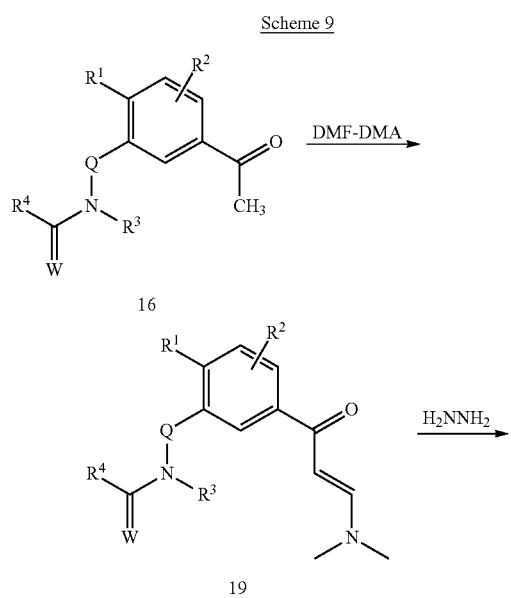

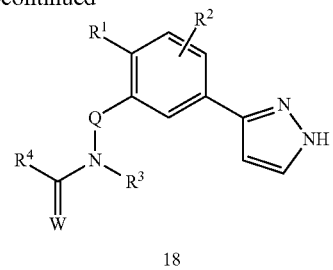

As shown in Scheme 10, certain compounds of Formula 1a (Formula 1 wherein Y is Y-7, R⁵ is CH₃ and Z is any of the heterocycles in Exhibit 2B) can be prepared from a compound of Formula 18 by reaction with a compound of Formula 14. The reaction is optionally run in the presence of a catalyst, typically comprising palladium or copper. For leading references see Buchwald et al., *Accounts of Chemical Research*, 1998, 31(12), 805-818. Alternatively, compounds of Formula 1a can be prepared by reacting a compound of Formula 18 with a boronic ester of Formula 19 in the presence of a suitable copper salt. For leading references see Chan et al., in *Boronic Acids*, 205-240, D. G. Hall, Ed., Wiley-VCH. Example 4 Step E illustrates the method of Scheme 10 for the preparation of a compound of Formula 1a from a compound of Formula 18 using a compound of Formula 14.

Scheme 10

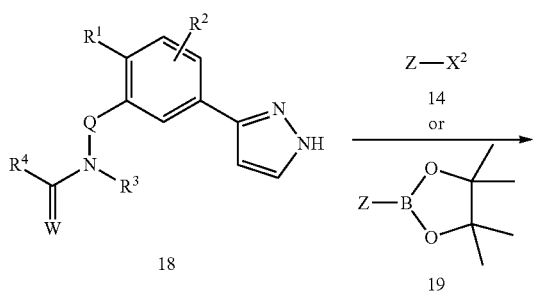

As shown in Scheme 11, compounds of Formula 19 can be prepared through the Pd-catalyzed cross-coupling of an aromatic iodide or bromide of Formula 14 wherein X is Br or I with a commercially available boronic acid ester like that of Formula 20. For typical Suzuki reactions conditions see, for example, Ishiyama, T. et al. *J. Org. Chem.* 1995, 60, 7508-10.

Scheme 11

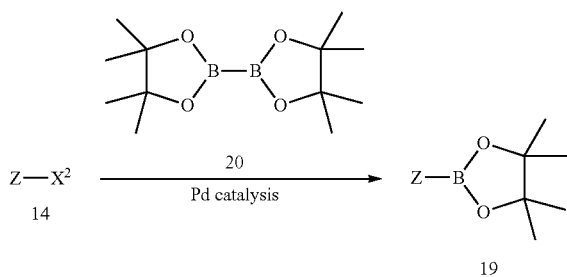

As shown in Scheme 12 compounds of Formula 1b (Formula 1 wherein Y is Y-7, $R^5$ is $CH_3$ and Z is any of the heterocycles in Exhibit 2B) can be prepared from a compound of Formula 21 by reaction with a compound of Formula 14 or Formula 19. The reaction is run in the presence of a catalyst similar to that shown in Scheme 10. For leading references see Buchwald et al., *Accounts of Chemical Research*, 1998, 31(12), 805-818, Chan et al., in *Boronic Acids*, 205-240, D. G. Hall, Ed. and Taillefer et al., *Angew. Chem. Int. Ed.* 2007, 46, 934-936.

Scheme 12

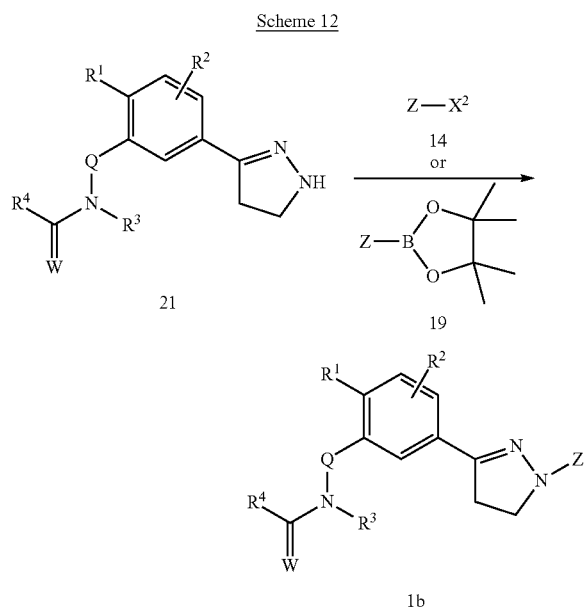

Compounds of Formula 21 are prepared from compounds of Formula 16 as shown in Scheme 13. Compounds of Formula 21 are prepared by reaction compounds of Formula 22 with hydrazine in a lower alcohol solvent, such as methanol, in the presence of a suitable base, such as sodium hydroxide, at a temperature between ambient and the reflux temperature of the solvent. Compounds of Formula 22 can be prepared by reacting compounds of Formula 16 with dimethylamine hydrochloride and formaldehyde in the presence of a lower alcohol solvent, such as ethanol, at a temperature between ambient and the reflux temperature of the solvent. For a related reference see B. Tian et al. *Bioorg. Med. Chem. Lett.* 2009, 19, 2162-67.

Scheme 13

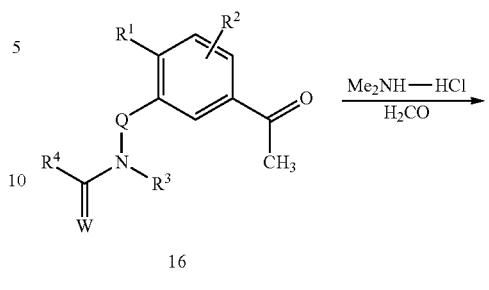

As shown in Scheme 14 compounds of Formula 1c (Formula 1 wherein Y is Y-17 and Y-18 and Z is one of the heterocycles listed in Exhibit 2B) can be prepared from a compound of Formula 23. A compound of Formula 23 is reacted with a compound of Formula 14 in the presence of iron(III) acetylacetonate ($Fe(acac)_3$), copper oxide and cesium carbonate in N,N-dimethylformamide at temperatures ranging from about 25 to about 150° C. as described by Taillefer et al., *Angew. Chem. Int. Ed.* 2007, 46, 934-936. Typically mixtures of regioisomers of Formula 1c are obtained from these reactions. Purification of the regioisomers is achieved by chromatography.

Scheme 14

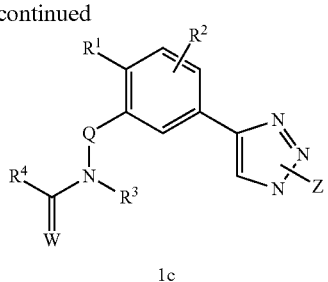

1c

As shown in Scheme 15, compounds of Formula 23 can be prepared in three-step synthesis starting from a compound Formula 2. In step 1 of Scheme 15, trimethylsilyl substituted alkynes of Formula 24 are obtained by contacting a compound of Formula 2 with ethynyltrimethylsilane in the presence of a suitable palladium catalyst (such as, for example, tetrakis(triphenylphosphine)palladium or dichlorobis(triphenylphosphine)palladium) and in the presence of a suitable copper catalyst (such, as for example, copper(I) iodide). In this method the mole ratio of ethynyltrimethylsilane to the compound of Formula 2 is typically from about 1.1 to about 5, and the mole ratios of the palladium catalyst and the copper catalyst to the compound of Formula 2 are each about 0.005 to about 0.1. The reaction is preferably run in the presence of a suitable amine base such as, for example, an amine base comprising triethylamine, N,N-diisopropylethylamine, diethylamine or piperidine. The reaction is preferably conducted in the presence of a solvent. However, in some cases the reaction can be carried out without solvent other than the compound of Formula 2, the ethynyltrimethylsilane and the amine base. But a preferred procedure involves use of a suitable solvent including, for example, tetrahydrofuran, toluene or N,N-dimethylformamide. Further preferred as a solvent is a mixture of the suitable solvent with the amine base. When the solvent comprises the amine base or a combination of the amine base and the suitable solvent, the amine base is typically in large stoichiometric excess relative to the compound of Formula 2.

In step 2 of Scheme 15, removal of the trimethylsilane group to give an alkyne of Formula 25 is achieved by treating a compound Formula 24 with an alkali metal hydroxide or carbonate such as potassium hydroxide, sodium hydroxide or potassium carbonate in methanol or ethanol. Typically the mole ratio of the base to the compound of Formula 24 is from about 0.001 to about 5. The reaction is preferably conducted in a suitable organic solvent. Typically, the method is most satisfactorily conducted at a temperature ranging from about 0° C. to the reflux temperature of the solvent, and most preferably from about 25 to 30° C. Alternatively, other disilylating conditions known in the art can be used, such as treatment with tetrabutylammonium fluoride in solvents such as tetrahydrofuran and chloroform (optimally comprising water).

In step 3 of Scheme 15, compounds of Formula 23 are prepared by reacting alkynes of Formula 25 with a suitable source of azide ions and in the presence of at least one copper (I) salt. Suitable azide sources include, for example, sodium azide and trimethylsilyl azide. The mole ratio of the azide source relative to the compound of Formula 25 is typically from about 1 to about 3. In the present method, suitable copper(I) salts comprise one or more compounds selected from the group consisting of copper(I) iodide, copper(I) bromide and copper(I) chloride. Alternatively, a copper(II) salt can be used in combination with a mild reducing agent, for example copper(II) sulfate with sodium ascorbate. The mole ratio of the copper(I) salt to the compound of Formula 25 is typically from about 0.05 to about 0.2. The reaction is typically run in a solvent such as N,N-dimethylformamide, tetrahydrofuran, methanol, tert-butanol, dimethyl sulfoxide (optionally comprising water), at temperatures from about 25 to 100° C. The use of lower boiling solvents can in some cases necessitate the need for elevated pressure to facilitate running the reaction at temperatures higher then the normal boiling point of the solvent. For leading references describing the method of step 3 of Scheme 15 see Jin et al., *European J. Organic Chem.* 2004, 3789-3791; Anderson et al., *Synlett* 2005, 2941-2947; and Weinreb et al., *Tetrahedron Letters* 2006, 47, 3035-3038.

Scheme 15

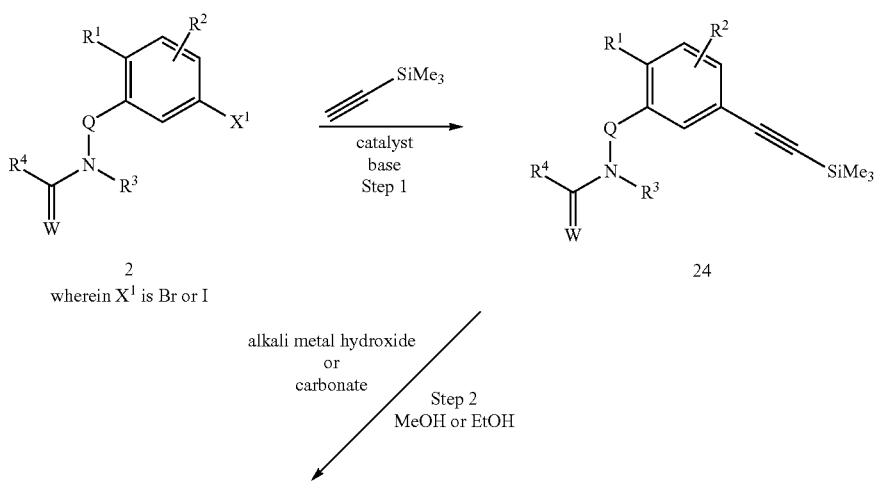

As shown in Scheme 16 compounds of Formula 1d (Formula 1 wherein Y is Y-13 and Z is one of the heterocycles listed in Exhibit 2B) can be prepared from a compound of Formula 26. Compounds of Formula 26 can be prepared by brominating a compound of Formula 27 using a brominating agent such as N-bromosuccinimide (NBS) or bromine Bromination methods of this type are well documented in the chemical literature. For leading references see, for example, Song et al., *Synthetic Communications* 2007, 37(19), 3311-3317; Andrus et al., *Organic Letters* 2007, 9(23), 4865-4868; *Organic & Biomolecular Chemistry* 2007, 5(16), 2555-2559; Piazzi et al., *Journal of Medicinal Chemistry* 2007, 50(17), 4250-4254 and Zhao et al., *Journal of Agricultural and Food Chemistry* 2007, 55(14), 5697-5700. Also, U.S. Pat. No. 6,313,071 provides an example relevant to the bromination method of Scheme 16.

In the second step, treatment of the benzyl bromide of Formula 26 with potassium cyanate or sodium cyanate and a compound of Formula $R^4H$ wherein $R^4$ is an alkoxy or alkylamino group provides compounds of Formula 1d. The reaction is typically carried out in a solvent such as N,N-dimethylformamide at temperatures ranging from about room temperature to 100° C. according to the procedure described in U.S. Pat. No. 6,313,071.

Compounds of Formula 27 are either commercially available or can be prepared by known methods. As illustrated in Scheme 17, compounds of Formula 27 can be prepared by treating a compound of Formula 28 with an oxidizing agent such as hydrogen peroxide or silver carbonate according to the procedures taught by Paulvannan et al., *Tetrahedron* 2000, 56(41), 8071-8076 and Buzykin et al., *Synthesis* 1993, (1), 59-61.

As shown in Scheme 18, a compound of Formula 28 can be prepared by reacting a compound of Formula 29 with methylamine or 2,2-diphenylethylamine according to the procedure given in Paulvannan et al., *Tetrahedron* 2000, 56(41), 8071-8076 and Buzykin et al., *Synthesis* 1993, (1) 59-61.

Scheme 18

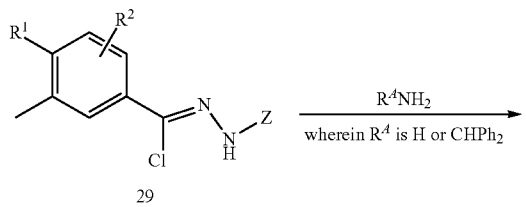

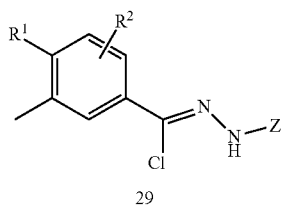

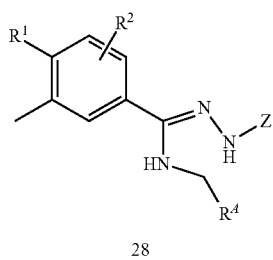

In the method of Scheme 19, a compound of Formula 29 is prepared by first reacting a an aldehyde of Formula 30 with a hydrazine of Formula 31 to provide the intermediate compound of Formula 32. For leading references teaching this method see *Tetrahedron* 2000, 56(41), 8071-8076; Lebedev et al., *J. Organic Chemistry* 2005, 70(2), 596-602 and Halley et al., *Synthetic Communications* 1997, 27(7), 1199-1207. In a subsequent step the compound of Formula 32 is chlorinated using a chlorinating agent such N-chlorosuccinimide (NCS). For references relevant to this type of chlorination see Paulvannan et al., *Tetrahedron* 2000, 56(41), 8071-8076; Patel et al., *Tetrahedron* 1996, 52(2), 661-668 and Chen et al., *Chemistry Letters* 1998 (2), 285-288. Compounds of Formula 30 can be prepared by methods well documented in the chemistry art, and many are commercially available. Compounds of Formula 31 can be prepared from compounds of Formula 14 using known literature methods. For references teaching aryl hydrazine preparation see U.S. Patent Application Publication US 2005/0137226 and World Patent Publication WO 2006/066937.

Scheme 19

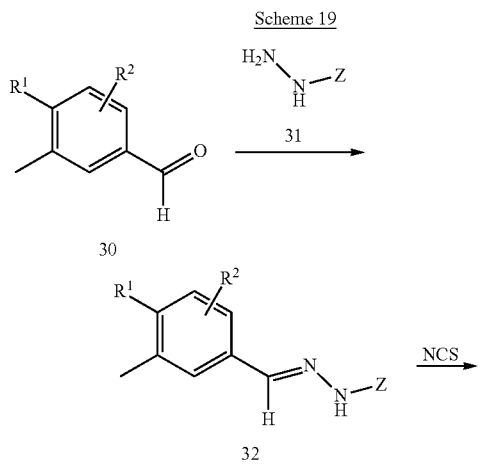

Additionally, one skilled in the art will recognize that compounds of Formula 1 wherein W is O can be converted to the corresponding thioamides wherein W is S using a variety of standard thiating reagents such as phosphorus pentasulfide or 2,4-bis(4-methoxyphenyl)-1,3-dithia-2,4-diphosphetane-2,4-disulfide (Lawesson's reagent).

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1.

One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Steps in the following Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. Copper(1) iodide used in the examples was 99.999% pure (trace metal basis) and purchased from Aldrich or Strem Chemicals. $^1$H NMR spectra are reported in ppm downfield from tetramethylsilane; "s" means singlet, "d" means doublet, "t" means triplet, "q" means quartet, "m" means multiplet, "dd" means doublet of doublets, "dt" means doublet of triplets, "br s" means broad singlet and "b" means a broad signal.

Synthesis Example 1

Preparation of methyl N-[[2-chloro-5-[3-(3,4-dihydro-2H-1-benzopyran-6-yl)-1H-pyrazol-1-yl]phenyl]methyl]carbamate (Compound 5)

Step A: Preparation of 3-(3,4-dihydro-2H-1-benzopyran-6-yl)-1H-pyrazole

To a solution of B-(1H-pyrazol-3-yl)boronic acid (400 mg, 3.57 mmol) in a mixture of tetrahydrofuran (THF), 1,2-dimethoxyethane and water (1:2:1), was added 3,4-dihydro-6-iodo-2H-1-benzopyran (1.53 g, 5.88 mmol; prepared according to Muraki et al., *Tetrahedron Lett.* 1996, 37, 2441) under nitrogen atmosphere. Then potassium carbonate (980 mg, 7.14 mmol) and bis(triphenylphosphine)palladium(II) dichloride (120 mg, 0.017 mmol) were added, and the reaction mixture was heated at 90° C. for 3 h. The reaction mixture was concentrated and purified by silica gel column chromatography using 30% ethyl acetate in petroleum ether as eluant to provide the title product as solid (100 mg).

$^1$H NMR (CDCl$_3$) δ 2.1 (m, 2H), 2.8 (m, 2H), 4.2 (m, 2H), 6.5 (d, 1H), 6.8 (m, 1H), 7.4 (m, 2H), 7.6 (m, 1H).

Step B: Preparation of methyl N-[[2-chloro-5-[3-(3,4-dihydro-2H-1-benzopyran-6-yl)-1H-pyrazol-1-yl]phenyl]methyl]carbamate To a solution of 3-(3,4-dihydro-2H-1-benzopyran-6-yl)-1H-pyrazole (i.e. the product of Step A) (600 mg, 3 mmol) in dioxane (50 mL) under nitrogen atmosphere, was added trans-N,N'-dimethylcyclohexane-1,2-diamine (86 mg, 0.6 mmol), followed by the addition of copper(I) iodide (114 mg, 0.6 mmol) and potassium carbonate (2.48 g, 18 mmol) to form a dark green-colored reaction mixture. To this reaction mixture was added methyl N-[(5-bromo-2-chlorophenyl)methyl]carbamate (1.2 g, 4.5 mmol; prepared according to U.S. Pat. No. 6,313,071), and the reaction mixture was heated at 95° C. under nitrogen overnight. The reaction mixture was then concentrated and purified by silica gel column chromatography using 20% ethyl acetate in petroleum ether as eluant to provide the title product, a compound of the present invention, as a solid (110 mg).

$^1$H NMR (CDCl$_3$) δ 1.95 (t, 2H), 2.8 (m, 2H), 3.6 (s, 3H), 4.18 (m, 2H), 4.35 (d, 2H), 6.8 (d, 1H), 6.95 (d, 1H), 7.6 (m, 3H), 7.8 (m, 2H), 7.9 (d, 1H), 8.5 (d, 1H).

Synthesis Example 2

Preparation of N-[[2-chloro-5-[3-(3,4-dihydro-2H-1-benzopyran-6-yl)-1H-pyrazol-1-yl]phenyl]methyl]acetamide (Compound 8)

Step A: Preparation of 5-bromo-2-chlorobenzenemethanamine

To a solution of chlorotrimethylsilane (3.55 mL, 27.2 mmol) in acetonitrile (70 mL) was added sodium iodide (3.91 g, 27.2 mmol), and the reaction mixture was stirred at −20° C. for 1 h. Then methyl N-[(5-bromo-2-chlorophenyl)methyl]carbamate (3 g, 7.7 mmol; prepared according to U.S. Pat. No. 6,313,071) was added, and the reaction mixture was stirred at room temperature for 16 h. The reaction mixture was then basified with 1 N aqueous sodium hydroxide solution and extracted with ethyl acetate (3×). The organic layers were combined, washed with water and brine and then dried (Na$_2$SO$_4$). The solvent was evaporated to provide the title product (1.4 g).

$^1$H NMR (CDCl$_3$) δ 3.9 (s, 2H), 7.22 (m, 1H), 7.32 (m, 1H), 7.56 (m, 1H).

Step B: Preparation of N-[(5-bromo-2-chlorophenyl)methyl]acetamide

To a solution of 5-bromo-2-chlorobenzenemethanamine (i.e. the product of Step A) (600 mg, 2.72 mmol) in toluene (10 mL) at 0° C. was added acetic anhydride (0.55 mL, 5.45 mmol). The reaction mixture was stirred at 100° C. for 3 h. The reaction mixture was then extracted with ethyl acetate (3×), and the organic layers were combined, washed with water and brine and dried (Na$_2$SO$_4$). The solvent was evaporated to provide the title product (600 mg).

$^1$H NMR (CDCl$_3$) δ 1.9 (s, 3H), 4.3 (d, 2H), 7.4 (d, 1H), 7.5 (m, 2H), 8.4 (m, 1H).

Step C: Preparation of N-[[2-chloro-5-[3-(3,4-dihydro-2H-1-benzopyran-6-yl)-1H-pyrazol-1-yl]phenyl]methyl]acetamide N-[(5-bromo-2-chlorophenyl)methyl]acetamide (i.e. the product of Step B) (0.58 g, 2.2 mmol) was reacted with 3-(3,4-dihydro-2H-1-benzopyran-6-yl)-1H-pyrazole (i.e. the product of Step A of Synthesis Example 1) (0.40 g, 2.0 mmol) using a procedure analogous to Step B of Synthesis Example 1 to provide the title product, a compound of the present invention, as a solid (0.09 g).

$^1$H NMR (CDCl$_3$) δ 1.95 (t, 2H), 1.97 (s, 3H), 2.81 (m, 2H), 4.15 (m, 2H), 4.32 (d, 2H), 6.8 (d, 1H), 6.94 (d, 1H), 7.6 (m, 3H), 7.8 (m, 1H), 7.85 (m, 1H), 8.4 (m, 1H), 8.5 (m, 1H).

Synthesis Example 3

Preparation of N-[[2-chloro-5-[3-(3,4-dihydro-2H-1-benzopyran-6-yl)-1H-pyrazol-1-yl]phenyl]methyl]-N'-methylurea (Compound 9)

Step A: Preparation of N-[(5-bromo-2-chlorophenyl)methyl]-N'-methylurea

To a solution of 5-bromo-2-chlorobenzenemethanamine (i.e. the product of Synthesis Example 2, Step A) (1.3 g, 5.5 mmol) in dichloromethane (25 mL) at 0° C. was added carbonyl diimidazole (1.4 g, 8.6 mmol). The reaction mixture was stirred at room temperature for 1 h. Then the reaction mixture was cooled to 0° C., a solution of methylamine in THF (2 M, 3.0 mL, 6.0 mmol) was added, and the reaction mixture was stirred at room temperature for 4 h. The reaction mixture was filtered, and the solid residue was washed with pentane to provide the title product (1.0 g).

$^1$H NMR (CDCl$_3$) δ 2.6 (d, 3H), 4.2 (d, 2H), 6 (m, 1H), 6.5 (m, 1H), 7.4 (d, 1H), 7.44 (m, 2H).

Step B: Preparation of N-[[2-chloro-5-[3-(3,4-dihydro-2H-1-benzopyran-6-yl)-1H-pyrazol-1-yl]phenyl]methyl]-N'-methylurea N-[(5-bromo-2-chlorophenyl)methyl]-N'-methylurea (i.e. the product of Step A) (0.61 g, 2.2 mmol) was reacted with 3-(3,4-dihydro-2H-1-benzopyran-6-yl)-1H-pyrazole (i.e. the product of Step A of Synthesis Example 1) (0.40 g, 2.0 mmol)

using a procedure analogous to Step B of Synthesis Example 1 to provide the title product, a compound of the present invention, as a solid (0.03 g).

$^1$H NMR (CDCl$_3$) δ 1.96 (m, 2H), 2.6 (s, 3H), 2.82 (m, 2H), 4.16 (m, 2H), 4.35 (d, 2H), 6.0 (t, 1H), 6.5 (m, 1H), 6.8 (d, 1H), 6.94 (m, 1H), 7.6 (m, 3H), 7.74 (m, 1H), 7.9 (m, 1H), 8.45 (d, 1H).

Synthesis Example 4

Preparation of N-[[2-chloro-5-[1-(3,4-dihydro-2H-1-benzopyran-6-yl)-1H-pyrazol-3-yl]-phenyl]methyl]formamide (Compound 3)

Step A: Preparation of N-[[2-chloro-5-[3-(dimethylamino)-1-oxo-2-propen-1-yl]-phenyl]methyl]acetamide A mixture of N-[(5-acetyl-2-chlorophenyl)methyl]acetamide (13.0 g, 57.8 mmol; prepared according to a procedure described in EP 1586552-A1) and N,N-dimethylformamide dimethyl acetal (13.8 g, 115.8 mmol) in toluene (130 mL) was heated at 105° C. overnight. The reaction mixture was then concentrated, and the resulting solid was washed with diethyl ether and n-pentane to yield the title product as a solid (10.0 g).

$^1$H NMR (DMSO-d$_6$) δ 2.0 (s, 3H), 2.9 (s, 3H), 3.2 (s, 3H), 4.5 (d, 2H), 5.6 (d, 2H), 6.0 (m, 1H), 7.4 (d, 1H), 7.88 (m, 2H).

Step B: Preparation of N-[[2-chloro-5-(1H-pyrazol-3-yl)phenyl]methyl]acetamide

A mixture of N-[[2-chloro-5-[3-(dimethylamino)-1-oxo-2-propen-1-yl]phenyl]methyl]-acetamide (i.e. the product of Step A) (10.0 g, 35.7 mmol) and hydrazine hydrate (2.6 mL, 53.6 mmol) in methanol (100 mL) was stirred at room temperature for 20 h. The reaction mixture was then cooled to −5° C. and filtered, resulting in the title product as a solid (2.0 g), which was used in the next step without purification.

$^1$H NMR (DMSO-d$_6$) δ 1.9 (s, 3H), 4.3 (s, 2H), 6.7 (s, 1H), 7.44 (d, 1H), 7.72 (d, 1H), 7.82 (m, 1H), 8.4 (m, 2H), 12.8 (b, 1H).

Step C: Preparation of 2-chloro-5-(1H-pyrazol-3-yl)benzenemethanamine

A mixture of N-[[2-chloro-5-(1H-pyrazol-3-yl)phenyl]methyl]acetamide (i.e. the product of Step B) (2.0 g, 8.0 mmol), sulfuric acid (1.5 mL) and water (7.0 mL) was heated to 120° C. for 15 h. The reaction mixture was then cooled to ambient temperature, basified with 10% NaOH solution and extracted with ethyl acetate. The combined extracts were washed with brine, dried (Na$_2$SO$_4$) and concentrated to yield the title product as a solid (1.0 g), which was used in the next step without further purification.

$^1$H NMR (DMSO-d$_6$) δ 1.9 (b, 2H), 3.8 (d, 2H), 6.7 (s, 1H), 7.4 (d, 1H), 7.6 (d, 1H), 7.7 (b, 1H), 8.0 (s, 1H), 13.0 (b, 1H).

Step D: Preparation of N-[[2-chloro-5-(1H-pyrazol-3-yl)phenyl]methyl]formamide

A mixture of acetic anhydride (0.82 mL, 9.7 mmol) and formic acid (0.4 mL, 9.7 mmol) was heated to 50° C. for 30 minutes and then cooled to 0° C. 2-Chloro-5-(1H-pyrazol-3-yl)benzenemethanamine (i.e. the product of Step C) (1.0 g, 4.8 mmol) was added, and the reaction mixture was stirred at ambient temperature for 4 h. The reaction mixture was then diluted with dichloromethane, washed with saturated sodium bicarbonate solution and brine, then dried (Na$_2$SO$_4$) and concentrated. The crude residue was purified by preparative thin layer chromatography (TLC) (2% methanol in chloroform as eluant) to provide the title product as a solid (0.5 g).

$^1$H NMR (DMSO-d$_6$) δ 4.4 (d, 2H), 6.7 (s, 1H), 7.4 (d, 2H), 7.8 (d, 2H), 8.2 (s, 1H), 8.6 (m, 1H) 12.9 (b, 1H).

Step E: Preparation of N-[[2-chloro-5-[1-(3,4-dihydro-2H-1-benzopyran-6-yl)-1H-pyrazol-3-yl]phenyl]methyl]formamide To a solution of N-[[2-chloro-5-(1H-pyrazol-3-yl)phenyl]methyl]formamide (i.e. the product of Step D) (0.25 g, 1.1 mmol) in dioxane (2.5 mL) was added trans-N,N'-dimethylcyclohexane-1,2-diamine (0.06 mL, 0.43 mmol) followed copper(I) iodide (0.08 g, 0.43 mmol), potassium carbonate (0.87 g, 6.4 mmol) and 3,4-dihydro-6-iodo-2H-1-benzopyran (0.45 g, 1.7 mmol; prepared according to the procedure of Muraki et al., *Tetrahedron Lett.* 1996, 37, 2441). The reaction mixture was heated at 110° C. for 20 h and then cooled to ambient temperature. The solvent was evaporated, and the residue was taken up in chloroform, washed with water and brine, then dried (Na$_2$SO$_4$) and concentrated. The crude residue was then purified by preparative TLC (2% methanol in chloroform as eluant) to provide the title product, a compound of the present invention, as a solid (0.069 g).

$^1$H NMR (DMSO-d$_6$) δ 8.63 (m, 1H), 8.43 (d, 1H), 8.22 (d, 1H), 7.92 (d, 1H), 7.82 (dd, 1H), 7.51 (dd, 1H), 7.62 (dd, 2H), 7.0 (d, 1H), 6.85 (dd, 1H), 4.5 (d, 2H), 4.2 (d, 2H), 2.82 (m, 2H), 1.97 (m, 2H).

Synthesis Example 5

Preparation of N-[[2-chloro-5-[1-(3,4-dihydro-2H-1-benzopyran-6-yl)-1H-pyrazol-3-yl]-phenyl]methyl]-N'-methylurea (Compound 4)

Step A: Preparation of N-[[2-chloro-5-(1H-pyrazol-3-yl)phenyl]methyl]-N'-methylurea To a solution of 2-chloro-5-(1H-pyrazol-3-yl)benzenemethanamine (i.e. the product of Step C of Synthesis Example 4) (2.4 g, 11.6 mmol) in THF (12 mL) and dichloromethane (12 mL) at 10° C. was added carbonyl diimidazole (2.8 g, 17.3 mmol). The reaction mixture was stirred at ambient temperature for 30 minutes and then cooled to 0° C. A solution of methylamine in THF (2 M, 12.0 mL, 24 mmol) was added, and the reaction mixture was stirred at ambient temperature for 15 h. The reaction mixture was then diluted with dichloromethane, washed with water and brine, concentrated and purified by preparative TLC (2% methanol in chloroform as eluant) to provide the title product as a solid (1.0 g).

$^1$H NMR (DMSO-d$_6$) δ 2.6 (s, 3H), 4.2 (d, 2H), 5.9 (m, 1H), 6.4 (m, 1H), 6.7 (s, 1H), 7.4 (d, 1H), 7.7 (d, 1H), 7.84 (d, 1H), 7.91 (d, 1H), 12.9 (m, 1H).

Step B: Preparation of N-[[2-chloro-5-[1-(3,4-dihydro-2H-1-benzopyran-6-yl)-1H-pyrazol-3-yl]phenyl]methyl]-N'-methylurea To a solution of N-[[2-chloro-5-(1H-pyrazol-3-yl)phenyl]methyl]-N'-methylurea (i.e. the product of Step A) (0.30 g, 1.1 mmol) in dioxane (3.0 mL) was added trans-N,N'-dimethylcyclohexane-1,2-diamine (0.07 mL, 0.45 mmol) followed by copper(I) iodide (0.085 g, 0.45 mmol), potassium carbonate (0.94 g, 6.8 mmol) and 3,4-dihydro-6-iodo-2H-1- benzopyran (0.44 g, 1.7 mmol; prepared as cited in Step E of Synthesis Example 4). The reaction mixture was heated to 110° C. for 20 h and then cooled to ambient temperature. The solvent was evaporated, and the residue was taken up in chloroform, washed with water and brine, and then dried ($Na_2SO_4$) and concentrated. The crude residue was purified by preparative TLC (1.5% methanol in dichloromethane as eluant) to provide the title product a compound of the present invention, as a solid (0.036 g).

$^1$H NMR (DMSO-$d_6$) δ 8.42 (m, 1H), 7.94 (d, 1H), 7.8 (d, 1H), 7.6 (m, 2H), 7.52 (d, 1H), 6.84 (dd, 1H), 6.92 (d, 1H), 6.51 (d, 1H), 5.9 (d, 1H), 4.4 (d, 2H), 4.2 (d, 2H), 2.85 (d, 2H), 2.6 (d, 3H), 1.98 (d, 2H).

Synthesis Example 6

Preparation of N-[[2-chloro-5-[1-(3,4-dihydro-2H-1-benzopyran-6-yl)-1H-pyrazol-3-yl]-phenyl]methyl] acetamide (Compound 2)

To a solution of N-[[2-chloro-5-(1H-pyrazol-3-yl)phenyl] methyl]acetamide (i.e. the product of Step B of Synthesis Example 4) (0.25 g, 1.0 mmol) in dioxane (2.5 mL) was added trans-N,N'-dimethylcyclohexane-1,2-diamine (0.065 mL, 0.40 mmol), followed by copper(I) iodide (0.076 g, 0.40 mmol), potassium carbonate (0.83 g, 6.0 mmol) and 3,4-dihydro-6-iodo-2H-1-benzopyran (0.20 g, 0.77 mmol; prepared as cited in Step E of Synthesis Example 4). The reaction mixture was heated at 110° C. for 20 h and then cooled to ambient temperature. The solvent was evaporated, and the residue was taken up in chloroform, washed with water and brine, and then dried ($Na_2SO_4$) and concentrated. The crude residue was purified by preparative TLC (2.0% methanol in dichloromethane as eluant) to provide the title product, a compound of the present invention, as a solid (0.11 g).

$^1$H NMR (DMSO-$d_6$) δ 8.3 (d, 2H), 7.83 (d, 1H), 7.72 (dd, 1H), 7.6 (m, H), 7.48 (dd, 1H), 6.98 (d, 1H), 6.82 (dd, 1H), 4.4 (d, 2H), 4.2 (d, 2H), 2.85 (d, 2H), 1.98 (m, 5H).

Synthesis Example 7

Preparation of methyl N-[[2-chloro-5-[1-(3,4-dihydro-2H-1-benzopyran-6-yl)-1H-pyrazol-3-yl]phenyl] methyl]carbamate (Compound 1)

To a solution of methyl N-[[(2-chloro-5-(1H-pyrazol-3-yl) phenyl]methyl]carbamate (prepared according to a procedure described in World Patent Publication WO 2008/124092) (600 mg, 2.2 mmol) in dioxane (60 mL) was added trans-N, N'-dimethylcyclohexane-1,2-diamine (60 mg, 0.452 mmol) under nitrogen atmosphere. Then copper(I) iodide (86 mg, 0.452 mmol) and potassium carbonate (1.87 g, 13.5 mmol) were added to form a dark-green-colored reaction mixture. To the reaction mixture was added 3,4-dihydro-6-iodo-2H-1-benzopyran (882 mg, 3.39 mmol). The reaction mixture was heated at 95° C. under nitrogen overnight, the solvent was evaporated, and the residue was purified by silica gel column chromatography (30% ethyl acetate/petroleum ether as eluant) to provide the title product, a compound of the present invention, as solid (0.318 g).

$^1$H NMR (CDCl$_3$) δ 1.9 (m, 2H), 2.9 (m, 2H), 3.6 (s, 3H), 4.2 (m, 2H), 4.3 (d, 2H), 6.8 (d, 1H), 7.0 (s, 1H), 7.5 (d, 1H), 7.6 (m, 2H), 7.8 (m, 2H), 7.9 (s, 1H), 8.4 (s, 1H).

Synthesis Example 8

Preparation of methyl 6-[3-[4-chloro-3-[[(methoxycarbonyl)amino]methyl]phenyl]-1H-pyrazol-1-yl]-2H-1-benzopyran-3-carboxylate (Compound 23) and 6-[3-[4-chloro-3-[[(methoxycarbonyl)amino]methyl] phenyl]-1H-pyrazol-1-yl]-2H-1-benzopyran-3-carboxylic acid (Compound 24)

Step A: Preparation of methyl N-[[2-chloro-5-[3-(dimethylamino)-1-oxo-2-propen-1-yl]phenyl]methyl]carbamate To a solution of methyl N-[(5-acetyl-2-chlorophenyl)methyl]carbamate (10 g, 41.5 mmol) (prepared by the method given in European Patent Publication EP 1586552) in toluene was added N,N-dimethylformamide dimethyl acetal (9.88 g, 82.9 mmol) and the reaction mixture was heated at 135° C. for 2 days. TLC analysis (50% ethyl acetate/pet ether) showed the reaction was complete. The solvent was evaporated under vacuum and water was added to the residue. The water layer was extracted with ethyl acetate three times. The combined the organic phases were washed with water, brine, dried over $Na_2SO_4$ and concentrated under vacuum to give the title compound (10 g, 81% yield) as solid.

$^1$H NMR (DMSO-$d_6$) δ 2.9 (s, 3H), 3.2 (s, 3H), 3.6 (s, 3H), 4.3 (d, 2H), 5.9 (d, 1H), 7.5 (m, 1H), 7.8 (m, 4H).

Step B: Preparation of methyl N-[[2-chloro-5-(1H-pyrazol-3-yl)phenyl]-methyl]carbamate To a solution of methyl N-[[2-chloro-5-[3-(dimethylamino)-1-oxo-2-propen-1-yl]phenyl]methyl]carbamate (i.e. the product of Step A) (10 g, 33.78 mmol) in methanol (100 mL) was added hydrazine hydrate (1.08 mL, 33.78 mmol) and the reaction mixture was stirred at ambient temperature for 2 days. After TLC analysis (10% MeOH/CHCl$_3$) showed completion of the reaction, the reaction mixture was filtered was filtered. The resultant solid residue was washed with methanol and dried under vacuum to give the title compound (4 g, 48% yield) as solid.

$^1$H NMR (DMSO-$d_6$) δ 3.6 (s, 3H), 4.25 (d, 2H), 6.65 (s, 1H), 7.4-7.9 (m, 5H), 12.9 (s, 1H).

Step C: Preparation of methyl 6-[3-[4-chloro-3-[[(methoxycarbonyl)amino]-methyl]phenyl]-1H-pyrazol-1-yl]-2H-1-benzopyran-3-carboxylate To a solution of methyl N-[[2-chloro-5-(1H-pyrazol-3-yl) phenyl]-methyl]carbamate (i.e. the product of Step B) (400 mg, 1.50 mmol) in dioxane (16 mL) was added trans-N,N'-dimethylcyclohexane-1,2-diamine (0.30 mmol, 43 mg) under a nitrogen atmosphere. Copper (I) iodide (57 mg, 0.30 mmol) and K$_2$CO$_3$ (1.24 g, 9.05 mmol) were added to the reaction mixture. Methyl 6-bromo-2H-1-benzopyran-3-carboxylate (607 mg, 2.26 mmol) was added to the reaction mixture last. The reaction mixture was heated at 100° C. under a nitrogen atmosphere overnight. After TLC analysis (10% MeOH/ CHCl$_3$) showed 80% conversion of the starting material, the reaction mixture was cooled and concentrated under vacuum. The crude residue was purified on a silica gel column with 1% MeOH/CHCl$_3$ as eluent to give compound number 23, a compound of the present invention, (110 mg, 16% yield) as solid.

$^1$H NMR (DMSO-$d_6$) δ 3.6 (s, 3H), 3.8 (s, 3H), 4.3 (d, 2H), 5.0 (s, 2H), 7.0 (m, 2H), 7.5 (d, 1H), 7.6 (s, 1H), 7.8 (m, 3H), 7.9 (m, 2H), 8.4 (d, 1H).

Step D: Preparation of 6-[3-[4-chloro-3-[[(methoxycarbonyl)amino]methyl]phenyl]-1H-pyrazol-1-yl]-2H-1-benzopyran-3-carboxylic acid To a solution of methyl 6-[3-[4-chloro-3-[[(methoxycarbonyl)amino]methyl]phenyl]-1H-pyrazol-1-yl]-2H-1-benzopyran-3-carboxylate (i.e. the product of Step C) (100 mg, 0.22 mmol) in 1:1 tetrahydrofuran/water was added NaOH (35 mg 0.85 mmol) and the reaction mixture was stirred at ambient temperature for 6 hrs. After TLC analysis (50% ethyl acetate/pet ether) showed completion of reaction, the organic solvent was concentrated. The resultant aqueous solution was cooled to 0° C., acidified with 1N HCl and extracted three times with ethyl acetate. The combined the organic phases were washed with water, brine, dried over $Na_2SO_4$. The solvent was concentrated under vacuum to give compound number 24, a compound of the present invention, (70 mg, 73% yield) as solid.

$^1$H NMR (DMSO-$d_6$) δ 3.6 (s, 3H), 4.3 (d, 2H), 5.0 (s, 2H), 7.1 (m, 2H), 7.5 (m, 2H), 7.8 (m, 3H), 7.9 (m, 2H). 8.4 (d, 1H), 13.0 (bs, 1H).

Synthesis Example 9

Preparation of methyl N-[[2-chloro-5-(1-spiro[2H-1-benzopyran-3(4H), 2'-[1,3]dioxolan]-6-yl-1H-pyrazol-3-yl)phenyl]methyl]carbamate (Compound 28)

Step A: Preparation of 6-bromospiro[2H-1-benzopyran-3(4H), 2'-[1,3]dioxolane]

To a solution of 6-bromo-2H-1-benzopyran-3(4H)-one (300 mg, 1.13 mmol) in toluene (2 mL) was added ethyleneglycol (163 mg 2.64 mmol) and para-toluenesulfonic acid (27 mg, 0.13 mmol). The reaction mixture was heated at 100° C. for 6 hrs. The reaction mixture was cooled and the solvent concentrated. The resultant residue was partitioned between ethyl acetate and water. The organic phase was washed with water, brine, dried over $Na_2SO_4$ and concentrated under vacuum to give the title compound (290 mg, 79% yield) as a solid.

$^1$H NMR (CDCl$_3$) δ 3.0 (s, 2H), 3.9 (s, 2H), 4.1 (d, 4H), 6.8 (m, 1H), 7.2 (m, 2H).

Step B Preparation of methyl N-[[2-chloro-5-(1-spiro[2H-1-benzopyran-3(4H), 2'-[1,3]dioxolan]-6-yl-1H-pyrazol-3-yl)phenyl]methyl]carbamate To a solution of methyl N-[[2-chloro-5-(1H-pyrazol-3-yl)phenyl]-methyl]carbamate (i.e. the product of Example 8, Step B) (400 mg, 1.50 mmol) in dioxane (16 mL) was added trans-N,N'-dimethylcyclohexane-1,2-diamine (0.30 mmol, 43 mg) under a nitrogen atmosphere. Copper (I) iodide (57 mg, 0.30 mmol) and potassium carbonate (1.24 g, 9.05 mmol) were added to the reaction mixture. 6-Bromospiro[2H-1-benzopyran-3(4H),2'-[1,3]dioxolane] (614 mg, 2.26 mmol) was added last and the reaction mixture was heated at 100° C. under a nitrogen atmosphere overnight. After TLC analysis (10% MeOH/CHCl$_3$) shows 80% conversion of starting material, the reaction mixture was concentrated under vacuum. The resultant crude residue was purified on a silica gel column with 1% MeOH/CHCl$_3$ as eluent to give the title compound, a compound of the present invention, (120 mg, 18% yield) as a solid.

$^1$H NMR (CDCl$_3$) δ 3.1 (s, 2H), 3.7 (s, 3H), 4.0 (s, 2H), 4.1 (m, 4H), 4.4 (d, 2H), 5.2 (bs, 1H), 6.7 (m, 1H), 7.0 (d, 1H), 7.4 (m, 3H), 7.76 (dd, 1H), 7.8 (d, 1H), 7.9 (bs, 1H).

Synthesis Example 10

Preparation of methyl N-[[2-chloro-5-[1-(3,4-dihydro-3-oxo-2H-1-benzopyran-6-yl)-1H-pyrazol-3-yl]phenyl]methyl]carbamate (Compound 29)

To a solution of methyl N-[[2-chloro-5-(1-spiro[2H-1-benzopyran-3(4H), 2'-[1,3]dioxolan]-6-yl-1H-pyrazol-3-yl)phenyl]methyl]carbamate (i.e. the product of Example 9, Step B) (150 mg, 0.32 mmol) in acetone (15 mL) was added 3N HCl (4.5 mL). The reaction mixture was heated at 85° C. for 16 hrs when TLC analysis (50% ethyl acetate/pet ether) showed completion of reaction. The reaction mixture was cooled and the solvent was concentrated under vacuum. The resultant residue was partitioned between water and ethyl acetate. The organic phase was washed with water, brine, dried over $Na_2SO_4$ and concentrated under vacuum to give the title compound, a compound of the present invention, (90 mg, 68% yield) as a solid.

$^1$H NMR (CDCl$_3$) δ 3.7 (s, 5H), 4.5 (s, 2H), 4.6 (d, 2H), 5.2 (b, 1H), 6.7 (d, 1H), 7.2 (m, 1H), 7.4 (d, 1H), 7.6 (m, 2H), 7.8 (m, 1H), 7.9 (m, 2H).

Synthesis Example 11

Preparation of methyl N-[[2-chloro-5-[1-(3,4-dihydro-3-hydroxy-2H-1-benzopyran-6-yl)-1H-pyrazol-3-yl]phenyl]methyl]carbamate (Compound 30)

To a solution of methyl N-[[2-chloro-5-[1-(3,4-dihydro-3-oxo-2H-1-benzopyran-6-yl)-1H-pyrazol-3-yl]phenyl]methyl]carbamate (i.e. the product of Example 10) (100 mg, 0.24 mmol) in methanol (10 mL) was added sodium borohydride (19 mg, 0.48 mmol) and the reaction mixture was stirred at ambient temperature for 1 hour. After TLC analysis (30% ethyl acetate/pet ether) showed completion of reaction, the solvent was concentrated under vacuum. The crude residue was cooled to 0° C. and acidified with 1N HCl. The aqueous mixture was extracted three times with ethyl acetate. The combined the organic phases were washed with water, brine and dried over $Na_2SO_4$. The solvent was concentrated under vacuum to give the title compound, a compound of the present invention, (60 mg, 60% yield) as a solid.

$^1$H NMR (CDCl$_3$) δ 2.9 (dd, 1H), 3.2 (dd, 1H), 3.7 (s, 3H), 4.1 (s, 2H), 4.25 (m, 1H), 4.5 (d, 2H), 5.2 (b, 1H), 6.65 (d, 1H), 6.9 (d, 1H), 7.4 (m, 2H), 7.5 (m, 1H), 7.75 (m, 1H), 7.8 (d, 1H), 7.9 (bs, 1H).

By the procedures described herein together with methods known in the art, the following compounds of Tables 1 to 74G can be prepared. The following abbreviations are used in the Tables which follow: Me means methyl. The molecular fragments $Z^T$-1 through $Z^T$-47 are defined as depicted below wherein the bond extending from the left connects each fragment to the remainder of the molecule.

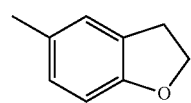

$Z^T$-1

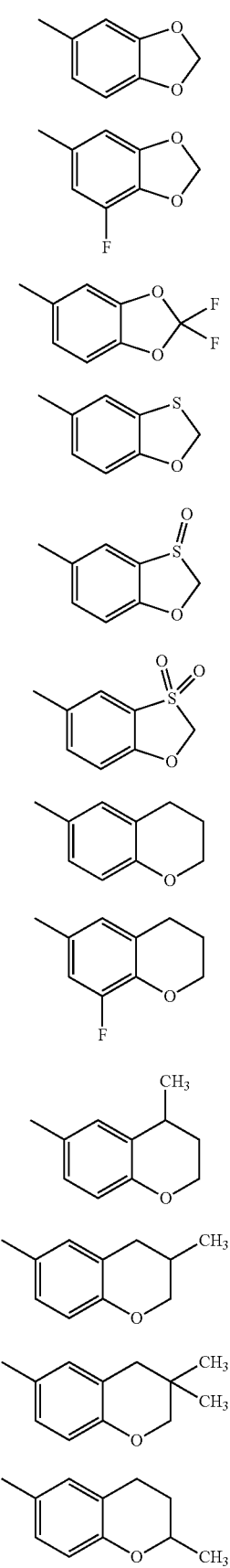
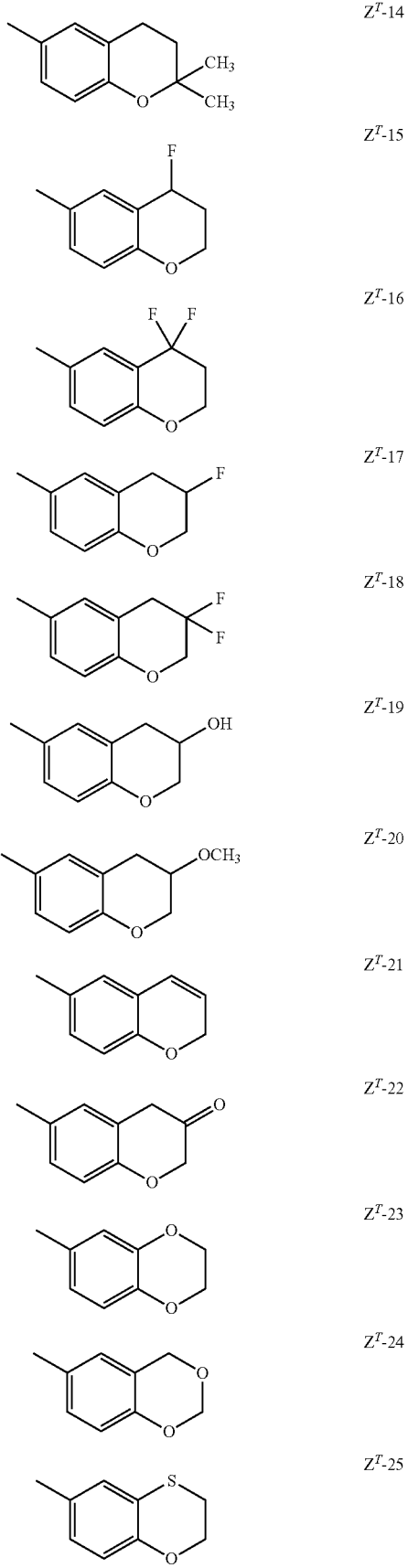

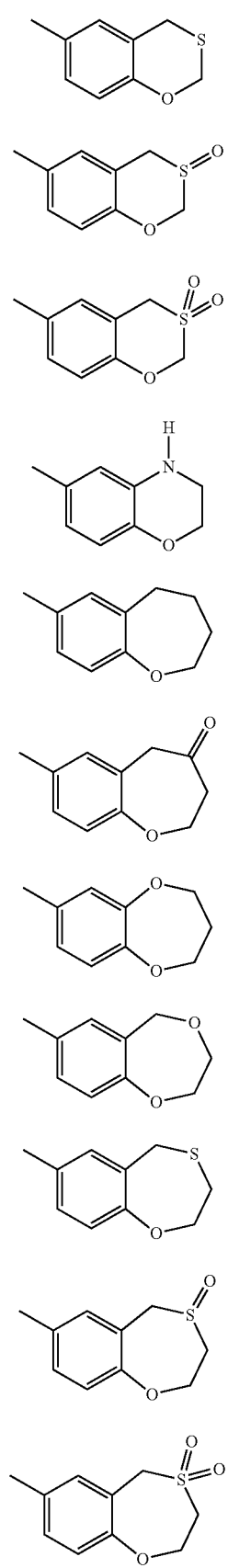

TABLE 1

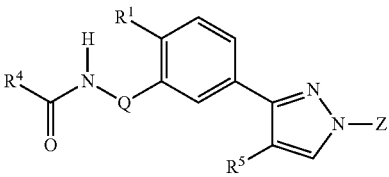

$R^1$ is Cl, $R^4$ is MeO, $R^5$ is H and Q is $CH_2$.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |
| $Z^T$-22 | $Z^T$-46 |
| $Z^T$-23 | $Z^T$-47 |
| $Z^T$-24 | |

The present disclosure also includes Tables 1A through 74A, each of which is constructed the same as Table 1 above except that the row heading in Table 1 (i.e. "$R^1$ is Cl, $R^4$ is MeO, $R^5$ is H and Q is $CH_2$.") below the Markush structure is replaced with the respective row heading shown below. For example, in Table 1A the row heading is "$R^1$ is F, $R^4$ is MeO, $R^5$ is H and Q is $CH_2$.", and Z is as defined in Table 1 above. Thus, the first entry in Table 1A specifically discloses methyl N-[[5-[1-(2,3-dihydro-5-benzofuranyl)-1H-pyrazol-3-yl]-2-fluorophenyl]methyl]carbamate. Tables 2A through 74A are constructed similarly.

| Table | Row Heading |
|---|---|
| 1A | $R^1$ is F, $R^4$ is MeO, $R^5$ is H and Q is $CH_2$. |
| 2A | $R^1$ is Me, $R^4$ is MeO, $R^5$ is H and Q is $CH_2$. |
| 3A | $R^1$ is CN, $R^4$ is MeO, $R^5$ is H and Q is $CH_2$. |
| 4A | $R^1$ is Cl, $R^4$ is MeO, $R^5$ is H and Q is NH. |
| 5A | $R^1$ is F, $R^4$ is MeO, $R^5$ is H and Q is NH. |
| 6A | $R^1$ is Me, $R^4$ is MeO, $R^5$ is H and Q is NH. |
| 7A | $R^1$ is CN, $R^4$ is MeO, $R^5$ is H and Q is NH. |
| 8A | $R^1$ is Cl, $R^4$ is MeO, $R^5$ is H and Q is O. |
| 9A | $R^1$ is F, $R^4$ is MeO, $R^5$ is H and Q is O. |
| 10A | $R^1$ is Me, $R^4$ is MeO, $R^5$ is H and Q is O. |
| 11A | $R^1$ is CN, $R^4$ is MeO, $R^5$ is H and Q is O. |
| 12A | $R^1$ is Cl, $R^4$ is MeHN, $R^5$ is H and Q is $CH_2$. |
| 13A | $R^1$ is F, $R^4$ is MeHN, $R^5$ is H and Q is $CH_2$. |
| 14A | $R^1$ is Me, $R^4$ is MeHN, $R^5$ is H and Q is $CH_2$. |
| 15A | $R^1$ is Cl, $R^4$ is MeHN, $R^5$ is H and Q is NH. |
| 16A | $R^1$ is F, $R^4$ is MeHN, $R^5$ is H and Q is NH. |
| 17A | $R^1$ is Me, $R^4$ is MeHN, $R^5$ is H and Q is NH. |
| 18A | $R^1$ is Cl, $R^4$ is MeHN, $R^5$ is H and Q is O. |
| 19A | $R^1$ is F, $R^4$ is MeHN, $R^5$ is H and Q is O. |
| 20A | $R^1$ is Me, $R^4$ is MeHN, $R^5$ is H and Q is O. |
| 21A | $R^1$ is Cl, $R^4$ is Me, $R^5$ is H and Q is $CH_2$. |
| 22A | $R^1$ is F, $R^4$ is Me, $R^5$ is H and Q is $CH_2$. |
| 23A | $R^1$ is Me, $R^4$ is Me, $R^5$ is H and Q is $CH_2$. |
| 24A | $R^1$ is Cl, $R^4$ is Me, $R^5$ is H and Q is NH. |
| 25A | $R^1$ is F, $R^4$ is Me, $R^5$ is H and Q is NH. |
| 26A | $R^1$ is Me, $R^4$ is Me, $R^5$ is H and Q is NH. |
| 27A | $R^1$ is Cl, $R^4$ is Me, $R^5$ is H and Q is O. |
| 28A | $R^1$ is F, $R^4$ is Me, $R^5$ is H and Q is O. |
| 29A | $R^1$ is Me, $R^4$ is Me, $R^5$ is H and Q is O. |
| 30A | $R^1$ is Cl, $R^4$ is H, $R^5$ is H and Q is $CH_2$. |
| 31A | $R^1$ is F, $R^4$ is H, $R^5$ is H and Q is $CH_2$. |
| 32A | $R^1$ is Me, $R^4$ is H, $R^5$ is H and Q is $CH_2$. |
| 33A | $R^1$ is Cl, $R^4$ is H, $R^5$ is H and Q is NH. |
| 34A | $R^1$ is F, $R^4$ is H, $R^5$ is H and Q is NH. |
| 35A | $R^1$ is Me, $R^4$ is H, $R^5$ is H and Q is NH. |
| 36A | $R^1$ is Cl, $R^4$ is H, $R^5$ is H and Q is O. |
| 37A | $R^1$ is F, $R^4$ is H, $R^5$ is H and Q is O. |
| 38A | $R^1$ is Me, $R^4$ is H, $R^5$ is H and Q is O. |
| 39A | $R^1$ is Cl, $R^4$ is MeO, $R^5$ is Me and Q is $CH_2$. |
| 40A | $R^1$ is F, $R^4$ is MeO, $R^5$ is Me and Q is $CH_2$. |
| 41A | $R^1$ is Me, $R^4$ is MeO, $R^5$ is Me and Q is $CH_2$. |
| 42A | $R^1$ is Cl, $R^4$ is MeO, $R^5$ is Me and Q is NH. |
| 43A | $R^1$ is F, $R^4$ is MeO, $R^5$ is Me and Q is NH. |
| 44A | $R^1$ is Me, $R^4$ is MeO, $R^5$ is Me and Q is NH. |
| 45A | $R^1$ is Cl, $R^4$ is MeO, $R^5$ is Me and Q is O. |
| 46A | $R^1$ is F, $R^4$ is MeO, $R^5$ is Me and Q is O. |
| 47A | $R^1$ is Me, $R^4$ is MeO, $R^5$ is Me and Q is O. |
| 48A | $R^1$ is Cl, $R^4$ is MeHN, $R^5$ is Me and Q is $CH_2$. |
| 49A | $R^1$ is F, $R^4$ is MeHN, $R^5$ is Me and Q is $CH_2$. |
| 50A | $R^1$ is Me, $R^4$ is MeHN, $R^5$ is Me and Q is $CH_2$. |
| 51A | $R^1$ is Cl, $R^4$ is MeHN, $R^5$ is Me and Q is NH. |
| 52A | $R^1$ is F, $R^4$ is MeHN, $R^5$ is Me and Q is NH. |
| 53A | $R^1$ is Me, $R^4$ is MeHN, $R^5$ is Me and Q is NH. |
| 54A | $R^1$ is Cl, $R^4$ is MeHN, $R^5$ is Me and Q is O. |
| 55A | $R^1$ is F, $R^4$ is MeHN, $R^5$ is Me and Q is O. |
| 56A | $R^1$ is Me, $R^4$ is MeHN, $R^5$ is Me and Q is O. |
| 57A | $R^1$ is Cl, $R^4$ is Me, $R^5$ is Me and Q is $CH_2$. |
| 58A | $R^1$ is F, $R^4$ is Me, $R^5$ is Me and Q is $CH_2$. |
| 59A | $R^1$ is Me, $R^4$ is Me, $R^5$ is Me and Q is $CH_2$. |
| 60A | $R^1$ is Cl, $R^4$ is Me, $R^5$ is Me and Q is NH. |
| 61A | $R^1$ is F, $R^4$ is Me, $R^5$ is Me and Q is NH. |
| 62A | $R^1$ is Me, $R^4$ is Me, $R^5$ is Me and Q is NH. |
| 63A | $R^1$ is Cl, $R^4$ is Me, $R^5$ is Me and Q is O. |
| 64A | $R^1$ is F, $R^4$ is Me, $R^5$ is Me and Q is O. |
| 65A | $R^1$ is Me, $R^4$ is Me, $R^5$ is Me and Q is O. |
| 66A | $R^1$ is Cl, $R^4$ is H, $R^5$ is Me and Q is $CH_2$. |
| 67A | $R^1$ is F, $R^4$ is H, $R^5$ is Me and Q is $CH_2$. |
| 68A | $R^1$ is Me, $R^4$ is H, $R^5$ is Me and Q is $CH_2$. |
| 69A | $R^1$ is Cl, $R^4$ is H, $R^5$ is Me and Q is NH. |
| 70A | $R^1$ is F, $R^4$ is H, $R^5$ is Me and Q is NH. |
| 71A | $R^1$ is Me, $R^4$ is H, $R^5$ is Me and Q is NH. |
| 72A | $R^1$ is Cl, $R^4$ is H, $R^5$ is Me and Q is O. |
| 73A | $R^1$ is F, $R^4$ is H, $R^5$ is Me and Q is O. |
| 74A | $R^1$ is Me, $R^4$ is H, $R^5$ is Me and Q is O. |

TABLE 2

$R^1$ is Cl, $R^4$ is MeO, $R^5$ is H and Q is $CH_2$.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |

TABLE 2-continued

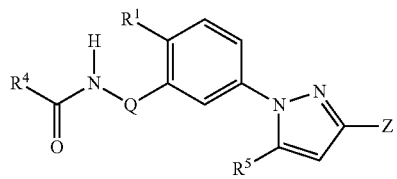

$R^1$ is Cl, $R^4$ is MeO, $R^5$ is H and Q is $CH_2$.

| Z | Z |
|---|---|
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |
| $Z^T$-22 | $Z^T$-46 |
| $Z^T$-23 | $Z^T$-47 |
| $Z^T$-24 | |

The present disclosure also includes Tables 1B through 74B, each of which is constructed the same as Table 2 above except that the row heading in Table 2 (i.e. "$R^1$ is Cl, $R^4$ is MeO, $R^5$ is H and Q is $CH_2$.") below the Markush structure is replaced with the respective row heading shown below. For example, in Table 1B the row heading is "$R^1$ is F, $R^4$ is MeO, $R^5$ is H and Q is $CH_2$.", and Z is as defined in Table 2 above. Thus, the first entry in Table 1B specifically discloses methyl N-[[5-[3-(2,3-dihydro-5-benzofuranyl)-1H-pyrazol-1-yl]-2-fluorophenyl]methyl]carbamate. Tables 2B through 74B are constructed similarly.

| Table | Row Heading |
|---|---|
| 1B | $R^1$ is F, $R^4$ is MeO, $R^5$ is H and Q is $CH_2$. |
| 2B | $R^1$ is Me, $R^4$ is MeO, $R^5$ is H and Q is $CH_2$. |
| 3B | $R^1$ is CN, $R^4$ is MeO, $R^5$ is H and Q is $CH_2$. |
| 4B | $R^1$ is Cl, $R^4$ is MeO, $R^5$ is H and Q is NH. |
| 5B | $R^1$ is F, $R^4$ is MeO, $R^5$ is H and Q is NH. |
| 6B | $R^1$ is Me, $R^4$ is MeO, $R^5$ is H and Q is NH. |
| 7B | $R^1$ is CN, $R^4$ is MeO, $R^5$ is H and Q is NH. |
| 8B | $R^1$ is Cl, $R^4$ is MeO, $R^5$ is H and Q is O. |
| 9B | $R^1$ is F, $R^4$ is MeO, $R^5$ is H and Q is O. |
| 10B | $R^1$ is Me, $R^4$ is MeO, $R^5$ is H and Q is O. |
| 11B | $R^1$ is CN, $R^4$ is MeO, $R^5$ is H and Q is O. |
| 12B | $R^1$ is Cl, $R^4$ is MeHN, $R^5$ is H and Q is $CH_2$. |
| 13B | $R^1$ is F, $R^4$ is MeHN $R^5$ is H and Q is $CH_2$. |
| 14B | $R^1$ is Me, $R^4$ is MeHN, $R^5$ is H and Q is $CH_2$. |
| 15B | $R^1$ is Cl, $R^4$ is MeHN, $R^5$ is H and Q is NH. |
| 16B | $R^1$ is F, $R^4$ is MeHN, $R^5$ is H and Q is NH. |
| 17B | $R^1$ is Me, $R^4$ is MeHN, $R^5$ is H and Q is NH. |
| 18B | $R^1$ is Cl, $R^4$ is MeHN, $R^5$ is H and Q is O. |
| 19B | $R^1$ is F, $R^4$ is MeHN, $R^5$ is H and Q is O. |
| 20B | $R^1$ is Me, $R^4$ is MeHN, $R^5$ is H and Q is O. |
| 21B | $R^1$ is Cl, $R^4$ is Me, $R^5$ is H and Q is $CH_2$. |
| 22B | $R^1$ is F, $R^4$ is Me, $R^5$ is H and Q is $CH_2$. |
| 23B | $R^1$ is Me, $R^4$ is Me, $R^5$ is H and Q is $CH_2$. |
| 24B | $R^1$ is Cl, $R^4$ is Me, $R^5$ is H and Q is NH. |
| 25B | $R^1$ is F, $R^4$ is Me, $R^5$ is H and Q is NH. |
| 26B | $R^1$ is Me, $R^4$ is Me, $R^5$ is H and Q is NH. |
| 27B | $R^1$ is Cl, $R^4$ is Me, $R^5$ is H and Q is O. |
| 28B | $R^1$ is F, $R^4$ is Me, $R^5$ is H and Q is O. |
| 29B | $R^1$ is Me, $R^4$ is Me, $R^5$ is H and Q is O. |
| 30B | $R^1$ is Cl, $R^4$ is H, $R^5$ is H and Q is $CH_2$. |
| 31B | $R^1$ is F, $R^4$ is H, $R^5$ is H and Q is $CH_2$. |
| 32B | $R^1$ is Me, $R^4$ is H, $R^5$ is H and Q is $CH_2$. |
| 33B | $R^1$ is Cl, $R^4$ is H, $R^5$ is H and Q is NH. |
| 34B | $R^1$ is F, $R^4$ is H, $R^5$ is H and Q is NH. |
| 35B | $R^1$ is Me, $R^4$ is H, $R^5$ is H and Q is NH. |
| 36B | $R^1$ is Cl, $R^4$ is H, $R^5$ is H and Q is O. |
| 37B | $R^1$ is F, $R^4$ is H, $R^5$ is H and Q is O. |
| 38B | $R^1$ is Me, $R^4$ is H, $R^5$ is H and Q is O. |
| 39B | $R^1$ is Cl, $R^4$ is MeO, $R^5$ is Me and Q is $CH_2$. |
| 40B | $R^1$ is F, $R^4$ is MeO, $R^5$ is Me and Q is $CH_2$. |
| 41B | $R^1$ is Me, $R^4$ is MeO, $R^5$ is Me and Q is $CH_2$. |
| 42B | $R^1$ is Cl, $R^4$ is MeO, $R^5$ is Me and Q is NH. |
| 43B | $R^1$ is F, $R^4$ is MeO, $R^5$ is Me and Q is NH. |
| 44B | $R^1$ is Me, $R^4$ is MeO, $R^5$ is Me and Q is NH. |
| 45B | $R^1$ is Cl, $R^4$ is MeO, $R^5$ is Me and Q is O. |
| 46B | $R^1$ is F, $R^4$ is MeO, $R^5$ is Me and Q is O. |
| 47B | $R^1$ is Me, $R^4$ is MeO, $R^5$ is Me and Q is O. |
| 48B | $R^1$ is Cl, $R^4$ is MeHN, $R^5$ is Me and Q is $CH_2$. |
| 49B | $R^1$ is F, $R^4$ is MeHN, $R^5$ is Me and Q is $CH_2$. |
| 50B | $R^1$ is Me, $R^4$ is MeHN, $R^5$ is Me and Q is $CH_2$. |
| 51B | $R^1$ is Cl, $R^4$ is MeHN, $R^5$ is Me and Q is NH. |
| 52B | $R^1$ is F, $R^4$ is MeHN, $R^5$ is Me and Q is NH. |
| 53B | $R^1$ is Me, $R^4$ is MeHN, $R^5$ is Me and Q is NH. |
| 54B | $R^1$ is Cl, $R^4$ is MeHN, $R^5$ is Me and Q is O. |
| 55B | $R^1$ is F, $R^4$ is MeHN, $R^5$ is Me and Q is O. |
| 56B | $R^1$ is Me, $R^4$ is MeHN, $R^5$ is Me and Q is O. |
| 57B | $R^1$ is Cl, $R^4$ is Me, $R^5$ is Me and Q is $CH_2$. |
| 58B | $R^1$ is F, $R^4$ is Me, $R^5$ is Me and Q is $CH_2$. |
| 59B | $R^1$ is Me, $R^4$ is Me, $R^5$ is Me and Q is $CH_2$. |
| 60B | $R^1$ is Cl, $R^4$ is Me, $R^5$ is Me and Q is NH. |
| 61B | $R^1$ is F, $R^4$ is Me, $R^5$ is Me and Q is NH. |
| 62B | $R^1$ is Me, $R^4$ is Me, $R^5$ is Me and Q is NH. |
| 63B | $R^1$ is Cl, $R^4$ is Me, $R^5$ is Me and Q is O. |
| 64B | $R^1$ is F, $R^4$ is Me, $R^5$ is Me and Q is O. |
| 65B | $R^1$ is Me, $R^4$ is Me, $R^5$ is Me and Q is O. |
| 66B | $R^1$ is Cl, $R^4$ is H, $R^5$ is Me and Q is $CH_2$. |
| 67B | $R^1$ is F, $R^4$ is H, $R^5$ is Me and Q is $CH_2$. |
| 68B | $R^1$ is Me, $R^4$ is H, $R^5$ is Me and Q is $CH_2$. |
| 69B | $R^1$ is Cl, $R^4$ is H, $R^5$ is Me and Q is NH. |
| 70B | $R^1$ is F, $R^4$ is H, $R^5$ is Me and Q is NH. |
| 71B | $R^1$ is Me, $R^4$ is H, $R^5$ is Me and Q is NH. |
| 72B | $R^1$ is Cl, $R^4$ is H, $R^5$ is Me and Q is O. |
| 73B | $R^1$ is F, $R^4$ is H, $R^5$ is Me and Q is O. |
| 74B | $R^1$ is Me, $R^4$ is H, $R^5$ is Me and Q is O. |

TABLE 3

$R^1$ is Cl, $R^4$ is MeO, $R^5$ is H and Q is $CH_2$.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |

TABLE 3-continued

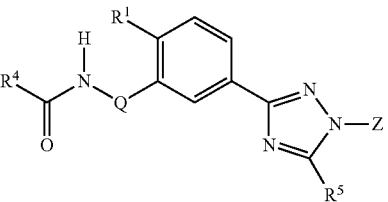

$R^1$ is Cl, $R^4$ is MeO, $R^5$ is H and Q is $CH_2$.

| Z | Z |
|---|---|
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |
| $Z^T$-22 | $Z^T$-46 |
| $Z^T$-23 | $Z^T$-47 |
| $Z^T$-24 | |

The present disclosure also includes Tables 1C through 74C, each of which is constructed the same as Table 3 above except that the row heading in Table 3 (i.e. "$R^1$ is Cl, $R^4$ is MeO, $R^5$ is H and Q is $CH_2$.") below the Markush structure is replaced with the respective row heading shown below. For example, in Table 1C the row heading is "$R^1$ is F, $R^4$ is MeO, $R^5$ is H and Q is $CH_2$.", and Z is as defined in Table 3 above. Thus, the first entry in Table 1C specifically discloses methyl N-[[5-[1-(2,3-dihydro-5-benzofuranyl)-1H-1,2,4-triazol-3-yl]-2-fluorophenyl]methyl]carbamate. Tables 2C through 74C are constructed similarly.

| Table | Row Heading |
|---|---|
| 1C | $R^1$ is F, $R^4$ is MeO, $R^5$ is H and Q is $CH_2$. |
| 2C | $R^1$ is Me, $R^4$ is MeO, $R^5$ is H and Q is $CH_2$. |
| 3C | $R^1$ is CN, $R^4$ is MeO, $R^5$ is H and Q is $CH_2$. |
| 4C | $R^1$ is Cl, $R^4$ is MeO, $R^5$ is H and Q is NH. |
| 5C | $R^1$ is F, $R^4$ is MeO, $R^5$ is H and Q is NH. |
| 6C | $R^1$ is Me, $R^4$ is MeO, $R^5$ is H and Q is NH. |
| 7C | $R^1$ is CN, $R^4$ is MeO, $R^5$ is H and Q is NH. |
| 8C | $R^1$ is Cl, $R^4$ is MeO, $R^5$ is H and Q is O. |
| 9C | $R^1$ is F, $R^4$ is MeO, $R^5$ is H and Q is O. |
| 10C | $R^1$ is Me, $R^4$ is MeO, $R^5$ is H and Q is O. |
| 11C | $R^1$ is CN, $R^4$ is MeO, $R^5$ is H and Q is O. |
| 12C | $R^1$ is Cl, $R^4$ is MeHN, $R^5$ is H and Q is $CH_2$. |
| 13C | $R^1$ is F, $R^4$ is MeHN $R^5$ is H and Q is $CH_2$. |
| 14C | $R^1$ is Me, $R^4$ is MeHN, $R^5$ is H and Q is $CH_2$. |
| 15C | $R^1$ is Cl, $R^4$ is MeHN, $R^5$ is H and Q is NH. |
| 16C | $R^1$ is F, $R^4$ is MeHN, $R^5$ is H and Q is NH. |
| 17C | $R^1$ is Me, $R^4$ is MeHN, $R^5$ is H and Q is NH. |
| 18C | $R^1$ is Cl, $R^4$ is MeHN, $R^5$ is H and Q is O. |
| 19C | $R^1$ is F, $R^4$ is MeHN, $R^5$ is H and Q is O. |
| 20C | $R^1$ is Me, $R^4$ is MeHN, $R^5$ is H and Q is O. |
| 21C | $R^1$ is Cl, $R^4$ is Me, $R^5$ is H and Q is $CH_2$. |
| 22C | $R^1$ is F, $R^4$ is Me, $R^5$ is H and Q is $CH_2$. |
| 23C | $R^1$ is Me, $R^4$ is Me, $R^5$ is H and Q is $CH_2$. |
| 24C | $R^1$ is Cl, $R^4$ is Me, $R^5$ is H and Q is NH. |
| 25C | $R^1$ is F, $R^4$ is Me, $R^5$ is H and Q is NH. |
| 26C | $R^1$ is Me, $R^4$ is Me, $R^5$ is H and Q is NH. |
| 27C | $R^1$ is Cl, $R^4$ is Me, $R^5$ is H and Q is O. |
| 28C | $R^1$ is F, $R^4$ is Me, $R^5$ is H and Q is O. |
| 29C | $R^1$ is Me, $R^4$ is Me, $R^5$ is H and Q is O. |
| 30C | $R^1$ is Cl, $R^4$ is H, $R^5$ is H and Q is $CH_2$. |
| 31C | $R^1$ is F, $R^4$ is H, $R^5$ is H and Q is $CH_2$. |
| 32C | $R^1$ is Me, $R^4$ is H, $R^5$ is H and Q is $CH_2$. |
| 33C | $R^1$ is Cl, $R^4$ is H, $R^5$ is H and Q is NH. |
| 34C | $R^1$ is F, $R^4$ is H, $R^5$ is H and Q is NH. |
| 35C | $R^1$ is Me, $R^4$ is H, $R^5$ is H and Q is NH. |
| 36C | $R^1$ is Cl, $R^4$ is H, $R^5$ is H and Q is O. |
| 37C | $R^1$ is F, $R^4$ is H, $R^5$ is H and Q is O. |
| 38C | $R^1$ is Me, $R^4$ is H, $R^5$ is H and Q is O. |
| 39C | $R^1$ is Cl, $R^4$ is MeO, $R^5$ is Me and Q is $CH_2$. |
| 40C | $R^1$ is F, $R^4$ is MeO, $R^5$ is Me and Q is $CH_2$. |
| 41C | $R^1$ is Me, $R^4$ is MeO, $R^5$ is Me and Q is $CH_2$. |
| 42C | $R^1$ is Cl, $R^4$ is MeO, $R^5$ is Me and Q is NH. |
| 43C | $R^1$ is F, $R^4$ is MeO, $R^5$ is Me and Q is NH. |
| 44C | $R^1$ is Me, $R^4$ is MeO, $R^5$ is Me and Q is NH. |
| 45C | $R^1$ is Cl, $R^4$ is MeO, $R^5$ is Me and Q is O. |
| 46C | $R^1$ is F, $R^4$ is MeO, $R^5$ is Me and Q is O. |
| 47C | $R^1$ is Me, $R^4$ is MeO, $R^5$ is Me and Q is O. |
| 48C | $R^1$ is Cl, $R^4$ is MeHN, $R^5$ is Me and Q is $CH_2$. |
| 49C | $R^1$ is F, $R^4$ is MeHN $R^5$ is Me and Q is $CH_2$. |
| 50C | $R^1$ is Me, $R^4$ is MeHN, $R^5$ is Me and Q is $CH_2$. |
| 51C | $R^1$ is Cl, $R^4$ is MeHN, $R^5$ is Me and Q is NH. |
| 52C | $R^1$ is F, $R^4$ is MeHN, $R^5$ is Me and Q is NH. |
| 53C | $R^1$ is Me, $R^4$ is MeHN, $R^5$ is Me and Q is NH. |
| 54C | $R^1$ is Cl, $R^4$ is MeHN, $R^5$ is Me and Q is O. |
| 55C | $R^1$ is F, $R^4$ is MeHN, $R^5$ is Me and Q is O. |
| 56C | $R^1$ is Me, $R^4$ is MeHN, $R^5$ is Me and Q is O. |
| 57C | $R^1$ is Cl, $R^4$ is Me, $R^5$ is Me and Q is $CH_2$. |
| 58C | $R^1$ is F, $R^4$ is Me, $R^5$ is Me and Q is $CH_2$. |
| 59C | $R^1$ is Me, $R^4$ is Me, $R^5$ is Me and Q is $CH_2$. |
| 60C | $R^1$ is Cl, $R^4$ is Me, $R^5$ is Me and Q is NH. |
| 61C | $R^1$ is F, $R^4$ is Me, $R^5$ is Me and Q is NH. |
| 62C | $R^1$ is Me, $R^4$ is Me, $R^5$ is Me and Q is NH. |
| 63C | $R^1$ is Cl, $R^4$ is Me, $R^5$ is Me and Q is O. |
| 64C | $R^1$ is F, $R^4$ is Me, $R^5$ is Me and Q is O. |
| 65C | $R^1$ is Me, $R^4$ is Me, $R^5$ is Me and Q is O. |
| 66C | $R^1$ is Cl, $R^4$ is H, $R^5$ is Me and Q is $CH_2$. |
| 67C | $R^1$ is F, $R^4$ is H, $R^5$ is Me and Q is $CH_2$. |
| 68C | $R^1$ is Me, $R^4$ is H, $R^5$ is Me and Q is $CH_2$. |
| 69C | $R^1$ is Cl, $R^4$ is H, $R^5$ is Me and Q is NH. |
| 70C | $R^1$ is F, $R^4$ is H, $R^5$ is Me and Q is NH. |
| 71C | $R^1$ is Me, $R^4$ is H, $R^5$ is Me and Q is NH. |
| 72C | $R^1$ is Cl, $R^4$ is H, $R^5$ is Me and Q is O. |
| 73C | $R^1$ is F, $R^4$ is H, $R^5$ is Me and Q is O. |
| 74C | $R^1$ is Me, $R^4$ is H, $R^5$ is Me and Q is O. |

TABLE 4

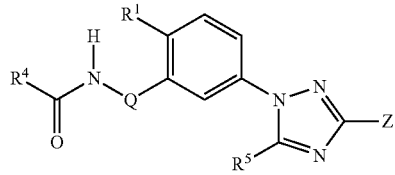

$R^1$ is Cl, $R^4$ is MeO, $R^5$ is H and Q is $CH_2$.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |

TABLE 4-continued

[Structure: R¹ on benzene ring with NH-C(=O)-R⁴ via O-Q linker, and 1,2,4-triazole ring with R⁵ and Z substituents]

R¹ is Cl, R⁴ is MeO, R⁵ is H and Q is CH₂.

| Z | Z |
|---|---|
| $Z^T$-22 | $Z^T$-46 |
| $Z^T$-23 | $Z^T$-47 |
| $Z^T$-24 | |

The present disclosure also includes Tables 1D through 74D, each of which is constructed the same as Table 4 above except that the row heading in Table 4 (i.e. "R¹ is Cl, R⁴ is MeO, R⁵ is H and Q is CH₂.") below the Markush structure is replaced with the respective row heading shown below. For example, in Table 1D the row heading is "R¹ is F, R⁴ is MeO, R⁵ is H and Q is CH₂.", and Z is as defined in Table 4 above. Thus, the first entry in Table 1D specifically discloses methyl N-[[5-[3-(2,3-dihydro-5-benzofuranyl)-1H-1,2,4-triazol-1-yl]-2-fluorophenyl]methyl]carbamate. Tables 2D through 74D are constructed similarly.

| Table | Row Heading |
|---|---|
| 1D | R¹ is F, R⁴ is MeO, R⁵ is H and Q is CH₂. |
| 2D | R¹ is Me, R⁴ is MeO, R⁵ is H and Q is CH₂. |
| 3D | R¹ is CN, R⁴ is MeO, R⁵ is H and Q is CH₂. |
| 4D | R¹ is Cl, R⁴ is MeO, R⁵ is H and Q is NH. |
| 5D | R¹ is F, R⁴ is MeO, R⁵ is H and Q is NH. |
| 6D | R¹ is Me, R⁴ is MeO, R⁵ is H and Q is NH. |
| 7D | R¹ is CN, R⁴ is MeO, R⁵ is H and Q is NH. |
| 8D | R¹ is Cl, R⁴ is MeO, R⁵ is H and Q is O. |
| 9D | R¹ is F, R⁴ is MeO, R⁵ is H and Q is O. |
| 10D | R¹ is Me, R⁴ is MeO, R⁵ is H and Q is O. |
| 11D | R¹ is CN, R⁴ is MeO, R⁵ is H and Q is O. |
| 12D | R¹ is Cl, R⁴ is MeHN, R⁵ is H and Q is CH₂. |
| 13D | R¹ is F, R⁴ is MeHN R⁵ is H and Q is CH₂. |
| 14D | R¹ is Me, R⁴ is MeHN, R⁵ is H and Q is CH₂. |
| 15D | R¹ is Cl, R⁴ is MeHN, R⁵ is H and Q is NH. |
| 16D | R¹ is F, R⁴ is MeHN, R⁵ is H and Q is NH. |
| 17D | R¹ is Me, R⁴ is MeHN, R⁵ is H and Q is NH. |
| 18D | R¹ is Cl, R⁴ is MeHN, R⁵ is H and Q is O. |
| 19D | R¹ is F, R⁴ is MeHN, R⁵ is H and Q is O. |
| 20D | R¹ is Me, R⁴ is MeHN, R⁵ is H and Q is O. |
| 21D | R¹ is Cl, R⁴ is Me, R⁵ is H and Q is CH₂. |
| 22D | R¹ is F, R⁴ is Me, R⁵ is H and Q is CH₂. |
| 23D | R¹ is Me, R⁴ is Me, R⁵ is H and Q is CH₂. |
| 24D | R¹ is Cl, R⁴ is Me, R⁵ is H and Q is NH. |
| 25D | R¹ is F, R⁴ is Me, R⁵ is H and Q is NH. |
| 26D | R¹ is Me, R⁴ is Me, R⁵ is H and Q is NH. |
| 27D | R¹ is Cl, R⁴ is Me, R⁵ is H and Q is O. |
| 28D | R¹ is F, R⁴ is Me, R⁵ is H and Q is O. |
| 29D | R¹ is Me, R⁴ is Me, R⁵ is H and Q is O. |
| 30D | R¹ is Cl, R⁴ is H, R⁵ is H and Q is CH₂. |
| 31D | R¹ is F, R⁴ is H, R⁵ is H and Q is CH₂. |
| 32D | R¹ is Me, R⁴ is H, R⁵ is H and Q is CH₂. |
| 33D | R¹ is Cl, R⁴ is H, R⁵ is H and Q is NH. |
| 34D | R¹ is F, R⁴ is H, R⁵ is H and Q is NH. |
| 35D | R¹ is Me, R⁴ is H, R⁵ is H and Q is NH. |
| 36D | R¹ is Cl, R⁴ is H, R⁵ is H and Q is O. |
| 37D | R¹ is F, R⁴ is H, R⁵ is H and Q is O. |
| 38D | R¹ is Me, R⁴ is H, R⁵ is H and Q is O. |
| 39D | R¹ is Cl, R⁴ is MeO, R⁵ is Me and Q is CH₂. |
| 40D | R¹ is F, R⁴ is MeO, R⁵ is Me and Q is CH₂. |
| 41D | R¹ is Me, R⁴ is MeO, R⁵ is Me and Q is CH₂. |
| 42D | R¹ is Cl, R⁴ is MeO, R⁵ is Me and Q is NH. |
| 43D | R¹ is F, R⁴ is MeO, R⁵ is Me and Q is NH. |
| 44D | R¹ is Me, R⁴ is MeO, R⁵ is Me and Q is NH. |
| 45D | R¹ is Cl, R⁴ is MeO, R⁵ is Me and Q is O. |
| 46D | R¹ is F, R⁴ is MeO, R⁵ is Me and Q is O. |
| 47D | R¹ is Me, R⁴ is MeO, R⁵ is Me and Q is O. |
| 48D | R¹ is Cl, R⁴ is MeHN, R⁵ is Me and Q is CH₂. |
| 49D | R¹ is F, R⁴ is MeHN R⁵ is Me and Q is CH₂. |
| 50D | R¹ is Me, R⁴ is MeHN, R⁵ is Me and Q is CH₂. |
| 51D | R¹ is Cl, R⁴ is MeHN, R⁵ is Me and Q is NH. |
| 52D | R¹ is F, R⁴ is MeHN, R⁵ is Me and Q is NH. |
| 53D | R¹ is Me, R⁴ is MeHN, R⁵ is Me and Q is NH. |
| 54D | R¹ is Cl, R⁴ is MeHN, R⁵ is Me and Q is O. |
| 55D | R¹ is F, R⁴ is MeHN, R⁵ is Me and Q is O. |
| 56D | R¹ is Me, R⁴ is MeHN, R⁵ is Me and Q is O. |
| 57D | R¹ is Cl, R⁴ is Me, R⁵ is Me and Q is CH₂. |
| 58D | R¹ is F, R⁴ is Me, R⁵ is Me and Q is CH₂. |
| 59D | R¹ is Me, R⁴ is Me, R⁵ is Me and Q is CH₂. |
| 60D | R¹ is Cl, R⁴ is Me, R⁵ is Me and Q is NH. |
| 61D | R¹ is F, R⁴ is Me, R⁵ is Me and Q is NH. |
| 62D | R¹ is Me, R⁴ is Me, R⁵ is Me and Q is NH. |
| 63D | R¹ is Cl, R⁴ is Me, R⁵ is Me and Q is O. |
| 64D | R¹ is F, R⁴ is Me, R⁵ is Me and Q is O. |
| 65D | R¹ is Me, R⁴ is Me, R⁵ is Me and Q is O. |
| 66D | R¹ is Cl, R⁴ is H, R⁵ is Me and Q is CH₂. |
| 67D | R¹ is F, R⁴ is H, R⁵ is Me and Q is CH₂. |
| 68D | R¹ is Me, R⁴ is H, R⁵ is Me and Q is CH₂. |
| 69D | R¹ is Cl, R⁴ is H, R⁵ is Me and Q is NH. |
| 70D | R¹ is F, R⁴ is H, R⁵ is Me and Q is NH. |
| 71D | R¹ is Me, R⁴ is H, R⁵ is Me and Q is NH. |
| 72D | R¹ is Cl, R⁴ is H, R⁵ is Me and Q is O. |
| 73D | R¹ is F, R⁴ is H, R⁵ is Me and Q is O. |
| 74D | R¹ is Me, R⁴ is H, R⁵ is Me and Q is O. |

TABLE 5

[Structure: R¹ on benzene ring with NH-C(=O)-R⁴ via O-Q linker, and dihydropyrazole ring with R⁵ and N-Z substituents]

R¹ is Cl, R⁴ is MeO, R⁵ is H and Q is CH₂.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |
| $Z^T$-22 | $Z^T$-46 |
| $Z^T$-23 | $Z^T$-47 |
| $Z^T$-24 | |

The present disclosure also includes Tables 1E through 74E, each of which is constructed the same as Table 5 above except that the row heading in Table 5 (i.e. "R¹ is Cl, R⁴ is MeO, R⁵ is H and Q is CH₂.") below the Markush structure is replaced with the respective row heading shown below. For example, in Table 1E the row heading is "$R^1$ is F, $R^4$ is MeO, $R^5$ is H and Q is $CH_2$.", and Z is as defined in Table 5 above. Thus, the first entry in Table 1E specifically discloses methyl N-[[5-[1-(2,3-dihydro-5-benzofuranyl)-4,5-dihydro-1H-pyrazol-3-yl]-2-fluorophenyl]methyl]carbamate. Tables 2E through 74E are constructed similarly.

| Table | Row Heading |
|---|---|
| 1E | $R^1$ is F, $R^4$ is MeO, $R^5$ is H and Q is $CH_2$. |
| 2E | $R^1$ is Me, $R^4$ is MeO, $R^5$ is H and Q is $CH_2$. |
| 3E | $R^1$ is CN, $R^4$ is MeO, $R^5$ is H and Q is $CH_2$. |
| 4E | $R^1$ is Cl, $R^4$ is MeO, $R^5$ is H and Q is NH. |
| 5E | $R^1$ is F, $R^4$ is MeO, $R^5$ is H and Q is NH. |
| 6E | $R^1$ is Me, $R^4$ is MeO, $R^5$ is H and Q is NH. |
| 7E | $R^1$ is CN, $R^4$ is MeO, $R^5$ is H and Q is NH. |
| 8E | $R^1$ is Cl, $R^4$ is MeO, $R^5$ is H and Q is O. |
| 9E | $R^1$ is F, $R^4$ is MeO, $R^5$ is H and Q is O. |
| 10E | $R^1$ is Me, $R^4$ is MeO, $R^5$ is H and Q is O. |
| 11E | $R^1$ is CN, $R^4$ is MeO, $R^5$ is H and Q is O. |
| 12E | $R^1$ is Cl, $R^4$ is MeHN, $R^5$ is H and Q is $CH_2$. |
| 13E | $R^1$ is F, $R^4$ is MeHN $R^5$ is H and Q is $CH_2$. |
| 14E | $R^1$ is Me, $R^4$ is MeHN, $R^5$ is H and Q is $CH_2$. |
| 15E | $R^1$ is Cl, $R^4$ is MeHN, $R^5$ is H and Q is NH. |
| 16E | $R^1$ is F, $R^4$ is MeHN, $R^5$ is H and Q is NH. |
| 17E | $R^1$ is Me, $R^4$ is MeHN, $R^5$ is H and Q is NH. |
| 18E | $R^1$ is Cl, $R^4$ is MeHN, $R^5$ is H and Q is O. |
| 19E | $R^1$ is F, $R^4$ is MeHN, $R^5$ is H and Q is O. |
| 20E | $R^1$ is Me, $R^4$ is MeHN, $R^5$ is H and Q is O. |
| 21E | $R^1$ is Cl, $R^4$ is Me, $R^5$ is H and Q is $CH_2$. |
| 22E | $R^1$ is F, $R^4$ is Me, $R^5$ is H and Q is $CH_2$. |
| 23E | $R^1$ is Me, $R^4$ is Me, $R^5$ is H and Q is $CH_2$. |
| 24E | $R^1$ is Cl, $R^4$ is Me, $R^5$ is H and Q is NH. |
| 25E | $R^1$ is F, $R^4$ is Me, $R^5$ is H and Q is NH. |
| 26E | $R^1$ is Me, $R^4$ is Me, $R^5$ is H and Q is NH. |
| 27E | $R^1$ is Cl, $R^4$ is Me, $R^5$ is H and Q is O. |
| 28E | $R^1$ is F, $R^4$ is Me, $R^5$ is H and Q is O. |
| 29E | $R^1$ is Me, $R^4$ is Me, $R^5$ is H and Q is O. |
| 30E | $R^1$ is Cl, $R^4$ is H, $R^5$ is H and Q is $CH_2$. |
| 31E | $R^1$ is F, $R^4$ is H, $R^5$ is H and Q is $CH_2$. |
| 32E | $R^1$ is Me, $R^4$ is H, $R^5$ is H and Q is $CH_2$. |
| 33E | $R^1$ is Cl, $R^4$ is H, $R^5$ is H and Q is NH. |
| 34E | $R^1$ is F, $R^4$ is H, $R^5$ is H and Q is NH. |
| 35E | $R^1$ is Me, $R^4$ is H, $R^5$ is H and Q is NH. |
| 36E | $R^1$ is Cl, $R^4$ is H, $R^5$ is H and Q is O. |
| 37E | $R^1$ is F, $R^4$ is H, $R^5$ is H and Q is O. |
| 38E | $R^1$ is Me, $R^4$ is H, $R^5$ is H and Q is O. |
| 39E | $R^1$ is Cl, $R^4$ is MeO, $R^5$ is Me and Q is $CH_2$. |
| 40E | $R^1$ is F, $R^4$ is MeO, $R^5$ is Me and Q is $CH_2$. |
| 41E | $R^1$ is Me, $R^4$ is MeO, $R^5$ is Me and Q is $CH_2$. |
| 42E | $R^1$ is Cl, $R^4$ is MeO, $R^5$ is Me and Q is NH. |
| 43E | $R^1$ is F, $R^4$ is MeO, $R^5$ is Me and Q is NH. |
| 44E | $R^1$ is Me, $R^4$ is MeO, $R^5$ is Me and Q is NH. |
| 45E | $R^1$ is Cl, $R^4$ is MeO, $R^5$ is Me and Q is O. |
| 46E | $R^1$ is F, $R^4$ is MeO, $R^5$ is Me and Q is O. |
| 47E | $R^1$ is Me, $R^4$ is MeO, $R^5$ is Me and Q is O. |
| 48E | $R^1$ is Cl, $R^4$ is MeHN, $R^5$ is Me and Q is $CH_2$. |
| 49E | $R^1$ is F, $R^4$ is MeHN $R^5$ is Me and Q is $CH_2$. |
| 50E | $R^1$ is Me, $R^4$ is MeHN, $R^5$ is Me and Q is $CH_2$. |
| 51E | $R^1$ is Cl, $R^4$ is MeHN, $R^5$ is Me and Q is NH. |
| 52E | $R^1$ is F, $R^4$ is MeHN, $R^5$ is Me and Q is NH. |
| 53E | $R^1$ is Me, $R^4$ is MeHN, $R^5$ is Me and Q is NH. |
| 54E | $R^1$ is Cl, $R^4$ is MeHN, $R^5$ is Me and Q is O. |
| 55E | $R^1$ is F, $R^4$ is MeHN, $R^5$ is Me and Q is O. |
| 56E | $R^1$ is Me, $R^4$ is MeHN, $R^5$ is Me and Q is O. |
| 57E | $R^1$ is Cl, $R^4$ is Me, $R^5$ is Me and Q is $CH_2$. |
| 58E | $R^1$ is F, $R^4$ is Me, $R^5$ is Me and Q is $CH_2$. |
| 59E | $R^1$ is Me, $R^4$ is Me, $R^5$ is Me and Q is $CH_2$. |
| 60E | $R^1$ is Cl, $R^4$ is Me, $R^5$ is Me and Q is NH. |
| 61E | $R^1$ is F, $R^4$ is Me, $R^5$ is Me and Q is NH. |
| 62E | $R^1$ is Me, $R^4$ is Me, $R^5$ is Me and Q is NH. |
| 63E | $R^1$ is Cl, $R^4$ is Me, $R^5$ is Me and Q is O. |
| 64E | $R^1$ is F, $R^4$ is Me, $R^5$ is Me and Q is O. |
| 65E | $R^1$ is Me, $R^4$ is Me, $R^5$ is Me and Q is O. |
| 66E | $R^1$ is Cl, $R^4$ is H, $R^5$ is Me and Q is $CH_2$. |
| 67E | $R^1$ is F, $R^4$ is H, $R^5$ is Me and Q is $CH_2$. |
| 68E | $R^1$ is Me, $R^4$ is H, $R^5$ is Me and Q is $CH_2$. |
| 69E | $R^1$ is Cl, $R^4$ is H, $R^5$ is Me and Q is NH. |
| 70E | $R^1$ is F, $R^4$ is H, $R^5$ is Me and Q is NH. |
| 71E | $R^1$ is Me, $R^4$ is H, $R^5$ is Me and Q is NH. |
| 72E | $R^1$ is Cl, $R^4$ is H, $R^5$ is Me and Q is O. |
| 73E | $R^1$ is F, $R^4$ is H, $R^5$ is Me and Q is O. |
| 74E | $R^1$ is Me, $R^4$ is H, $R^5$ is Me and Q is O. |

TABLE 6

$R^1$ is Cl, $R^4$ is MeO, $R^5$ is H and Q is $CH_2$.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |
| $Z^T$-22 | $Z^T$-46 |
| $Z^T$-23 | $Z^T$-47 |
| $Z^T$-24 | |

The present disclosure also includes Tables 1F through 74F, each of which is constructed the same as Table 6 above except that the row heading in Table 6 (i.e. "$R^1$ is Cl, $R^4$ is MeO, $R^5$ is H and Q is $CH_2$.") below the Markush structure is replaced with the respective row heading shown below. For example, in Table 1F the row heading is "$R^1$ is F, $R^4$ is MeO, $R^5$ is H and Q is $CH_2$.", and Z is as defined in Table 6 above. Thus, the first entry in Table 1F specifically discloses methyl N-[[5-[3-(2,3-dihydro-5-benzofuranyl)-4,5-dihydro-1H-pyrazol-1-yl]-2-fluorophenyl]methyl]carbamate. Tables 2F through 74F are constructed similarly.

| Table | Row Heading |
|---|---|
| 1F | $R^1$ is F, $R^4$ is MeO, $R^5$ is H and Q is $CH_2$. |
| 2F | $R^1$ is Me, $R^4$ is MeO, $R^5$ is H and Q is $CH_2$. |
| 3F | $R^1$ is CN, $R^4$ is MeO, $R^5$ is H and Q is $CH_2$. |
| 4F | $R^1$ is Cl, $R^4$ is MeO, $R^5$ is H and Q is NH. |
| 5F | $R^1$ is F, $R^4$ is MeO, $R^5$ is H and Q is NH. |
| 6F | $R^1$ is Me, $R^4$ is MeO, $R^5$ is H and Q is NH. |
| 7F | $R^1$ is CN, $R^4$ is MeO, $R^5$ is H and Q is NH. |
| 8F | $R^1$ is Cl, $R^4$ is MeO, $R^5$ is H and Q is O. |
| 9F | $R^1$ is F, $R^4$ is MeO, $R^5$ is H and Q is O. |
| 10F | $R^1$ is Me, $R^4$ is MeO, $R^5$ is H and Q is O. |

| Table | Row Heading |
|---|---|
| 11F | $R^1$ is CN, $R^4$ is MeO, $R^5$ is H and Q is O. |
| 12F | $R^1$ is Cl, $R^4$ is MeHN, $R^5$ is H and Q is $CH_2$. |
| 13F | $R^1$ is F, $R^4$ is MeHN $R^5$ is H and Q is $CH_2$. |
| 14F | $R^1$ is Me, $R^4$ is MeHN, $R^5$ is H and Q is $CH_2$. |
| 15F | $R^1$ is Cl, $R^4$ is MeHN, $R^5$ is H and Q is NH. |
| 16F | $R^1$ is F, $R^4$ is MeHN, $R^5$ is H and Q is NH. |
| 17F | $R^1$ is Me, $R^4$ is MeHN, $R^5$ is H and Q is NH. |
| 18F | $R^1$ is Cl, $R^4$ is MeHN, $R^5$ is H and Q is O. |
| 19F | $R^1$ is F, $R^4$ is MeHN, $R^5$ is H and Q is O. |
| 20F | $R^1$ is Me, $R^4$ is MeHN, $R^5$ is H and Q is O. |
| 21F | $R^1$ is Cl, $R^4$ is Me, $R^5$ is H and Q is $CH_2$. |
| 22F | $R^1$ is F, $R^4$ is Me, $R^5$ is H and Q is $CH_2$. |
| 23F | $R^1$ is Me, $R^4$ is Me, $R^5$ is H and Q is $CH_2$. |
| 24F | $R^1$ is Cl, $R^4$ is Me, $R^5$ is H and Q is NH. |
| 25F | $R^1$ is F, $R^4$ is Me, $R^5$ is H and Q is NH. |
| 26F | $R^1$ is Me, $R^4$ is Me, $R^5$ is H and Q is NH. |
| 27F | $R^1$ is Cl, $R^4$ is Me, $R^5$ is H and Q is O. |
| 28F | $R^1$ is F, $R^4$ is Me, $R^5$ is H and Q is O. |
| 29F | $R^1$ is Me, $R^4$ is Me, $R^5$ is H and Q is O. |
| 30F | $R^1$ is Cl, $R^4$ is H, $R^5$ is H and Q is $CH_2$. |
| 31F | $R^1$ is F, $R^4$ is H, $R^5$ is H and Q is $CH_2$. |
| 32F | $R^1$ is Me, $R^4$ is H, $R^5$ is H and Q is $CH_2$. |
| 33F | $R^1$ is Cl, $R^4$ is H, $R^5$ is H and Q is NH. |
| 34F | $R^1$ is F, $R^4$ is H, $R^5$ is H and Q is NH. |
| 35F | $R^1$ is Me, $R^4$ is H, $R^5$ is H and Q is NH. |
| 36F | $R^1$ is Cl, $R^4$ is H, $R^5$ is H and Q is O. |
| 37F | $R^1$ is F, $R^4$ is H, $R^5$ is H and Q is O. |
| 38F | $R^1$ is Me, $R^4$ is H, $R^5$ is H and Q is O. |
| 39F | $R^1$ is Cl, $R^4$ is MeO, $R^5$ is Me and Q is $CH_2$. |
| 40F | $R^1$ is F, $R^4$ is MeO, $R^5$ is Me and Q is $CH_2$. |
| 41F | $R^1$ is Me, $R^4$ is MeO, $R^5$ is Me and Q is $CH_2$. |
| 42F | $R^1$ is Cl, $R^4$ is MeO, $R^5$ is Me and Q is NH. |
| 43F | $R^1$ is F, $R^4$ is MeO, $R^5$ is Me and Q is NH. |
| 44F | $R^1$ is Me, $R^4$ is MeO, $R^5$ is Me and Q is NH. |
| 45F | $R^1$ is Cl, $R^4$ is MeO, $R^5$ is Me and Q is O. |
| 46F | $R^1$ is F, $R^4$ is MeO, $R^5$ is Me and Q is O. |
| 47F | $R^1$ is Me, $R^4$ is MeO, $R^5$ is Me and Q is O. |
| 48F | $R^1$ is Cl, $R^4$ is MeHN, $R^5$ is Me and Q is $CH_2$. |
| 49F | $R^1$ is F, $R^4$ is MeHN $R^5$ is Me and Q is $CH_2$. |
| 50F | $R^1$ is Me, $R^4$ is MeHN, $R^5$ is Me and Q is $CH_2$. |
| 51F | $R^1$ is Cl, $R^4$ is MeHN, $R^5$ is Me and Q is NH. |
| 52F | $R^1$ is F, $R^4$ is MeHN, $R^5$ is Me and Q is NH. |
| 53F | $R^1$ is Me, $R^4$ is MeHN, $R^5$ is Me and Q is NH. |
| 54F | $R^1$ is Cl, $R^4$ is MeHN, $R^5$ is Me and Q is O. |
| 55F | $R^1$ is F, $R^4$ is MeHN, $R^5$ is Me and Q is O. |
| 56F | $R^1$ is Me, $R^4$ is MeHN, $R^5$ is Me and Q is O. |
| 57F | $R^1$ is Cl, $R^4$ is Me, $R^5$ is Me and Q is $CH_2$. |
| 58F | $R^1$ is F, $R^4$ is Me, $R^5$ is Me and Q is $CH_2$. |
| 59F | $R^1$ is Me, $R^4$ is Me, $R^5$ is Me and Q is $CH_2$. |
| 60F | $R^1$ is Cl, $R^4$ is Me, $R^5$ is Me and Q is NH. |
| 61F | $R^1$ is F, $R^4$ is Me, $R^5$ is Me and Q is NH. |
| 62F | $R^1$ is Me, $R^4$ is Me, $R^5$ is Me and Q is NH. |
| 63F | $R^1$ is Cl, $R^4$ is Me, $R^5$ is Me and Q is O. |
| 64F | $R^1$ is F, $R^4$ is Me, $R^5$ is Me and Q is O. |
| 65F | $R^1$ is Me, $R^4$ is Me, $R^5$ is Me and Q is O. |
| 66F | $R^1$ is Cl, $R^4$ is H, $R^5$ is Me and Q is $CH_2$. |
| 67F | $R^1$ is F, $R^4$ is H, $R^5$ is Me and Q is $CH_2$. |
| 68F | $R^1$ is Me, $R^4$ is H, $R^5$ is Me and Q is $CH_2$. |
| 69F | $R^1$ is Cl, $R^4$ is H, $R^5$ is Me and Q is NH. |
| 70F | $R^1$ is F, $R^4$ is H, $R^5$ is Me and Q is NH. |
| 71F | $R^1$ is Me, $R^4$ is H, $R^5$ is Me and Q is NH. |
| 72F | $R^1$ is Cl, $R^4$ is H, $R^5$ is Me and Q is O. |
| 73F | $R^1$ is F, $R^4$ is H, $R^5$ is Me and Q is O. |
| 74F | $R^1$ is Me, $R^4$ is H, $R^5$ is Me and Q is O. |

TABLE 7

$R^1$ is Cl, $R^4$ is MeO, $R^5$ is H and Q is $CH_2$.

| Z | Z |
|---|---|
| $Z^T$-1 | $Z^T$-25 |
| $Z^T$-2 | $Z^T$-26 |
| $Z^T$-3 | $Z^T$-27 |
| $Z^T$-4 | $Z^T$-28 |
| $Z^T$-5 | $Z^T$-29 |
| $Z^T$-6 | $Z^T$-30 |
| $Z^T$-7 | $Z^T$-31 |
| $Z^T$-8 | $Z^T$-32 |
| $Z^T$-9 | $Z^T$-33 |
| $Z^T$-10 | $Z^T$-34 |
| $Z^T$-11 | $Z^T$-35 |
| $Z^T$-12 | $Z^T$-36 |
| $Z^T$-13 | $Z^T$-37 |
| $Z^T$-14 | $Z^T$-38 |
| $Z^T$-15 | $Z^T$-39 |
| $Z^T$-16 | $Z^T$-40 |
| $Z^T$-17 | $Z^T$-41 |
| $Z^T$-18 | $Z^T$-42 |
| $Z^T$-19 | $Z^T$-43 |
| $Z^T$-20 | $Z^T$-44 |
| $Z^T$-21 | $Z^T$-45 |
| $Z^T$-22 | $Z^T$-46 |
| $Z^T$-23 | $Z^T$-47 |
| $Z^T$-24 | |

The present disclosure also includes Tables 1G through 74G, each of which is constructed the same as Table 7 above except that the row heading in Table 7 (i.e. "$R^1$ is Cl, $R^4$ is MeO, $R^5$ is H and Q is $CH_2$.") below the Markush structure is replaced with the respective row heading shown below. For example, in Table 1G the row heading is "$R^1$ is F, $R^4$ is MeO, $R^5$ is H and Q is $CH_2$.", and Z is as defined in Table 7 above. Thus, the first entry in Table 1G specifically discloses methyl N-[[5-[2-(2,3-dihydro-5-benzofuranyl)-2H-1,2,3-triazol-4-yl]-2-fluorophenyl]methyl]carbamate. Tables 2G through 74G are constructed similarly.

| Table | Row Heading |
|---|---|
| 1G | $R^1$ is F, $R^4$ is MeO, $R^5$ is H and Q is $CH_2$. |
| 2G | $R^1$ is Me, $R^4$ is MeO, $R^5$ is H and Q is $CH_2$. |
| 3G | $R^1$ is CN, $R^4$ is MeO, $R^5$ is H and Q is $CH_2$. |
| 4G | $R^1$ is Cl, $R^4$ is MeO, $R^5$ is H and Q is NH. |
| 5G | $R^1$ is F, $R^4$ is MeO, $R^5$ is H and Q is NH. |
| 6G | $R^1$ is Me, $R^4$ is MeO, $R^5$ is H and Q is NH. |
| 7G | $R^1$ is CN, $R^4$ is MeO, $R^5$ is H and Q is NH. |
| 8G | $R^1$ is Cl, $R^4$ is MeO, $R^5$ is H and Q is O. |
| 9G | $R^1$ is F, $R^4$ is MeO, $R^5$ is H and Q is O. |
| 10G | $R^1$ is Me, $R^4$ is MeO, $R^5$ is H and Q is O. |
| 11G | $R^1$ is CN, $R^4$ is MeO, $R^5$ is H and Q is O. |
| 12G | $R^1$ is Cl, $R^4$ is MeHN, $R^5$ is H and Q is $CH_2$. |
| 13G | $R^1$ is F, $R^4$ is MeHN $R^5$ is H and Q is $CH_2$. |
| 14G | $R^1$ is Me, $R^4$ is MeHN, $R^5$ is H and Q is $CH_2$. |
| 15G | $R^1$ is Cl, $R^4$ is MeHN, $R^5$ is H and Q is NH. |
| 16G | $R^1$ is F, $R^4$ is MeHN, $R^5$ is H and Q is NH. |
| 17G | $R^1$ is Me, $R^4$ is MeHN, $R^5$ is H and Q is NH. |
| 18G | $R^1$ is Cl, $R^4$ is MeHN, $R^5$ is H and Q is O. |
| 19G | $R^1$ is F, $R^4$ is MeHN, $R^5$ is H and Q is O. |
| 20G | $R^1$ is Me, $R^4$ is MeHN, $R^5$ is H and Q is O. |
| 21G | $R^1$ is Cl, $R^4$ is Me, $R^5$ is H and Q is $CH_2$. |
| 22G | $R^1$ is F, $R^4$ is Me, $R^5$ is H and Q is $CH_2$. |
| 23G | $R^1$ is Me, $R^4$ is Me, $R^5$ is H and Q is $CH_2$. |

| Table | Row Heading |
|---|---|
| 24G | $R^1$ is Cl, $R^4$ is Me, $R^5$ is H and Q is NH. |
| 25G | $R^1$ is F, $R^4$ is Me, $R^5$ is H and Q is NH. |
| 26G | $R^1$ is Me, $R^4$ is Me, $R^5$ is H and Q is NH. |
| 27G | $R^1$ is Cl, $R^4$ is Me, $R^5$ is H and Q is O. |
| 28G | $R^1$ is F, $R^4$ is Me, $R^5$ is H and Q is O. |
| 29G | $R^1$ is Me, $R^4$ is Me, $R^5$ is H and Q is O. |
| 30G | $R^1$ is Cl, $R^4$ is H, $R^5$ is H and Q is $CH_2$. |
| 31G | $R^1$ is F, $R^4$ is H, $R^5$ is H and Q is $CH_2$. |
| 32G | $R^1$ is Me, $R^4$ is H, $R^5$ is H and Q is $CH_2$. |
| 33G | $R^1$ is Cl, $R^4$ is H, $R^5$ is H and Q is NH. |
| 34G | $R^1$ is F, $R^4$ is H, $R^5$ is H and Q is NH. |
| 35G | $R^1$ is Me, $R^4$ is H, $R^5$ is H and Q is NH. |
| 36G | $R^1$ is Cl, $R^4$ is H, $R^5$ is H and Q is O. |
| 37G | $R^1$ is F, $R^4$ is H, $R^5$ is H and Q is O. |
| 38G | $R^1$ is Me, $R^4$ is H, $R^5$ is H and Q is O. |
| 39G | $R^1$ is Cl, $R^4$ is MeO, $R^5$ is Me and Q is $CH_2$. |
| 40G | $R^1$ is F, $R^4$ is MeO, $R^5$ is Me and Q is $CH_2$. |
| 41G | $R^1$ is Me, $R^4$ is MeO, $R^5$ is Me and Q is $CH_2$. |
| 42G | $R^1$ is Cl, $R^4$ is MeO, $R^5$ is Me and Q is NH. |
| 43G | $R^1$ is F, $R^4$ is MeO, $R^5$ is Me and Q is NH. |
| 44G | $R^1$ is Me, $R^4$ is MeO, $R^5$ is Me and Q is NH. |
| 45G | $R^1$ is Cl, $R^4$ is MeO, $R^5$ is Me and Q is O. |
| 46G | $R^1$ is F, $R^4$ is MeO, $R^5$ is Me and Q is O. |
| 47G | $R^1$ is Me, $R^4$ is MeO, $R^5$ is Me and Q is O. |
| 48G | $R^1$ is Cl, $R^4$ is MeHN, $R^5$ is Me and Q is $CH_2$. |
| 49G | $R^1$ is F, $R^4$ is MeHN $R^5$ is Me and Q is $CH_2$. |
| 50G | $R^1$ is Me, $R^4$ is MeHN, $R^5$ is Me and Q is $CH_2$. |
| 51G | $R^1$ is Cl, $R^4$ is MeHN, $R^5$ is Me and Q is NH. |
| 52G | $R^1$ is F, $R^4$ is MeHN, $R^5$ is Me and Q is NH. |
| 53G | $R^1$ is Me, $R^4$ is MeHN, $R^5$ is Me and Q is NH. |
| 54G | $R^1$ is Cl, $R^4$ is MeHN, $R^5$ is Me and Q is O. |
| 55G | $R^1$ is F, $R^4$ is MeHN, $R^5$ is Me and Q is O. |
| 56G | $R^1$ is Me, $R^4$ is MeHN, $R^5$ is Me and Q is O. |
| 57G | $R^1$ is Cl, $R^4$ is Me, $R^5$ is Me and Q is $CH_2$. |
| 58G | $R^1$ is F, $R^4$ is Me, $R^5$ is Me and Q is $CH_2$. |
| 59G | $R^1$ is Me, $R^4$ is Me, $R^5$ is Me and Q is $CH_2$. |
| 60G | $R^1$ is Cl, $R^4$ is Me, $R^5$ is Me and Q is NH. |
| 61G | $R^1$ is F, $R^4$ is Me, $R^5$ is Me and Q is NH. |
| 62G | $R^1$ is Me, $R^4$ is Me, $R^5$ is Me and Q is NH. |
| 63G | $R^1$ is Cl, $R^4$ is Me, $R^5$ is Me and Q is O. |
| 64G | $R^1$ is F, $R^4$ is Me, $R^5$ is Me and Q is O. |
| 65G | $R^1$ is Me, $R^4$ is Me, $R^5$ is Me and Q is O. |
| 66G | $R^1$ is Cl, $R^4$ is H, $R^5$ is Me and Q is $CH_2$. |
| 67G | $R^1$ is F, $R^4$ is H, $R^5$ is Me and Q is $CH_2$. |
| 68G | $R^1$ is Me, $R^4$ is H, $R^5$ is Me and Q is $CH_2$. |
| 69G | $R^1$ is Cl, $R^4$ is H, $R^5$ is Me and Q is NH. |
| 70G | $R^1$ is F, $R^4$ is H, $R^5$ is Me and Q is NH. |
| 71G | $R^1$ is Me, $R^4$ is H, $R^5$ is Me and Q is NH. |
| 72G | $R^1$ is Cl, $R^4$ is H, $R^5$ is Me and Q is O. |
| 73G | $R^1$ is F, $R^4$ is H, $R^5$ is Me and Q is O. |
| 74G | $R^1$ is Me, $R^4$ is H, $R^5$ is Me and Q is O. |

Formulation/Utility

A compound of Formula 1 of this invention (including N-oxides and salts thereof) will generally be used as a fungicidal active ingredient in a composition, i.e. formulation, with at least one additional component selected from the group consisting of surfactants, solid diluents and liquid diluents, which serve as a carrier. The formulation or composition ingredients are selected to be consistent with the physical properties of the active ingredient, mode of application and environmental factors such as soil type, moisture and temperature.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion. The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-95 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g, oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such as polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2. Functional Materials*, annual International and North American editions published by McCutcheon's Division, The Manufacturing Confectioner Publishing Co.; and PCT Publication WO 03/024222.

The compound of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 μm can be wet milled using media mills to obtain particles with average diameters below 3 μm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 μm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering, Dec.* 4, 1967, pp 147-48, *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook,* 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Tables A-B. Without further elaboration, it is believed that one skilled in the art using the preceding description can utilize the present invention to its fullest extent. The following Examples are, therefore, to be constructed as merely illustrative, and not limiting of the disclosure in any way whatsoever. Percentages are by weight except where otherwise indicated.

Example A

High Strength Concentrate

| | |
|---|---|
| Compound 1 | 98.5% |
| silica aerogel | 0.5% |
| synthetic amorphous fine silica | 1.0% |

Example B

Wettable Powder

| | |
|---|---|
| Compound 5 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

Granule

| | |
|---|---|
| Compound 6 | 10.0% |
| attapulgite granules (low volatile matter, 0.71/0.30 mm; U.S.S. No. 25-50 sieves) | 90.0% |

Example D

Extruded Pellet

| | |
|---|---|
| Compound 7 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

Emulsifiable Concentrate

| | |
|---|---|
| Compound 1 | 10.0% |
| polyoxyethylene sorbitol hexoleate | 20.0% |
| $C_6$-$C_{10}$ fatty acid methyl ester | 70.0% |

Example F

Microemulsion

| | |
|---|---|
| Compound 5 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Example G

Seed Treatment

| | |
|---|---|
| Compound 6 | 20.00% |
| polyvinylpyrrolidone-vinyl acetate copolymer | 5.00% |

| | |
|---|---|
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Water-soluble and water-dispersible formulations are typically diluted with water to form aqueous compositions before application. Aqueous compositions for direct applications to the plant or portion thereof (e.g., spray tank compositions) typically at least about 1 ppm or more (e.g., from 1 ppm to 100 ppm) of the compound(s) of this invention.

The compounds of this invention are useful as plant disease control agents. The present invention therefore further comprises a method for controlling plant diseases caused by fungal plant pathogens comprising applying to the plant or portion thereof to be protected, or to the plant seed to be protected, an effective amount of a compound of the invention or a fungicidal composition containing said compound. The compounds and/or compositions of this invention provide control of diseases caused by a broad spectrum of fungal plant pathogens in the Basidiomycete, Ascomycete, Oomycete and Deuteromycete classes. They are effective in controlling a broad spectrum of plant diseases, particularly foliar pathogens of ornamental, turf, vegetable, field, cereal, and fruit crops. These pathogens include: Oomycetes, including *Phytophthora* diseases such as *Phytophthora infestans, Phytophthora megasperma, Phytophthora parasitica, Phytophthora cinnamomi* and *Phytophthora capsici, Pythium* diseases such as *Pythium aphanidermatum*, and diseases in the Peronosporaceae family such as *Plasmopara viticola, Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* diseases such as *Alternaria solani* and *Alternaria brassicae, Guignardia* diseases such as *Guignardia bidwell, Venturia* diseases such as *Venturia inaequalis, Septoria* diseases such as *Septoria nodorum* and *Septoria tritici*, powdery mildew diseases such as *Erysiphe* spp. (including *Erysiphe graminis* and *Erysiphe polygoni*), *Uncinula necatur, Sphaerotheca fuligena* and *Podosphaera leucotricha, Pseudocercosporella herpotrichoides, Botrytis* diseases such as *Botrytis cinerea, Monilinia fructicola, Sclerotinia* diseases such as *Sclerotinia sclerotiorum, Magnaporthe grisea, Phomopsis viticola, Helminthosporium* diseases such as *Helminthosporium tritici repentis, Pyrenophora teres*, anthracnose diseases such as *Glomerella* or *Colletotrichum* spp. (such as *Colletotrichum graminicola* and *Colletotrichum orbiculare*), and *Gaeumannomyces graminis*; Basidiomycetes, including rust diseases caused by *Puccinia* spp. (such as *Puccinia recondita, Puccinia striiformis, Puccinia hordei, Puccinia graminis* and *Puccinia arachidis*), *Hemileia vastatrix* and *Phakopsora pachyrhizi*; other pathogens including *Rutstroemia floccosum* (also known as *Sclerontina homoeocarpa*); *Rhizoctonia* spp. (such as *Rhizoctonia solani*); *Fusarium* diseases such as *Fusarium roseum, Fusarium graminearum* and *Fusarium oxysporum; Verticillium dahliae; Sclerotium rolfsii; Rynchosporium secalis; Cercosporidium personatum, Cercospora arachidicola* and *Cercospora beticola*; and other genera and species closely related to these pathogens. In addition to their fungicidal activity, the compositions or combinations also have activity against bacteria such as *Erwinia amylovora, Xanthomonas campestris, Pseudomonas syringae*, and other related species.

Plant disease control is ordinarily accomplished by applying an effective amount of a compound of this invention either pre- or post-infection, to the portion of the plant to be protected such as the roots, stems, foliage, fruit, seeds, tubers or bulbs, or to the media (soil or sand) in which the plants to be protected are growing. The compounds can also be applied to seeds to protect the seeds and seedlings developing from the seeds. The compounds can also be applied through irrigation water to treat plants.

Accordingly, this aspect of the present invention can also be described as a method for protecting a plant or plant seed from diseases caused by fungal pathogens comprising applying fungicidally effective amount of a compound of Formula 1, an N-oxide or salt thereof to the plant (or portion thereof) or plant seed (directly or through the environment (e.g., growing medium) of the plant or plant seed).

Rates of application for these compounds (i.e. a fungicidally effective amount) can be influenced by factors such as the plant diseases to be controlled, the plant species to be protected, ambient moisture and temperature and should be determined under actual use conditions. One skilled in the art can easily determine through simple experimentation the fungicidally effective amount necessary for the desired level of plant disease control. Foliage can normally be protected when treated at a rate of from less than about 1 g/ha to about 5,000 g/ha of active ingredient. Seed and seedlings can normally be protected when seed is treated at a rate of from about 0.1 to about 10 g per kilogram of seed.

Compounds of this invention can also be mixed with one or more other biologically active compounds or agents including fungicides, insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a compound of Formula 1 (in a fungicidally effective amount) and at least one additional biologically active compound or agent (in a biologically effective amount) and can further comprise at least one of a surfactant, a solid diluent or a liquid diluent. The other biologically active compounds or agents can be formulated in compositions comprising at least one of a surfactant, solid or liquid diluent. For mixtures of the present invention, one or more other biologically active compounds or agents can be formulated together with a compound of Formula 1, to form a premix, or one or more other biologically active compounds or agents can be formulated separately from the compound of Formula 1, and the formulations combined together before application (e.g., in a spray tank) or, alternatively, applied in succession.

Of note is a composition which in addition to the compound of Formula 1 include at least one fungicidal compound selected from the group consisting of the classes (1) methyl benzimidazole carbamate (MBC) fungicides; (2) dicarboximide fungicides; (3) demethylation inhibitor (DMI) fungicides; (4) phenylamide fungicides; (5) amine/morpholine fungicides; (6) phospholipid biosynthesis inhibitor fungicides; (7) carboxamide fungicides; (8) hydroxy(2-amino-) pyrimidine fungicides; (9) anilinopyrimidine fungicides; (10) N-phenyl carbamate fungicides; (11) quinone outside inhibitor (QoI) fungicides; (12) phenylpyrrole fungicides; (13)

quinoline fungicides; (14) lipid peroxidation inhibitor fungicides; (15) melanin biosynthesis inhibitors-reductase (MBI-R) fungicides; (16) melanin biosynthesis inhibitors-dehydratase (MBI-D) fungicides; (17) hydroxyanilide fungicides; (18) squalene-epoxidase inhibitor fungicides; (19) polyoxin fungicides; (20) phenylurea fungicides; (21) quinone inside inhibitor (QiI) fungicides; (22) benzamide fungicides; (23) enopyranuronic acid antibiotic fungicides; (24) hexopyranosyl antibiotic fungicides; (25) glucopyranosyl antibiotic: protein synthesis fungicides; (26) glucopyranosyl antibiotic: trehalase and inositol biosynthesis fungicides; (27) cyanoacetamideoxime fungicides; (28) carbamate fungicides; (29) oxidative phosphorylation uncoupling fungicides; (30) organo tin fungicides; (31) carboxylic acid fungicides; (32) heteroaromatic fungicides; (33) phosphonate fungicides; (34) phthalamic acid fungicides; (35) benzotriazine fungicides; (36) benzene-sulfonamide fungicides; (37) pyridazinone fungicides; (38) thiophene-carboxamide fungicides; (39) pyrimidinamide fungicides; (40) carboxylic acid amide (CAA) fungicides; (41) tetracycline antibiotic fungicides; (42) thiocarbamate fungicides; (43) benzamide fungicides; (44) host plant defense induction fungicides; (45) multi-site contact activity fungicides; (46) fungicides other than classes (1) through (45); and salts of compounds of classes (1) through (46).

Further descriptions of these classes of fungicidal compounds are provided below.

(1) "Methyl benzimidazole carbamate (MBC) fungicides" (Fungicide Resistance Action Committee (FRAC) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

(2) "Dicarboximide fungicides" (Fungicide Resistance Action Committee (FRAC) code 2) are proposed to inhibit a lipid peroxidation in fungi through interference with NADH cytochrome c reductase. Examples include chlozolinate, iprodione, procymidone and vinclozolin.

(3) "Demethylation inhibitor (DMI) fungicides" (Fungicide Resistance Action Committee (FRAC) code 3) inhibit C14-demethylase, which plays a role in sterol production. Sterols, such as ergosterol, are needed for membrane structure and function, making them essential for the development of functional cell walls. Therefore, exposure to these fungicides results in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, fenbuconazole, fluquinconazole, flusilazole, flutriafol, hexaconazole, imibenconazole, ipconazole, metconazole, myclobutanil, penconazole, propiconazole, prothioconazole, simeconazole, tebuconazole, tetraconazole, triadimefon, triadimenol, triticonazole and uniconazole. The imidazoles include clotrimazole, imazalil, oxpoconazole, prochloraz, pefurazoate and triflumizole. The pyrimidines include fenarimol and nuarimol. The piperazines include triforine. The pyridines include pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

(4) "Phenylamide fungicides" (Fungicide Resistance Action Committee (FRAC) code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl and metalaxyl-M/mefenoxam. The oxazolidinones include oxadixyl. The butyrolactones include ofurace.

(5) "Amine/morpholine fungicides" (Fungicide Resistance Action Committee (FRAC) code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

(6) "Phospholipid biosynthesis inhibitor fungicides" (Fungicide Resistance Action Committee (FRAC) code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

(7) "Carboxamide fungicides" (Fungicide Resistance Action Committee (FRAC) code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamides, furan carboxamides, oxathiin carboxamides, thiazole carboxamides, pyrazole carboxamides and pyridine carboxamides. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include furametpyr, penthiopyrad, bixafen, isopyrazam, N-[2-(1S,2R)-[1,1'-bicyclopropyl]-2-ylphenyl]-3-(difluoromethyl)-1-methyl-1H-pyrazole-4-carboxamide and N-[2-(1,3-dimethylbutyl)-phenyl]-5-fluoro-1,3-dimethyl-1H-pyrazole-4-carboxamide. The pyridine carboxamides include boscalid.

(8) "Hydroxy(2-amino-)pyrimidine fungicides" (Fungicide Resistance Action Committee (FRAC) code 8) inhibit nucleic acid synthesis by interfering with adenosine deaminase. Examples include bupirimate, dimethirimol and ethirimol.

(9) "Anilinopyrimidine fungicides" (Fungicide Resistance Action Committee (FRAC) code 9) are proposed to inhibit biosynthesis of the amino acid methionine and to disrupt the secretion of hydrolytic enzymes that lyse plant cells during infection. Examples include cyprodinil, mepanipyrim and pyrimethanil.

(10) "N-Phenyl carbamate fungicides" (Fungicide Resistance Action Committee (FRAC) code 10) inhibit mitosis by binding to β-tubulin and disrupting microtubule assembly Inhibition of microtubule assembly can disrupt cell division, transport within the cell and cell structure. Examples include diethofencarb.

(11) "Quinone outside inhibitor (QoI) fungicides" (Fungicide Resistance Action Committee (FRAC) code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides (also known as strobilurin fungicides) include methoxyacrylate, methoxycarbamate, oximinoacetate, oximinoacetamide, oxazolidinedione, dihydrodioxazine, imidazolinone and benzylcarbamate fungicides. The methoxyacrylates include azoxystrobin, enestroburin (SYP-Z071) and picoxystrobin. The methoxycarbamates include pyraclostrobin. The oximinoacetates include kresoxim-methyl and trifloxystrobin. The oximinoacetamides include dimoxystrobin, metominostrobin, orysastrobin, α-[methoxyimino]-N-methyl-2-[[[1-[3-(trifluoromethyl)phenyl]ethoxy]imino]-methyl]benzeneacetamide and 2-[[[3-(2,6-dichlorophenyl)-1-methyl-2-propen-1-ylidene]-amino]oxy]methyl]-α-(methoxyimino)-N-methylbenzeneacetamide. The oxazolidinediones include famoxadone. The dihydrodioxazines include fluoxastrobin. The imidazolinones include fenamidone. The benzylcarbamates include pyribencarb.

(12) "Phenylpyrrole fungicides" (Fungicide Resistance Action Committee (FRAC) code 12) inhibit a MAP protein kinase associated with osmotic signal transduction in fungi. Fenpiclonil and fludioxonil are examples of this fungicide class.

(13) "Quinoline fungicides" (Fungicide Resistance Action Committee (FRAC) code 13) are proposed to inhibit signal transduction by affecting G-proteins in early cell signaling. They have been shown to interfere with germination and/or appressorium formation in fungi that cause powder mildew diseases. Quinoxyfen is an example of this class of fungicide.

(14) "Lipid peroxidation inhibitor fungicides" (Fungicide Resistance Action Committee (FRAC) code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbon fungicides include biphenyl, chloroneb, dicloran, quintozene, tecnazene and tolclofosmethyl. The 1,2,4-thiadiazole fungicides include etridiazole.

(15) "Melanin biosynthesis inhibitors-reductase (MBI-R) fungicides" (Fungicide Resistance Action Committee (FRAC) code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

(16) "Melanin biosynthesis inhibitors-dehydratase (MBI-D) fungicides" (Fungicide Resistance Action Committee (FRAC) code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

(17) "Hydroxyanilide fungicides (Fungicide Resistance Action Committee (FRAC) code 17) inhibit C4-demethylase which plays a role in sterol production. Examples include fenhexamid.

(18) "Squalene-epoxidase inhibitor fungicides" (Fungicide Resistance Action Committee (FRAC) code 18) inhibit squalene-epoxidase in ergosterol biosynthesis pathway. Sterols such as ergosterol are needed for membrane structure and function, making them essential for the development of functional cell walls. Therefore exposure to these fungicides results in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

(19) "Polyoxin fungicides" (Fungicide Resistance Action Committee (FRAC) code 19) inhibit chitin synthase. Examples include polyoxin.

(20) "Phenylurea fungicides" (Fungicide Resistance Action Committee (FRAC) code 20) are proposed to affect cell division. Examples include pencycuron.

(21) "Quinone inside inhibitor (QiI) fungicides" (Fungicide Resistance Action Committee (FRAC) code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

(22) "Benzamide fungicides" (Fungicide Resistance Action Committee (FRAC) code 22) inhibit mitosis by binding to β-tubulin and disrupting microtubule assembly. Inhibition of microtubule assembly can disrupt cell division, transport within the cell and cell structure. Examples include zoxamide.

(23) "Enopyranuronic acid antibiotic fungicides" (Fungicide Resistance Action Committee (FRAC) code 23) inhibit growth of fungi by affecting protein biosynthesis. Examples include blasticidin-S.

(24) "Hexopyranosyl antibiotic fungicides" (Fungicide Resistance Action Committee (FRAC) code 24) inhibit growth of fungi by affecting protein biosynthesis. Examples include kasugamycin.

(25) "Glucopyranosyl antibiotic: protein synthesis fungicides" (Fungicide Resistance Action Committee (FRAC) code 25) inhibit growth of fungi by affecting protein biosynthesis. Examples include streptomycin.

(26) "Glucopyranosyl antibiotic: trehalase and inositol biosynthesis fungicides" (Fungicide Resistance Action Committee (FRAC) code 26) inhibit trehalase in inositol biosynthesis pathway. Examples include validamycin.

(27) "Cyanoacetamideoxime fungicides (Fungicide Resistance Action Committee (FRAC) code 27) include cymoxanil.

(28) "Carbamate fungicides" (Fungicide Resistance Action Committee (FRAC) code 28) are considered multi-site inhibitors of fungal growth. They are proposed to interfere with the synthesis of fatty acids in cell membranes, which then disrupts cell membrane permeability. Propamacarb, propamacarb-hydrochloride, iodocarb, and prothiocarb are examples of this fungicide class.

(29) "Oxidative phosphorylation uncoupling fungicides" (Fungicide Resistance Action Committee (FRAC) code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

(30) "Organo tin fungicides" (Fungicide Resistance Action Committee (FRAC) code 30) inhibit adenosine triphosphate (ATP) synthase in oxidative phosphorylation pathway. Examples include fentin acetate, fentin chloride and fentin hydroxide.

(31) "Carboxylic acid fungicides" (Fungicide Resistance Action Committee (FRAC) code 31) inhibit growth of fungi by affecting deoxyribonucleic acid (DNA) topoisomerase type II (gyrase). Examples include oxolinic acid.

(32) "Heteroaromatic fungicides" (Fungicide Resistance Action Committee (FRAC) code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

(33) "Phosphonate fungicides" (Fungicide Resistance Action Committee (FRAC) code 33) include phosphorous acid and its various salts, including fosetyl-aluminum.

(34) "Phthalamic acid fungicides" (Fungicide Resistance Action Committee (FRAC) code 34) include teclofthalam.

(35) "Benzotriazine fungicides" (Fungicide Resistance Action Committee (FRAC) code 35) include triazoxide.

(36) "Benzene-sulfonamide fungicides" (Fungicide Resistance Action Committee (FRAC) code 36) include flusulfamide.

(37) "Pyridazinone fungicides" (Fungicide Resistance Action Committee (FRAC) code 37) include diclomezine.

(38) "Thiophene-carboxamide fungicides" (Fungicide Resistance Action Committee (FRAC) code 38) are proposed to affect ATP production. Examples include silthiofam.

(39) "Pyrimidinamide fungicides" (Fungicide Resistance Action Committee (FRAC) code 39) inhibit growth of fungi by affecting phospholipid biosynthesis and include diflumetorim.

(40) "Carboxylic acid amide (CAA) fungicides" (Fungicide Resistance Action Committee (FRAC) code 40) are proposed to inhibit phospholipid biosynthesis and cell wall deposition Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valiphenal. The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]ethyl]-3-methyl-2-[(ethylsulfonyl)amino]butanamide.

(41) "Tetracycline antibiotic fungicides" (Fungicide Resistance Action Committee (FRAC) code 41) inhibit growth of fungi by affecting complex 1 nicotinamide adenine dinucleotide (NADH) oxidoreductase. Examples include oxytetracycline.

(42) "Thiocarbamate fungicides (b42)" (Fungicide Resistance Action Committee (FRAC) code 42) include methasulfocarb.

(43) "Benzamide fungicides" (Fungicide Resistance Action Committee (FRAC) code 43) inhibit growth of fungi by delocalization of spectrin-like proteins. Examples include acylpicolide fungicides such as fluopicolide and fluopyram.

(44) "Host plant defense induction fungicides" (Fungicide Resistance Action Committee (FRAC) code P) induce host plant defense mechanisms. Host plant defense induction fungicides include benzo-thiadiazole, benzisothiazole and thiadiazole-carboxamide fungicides. The benzo-thiadiazoles include acibenzolar-5-methyl. The benzisothiazoles include probenazole. The thiadiazole-carboxamides include tiadinil and isotianil.

(45) "Multi-site contact fungicides" inhibit fungal growth through multiple sites of action and have contact/preventive activity. This class of fungicides includes: (45.1) "copper fungicides" (Fungicide Resistance Action Committee (FRAC) code M1)", (45.2) "sulfur fungicides" (Fungicide Resistance Action Committee (FRAC) code M2), (45.3) "dithiocarbamate fungicides" (Fungicide Resistance Action Committee (FRAC) code M3), (45.4) "phthalimide fungicides" (Fungicide Resistance Action Committee (FRAC) code M4), (45.5) "chloronitrile fungicides" (Fungicide Resistance Action Committee (FRAC) code M5), (45.6) "sulfamide fungicides" (Fungicide Resistance Action Committee (FRAC) code M6), (45.7) "guanidine fungicides" (Fungicide Resistance Action Committee (FRAC) code M7), (45.8) "triazine fungicides" (Fungicide Resistance Action Committee (FRAC) code M8) and (45.9) "quinone fungicides" (Fungicide Resistance Action Committee (FRAC) code M9). "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolyfluanid. "Guanidine fungicides" include dodine, guazatine, iminoctadine albesilate and iminoctadine triacetate. "Triazine fungicides" include anilazine. "Quinone fungicides" include dithianon.

(46) "Fungicides other than fungicides of classes (1) through (45)" include certain fungicides whose mode of action may be unknown. These include: (46.1) "thiazole carboxamide fungicides" (Fungicide Resistance Action Committee (FRAC) code U5), (46.2) "phenyl-acetamide fungicides" (Fungicide Resistance Action Committee (FRAC) code U6), (46.3) "quinazolinone fungicides" (Fungicide Resistance Action Committee (FRAC) code U7) and (46.4) "benzophenone fungicides" (Fungicide Resistance Action Committee (FRAC) code U8). The thiazole carboxamides include ethaboxam. The phenyl-acetamides include cyflufenamid and N-[[(cyclopropylmethoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone. The (b46) class also includes bethoxazin, neo-asozin (ferric methanearsonate), pyrrolnitrin, quinomethionate, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]-butanamide, 2-[[2-fluoro- 5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl] carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzenesulfonamide, N-[[(cyclopropylmethoxy)-amino][6-(difluoromethoxy)-2,3-difluorophenyl]methylene]benzeneacetamide, N-[4-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1H-pyrazol-3-one.

Therefore of note is a mixture (i.e. composition) comprising a compound of Formula 1 and at least one fungicidal compound selected from the group consisting of the aforedescribed classes (1) through (46). Also of note is a composition comprising said mixture (in fungicidally effective amount) and further comprising at least one additional component selected from the group consisting of surfactants, solid diluents and liquid diluents. Of particular note is a mixture (i.e. composition) comprising a compound of Formula 1 and at least one fungicidal compound selected from the group of specific compounds listed above in connection with classes (1) through (46). Also of particular note is a composition comprising said mixture (in fungicidally effective amount) and further comprising at least one additional surfactant selected from the group consisting of surfactants, solid diluents and liquid diluents.

Examples of other biologically active compounds or agents with which compounds of this invention can be formulated are: insecticides such as abamectin, acephate, acetamiprid, amidoflumet (S-1955), avermectin, azadirachtin, azinphos-methyl, bifenthrin, bifenazate, buprofezin, carbofuran, cartap, chlorantraniliprole, chlorfenapyr, chlorfluazuron, chlorpyrifos, chlorpyrifos-methyl, chromafenozide, clothianidin, cyantraniliprole (3-bromo-1-(3-chloro-2-pyridinyl)-N-[4-cyano-2-methyl-6-[(methylamino)carbonyl]phenyl]-1H-pyrazole-5-carboxamide), cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin, endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, monocrotophos, methoxyfenozide, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tralomethrin, triazamate, trichlorfon and triflumuron; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

Compounds of this invention and compositions thereof can be applied to plants genetically transformed to express proteins toxic to invertebrate pests (such as *Bacillus thuringiensis* delta-endotoxins). The effect of the exogenously applied fungicidal compounds of this invention may be synergistic with the expressed toxin proteins.

General references for agricultural protectants (i.e. insecticides, fungicides, nematocides, acaricides, herbicides and biological agents) include *The Pesticide Manual, 13th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

For embodiments where one or more of these various mixing partners are used, the weight ratio of these various mixing partners (in total) to the compound of Formula 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components may expand the spectrum of diseases controlled beyond the spectrum controlled by the compound of Formula 1 alone.

In certain instances, combinations of a compound of this invention with other biologically active (particularly fungicidal) compounds or agents (i.e. active ingredients) can result in a greater-than-additive (i.e. synergistic) effect. Reducing the quantity of active ingredients released in the environment while ensuring effective pest control is always desirable. When synergism of fungicidal active ingredients occurs at application rates giving agronomically satisfactory levels of fungal control, such combinations can be advantageous for reducing crop production cost and decreasing environmental load.

Of note is a combination of a compound of Formula 1 with at least one other fungicidal active ingredient. Of particular note is such a combination where the other fungicidal active ingredient has different site of action from the compound of Formula 1. In certain instances, a combination with at least one other fungicidal active ingredient having a similar spectrum of control but a different site of action will be particularly advantageous for resistance management. Thus, a composition of the present invention can further comprise a biologically effective amount of at least one additional fungicidal active ingredient having a similar spectrum of control but a different site of action.

Of particular note are compositions which in addition to compound of Formula 1 include at least one compound selected from the group consisting of (1) alkylenebis(dithiocarbamate) fungicides; (2) cymoxanil; (3) phenylamide fungicides; (4) pyrimidinone fungicides; (5) chlorothalonil; (6) carboxamides acting at complex II of the fungal mitochondrial respiratory electron transfer site; (7) quinoxyfen; (8) metrafenone; (9) cyflufenamid; (10) cyprodinil; (11) copper compounds; (12) phthalimide fungicides; (13) fosetyl-aluminum; (14) benzimidazole fungicides; (15) cyazofamid; (16) fluazinam; (17) iprovalicarb; (18) propamocarb; (19) validomycin; (20) dichlorophenyl dicarboximide fungicides; (21) zoxamide; (22) fluopicolide; (23) mandipropamid; (24) carboxylic acid amides acting on phospholipid biosynthesis and cell wall deposition; (25) dimethomorph; (26) non-DMI sterol biosynthesis inhibitors; (27) inhibitors of demethylase in sterol biosynthesis; (28) bc₁ complex fungicides; and salts of compounds of (1) through (28).

Further descriptions of classes of fungicidal compounds are provided below.

Pyrimidinone fungicides (group (4)) include compounds of Formula A1

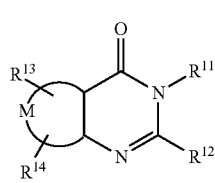

A1 wherein M forms a fused phenyl, thiophene or pyridine ring; $R^{11}$ is $C_1$-$C_6$ alkyl; $R^{12}$ is $C_1$-$C_6$ alkyl or $C_1$-$C_6$ alkoxy; $R^{13}$ is halogen; and $R^{14}$ is hydrogen or halogen.

Pyrimidinone fungicides are described in PCT Patent Application Publication WO 94/26722 and U.S. Pat. Nos. 6,066,638, 6,245,770, 6,262,058 and 6,277,858. Of note are pyrimidinone fungicides selected from the group: 6-bromo-3-propyl-2-propyloxy-4(3H)-quinazolinone, 6,8-diiodo-3-propyl-2-propyloxy-4(3H)-quinazolinone, 6-iodo-3-propyl-2-propyloxy-4(3H)-quinazolinone (proquinazid), 6-chloro-2-propoxy-3-propylthieno[2,3-d]pyrimidin-4(3H)-one, 6-bromo-2-propoxy-3-propylthieno[2,3-d]pyrimidin-4(3H)-one, 7-bromo-2-propoxy-3-propylthieno[3,2-d]pyrimidin-4(3H)-one, 6-bromo-2-propoxy-3-propylpyrido[2,3-d]pyrimidin-4(3H)-one, 6,7-dibromo-2-propoxy-3-propylthieno[3,2-d]pyrimidin-4(3H)-one, and 3-(cyclopropylmethyl)-6-iodo-2-(propylthio)pyrido-[2,3-d]pyrimidin-4(3H)-one.

Sterol biosynthesis inhibitors (group (27)) control fungi by inhibiting enzymes in the sterol biosynthesis pathway. Demethylase-inhibiting fungicides have a common site of action within the fungal sterol biosynthesis pathway, involving inhibition of demethylation at position 14 of lanosterol or 24-methylene dihydrolanosterol, which are precursors to sterols in fungi. Compounds acting at this site are often referred to as demethylase inhibitors, DMI fungicides, or DMIs. The demethylase enzyme is sometimes referred to by other names in the biochemical literature, including cytochrome P-450 (14DM). The demethylase enzyme is described in, for example, *J. Biol. Chem.* 1992, 267, 13175-79 and references cited therein. DMI fungicides are divided between several chemical classes: azoles (including triazoles and imidazoles), pyrimidines, piperazines and pyridines. The triazoles include azaconazole, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

bc₁ Complex Fungicides (group 28) have a fungicidal mode of action which inhibits the bc₁ complex in the mitochondrial respiration chain. The bc₁ complex is sometimes referred to by other names in the biochemical literature, including complex III of the electron transfer chain, and ubihydroquinone:cytochrome c oxidoreductase. This complex is uniquely identified by Enzyme Commission number EC1.10.2.2. The bc₁ complex is described in, for example, *J. Biol. Chem.* 1989, 264, 14543-48; *Methods Enzymol.* 1986, 126, 253-71; and references cited therein. Strobilurin fungicides such as azoxystrobin, dimoxystrobin, enestroburin (SYP-Z071), fluoxastrobin, kresoxim-methyl, metominostrobin, orysastrobin, picoxystrobin, pyraclostrobin and trifloxystrobin are known to have this mode of action (H. Sauter et al., *Angew. Chem. Int. Ed.* 1999, 38, 1328-1349). Other fungicidal compounds that inhibit the bc₁ complex in the mitochondrial respiration chain include famoxadone and fenamidone.

Alkylenebis(dithiocarbamate)s (group (1)) include compounds such as mancozeb, maneb, propineb and zineb. Phenylamides (group (3)) include compounds such as metalaxyl, benalaxyl, furalaxyl and oxadixyl. Carboxamides (group (6)) include compounds such as boscalid, carboxin, fenfuram, flutolanil, furametpyr, mepronil, oxycarboxin, thifluzamide, penthiopyrad and N-[2-(1,3-dimethylbutyl)phenyl]-5-fluoro-1,3-dimethyl-1H-pyrazole-4-carboxamide (PCT Patent Publication WO 2003/010149), and are known to inhibit mitochondrial function by disrupting complex II (succinate dehydrogenase) in the respiratory electron transport chain. Copper compounds (group (11)) include compounds such as copper oxychloride, copper sulfate and copper hydroxide, including compositions such as Bordeaux mixture (tribasic copper sulfate). Phthalimides (group (12)) include compounds such as folpet and captan. Benzimidazole fungicides (group (14)) include benomyl and carbendazim. Dichlorophenyl dicarboximide fungicides (group (20)) include chlozolinate, dichlozoline, iprodione, isovaledione, myclozolin, procymidone and vinclozolin.

Non-DMI sterol biosynthesis inhibitors (group (26)) include morpholine and piperidine fungicides. The morpholines and piperidines are sterol biosynthesis inhibitors that have been shown to inhibit steps in the sterol biosynthesis pathway at a point later than the inhibitions achieved by the DMI sterol biosynthesis (group (27)). The morpholines include aldimorph, dodemorph, fenpropimorph, tridemorph and trimorphamide. The piperidines include fenpropidin Of further note are combinations of compounds of Formula 1 with azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid (nicobifen).

Preferred for better control of plant diseases caused by fungal plant pathogens (e.g., lower use rate or broader spectrum of plant pathogens controlled) or resistance management are mixtures of a compound of this invention with a fungicide selected from the group: azoxystrobin, kresoxim-methyl, trifloxystrobin, pyraclostrobin, picoxystrobin, dimoxystrobin, metominostrobin/fenominostrobin, quinoxyfen, metrafenone, cyflufenamid, fenpropidine, fenpropimorph, cyproconazole, epoxiconazole, flusilazole, metconazole, propiconazole, proquinazid, prothioconazole, tebuconazole, triticonazole, famoxadone and penthiopyrad.

The following Tests demonstrate the control efficacy of compounds of this invention on specific pathogens. The pathogen control protection afforded by the compounds is not limited, however, to these species. See Index Tables A-B for compound descriptions. The abbreviation "Ex." stands for "Example" and is followed by a number indicating in which Synthesis Example the compound is prepared. For mass spectral data, the numerical value reported in column headed "AP+ (M+1)" is the molecular weight of the observed molecular ion formed by addition of H+ (molecular weight of 1) to the molecule having the greatest isotopic abundance (i.e. M). The presence of molecular ions containing one or more higher atomic weight isotopes of lower abundance (e.g., $^{37}$Cl, $^{81}$Br) is not reported. The reported M+1 peaks were observed by mass spectrometry using atmospheric pressure chemical ionization (AP+).

INDEX TABLE A

| Compound | $R^1$ | $R^4$ | Q | Z (***) | AP+ (M + 1) | m.p. (° C.) |
|---|---|---|---|---|---|---|
| 1 (Ex. 7) | Cl | CH$_3$O | CH$_2$ | Z-6 wherein n and p are 0 | ** | |
| 2 (Ex. 6) | Cl | CH$_3$ | CH$_2$ | Z-6 wherein n and p are 0 | 382 | |
| 3 (Ex. 4) | Cl | H | CH$_2$ | Z-6 wherein n and p are 0 | 368 | |
| 4 (Ex. 5) | Cl | CH$_3$NH | CH$_2$ | Z-6 wherein n and p are 0 | 397 | |
| 12 | F | CH$_3$O | CH$_2$ | Z-6 wherein n and p are 0 | | 134-138 |
| 13 | F | CH$_3$O | CH$_2$ | Z-31 wherein n and p are 0 and $R^{9a}$ is CH$_3$ | | 92-95 |
| 16 | Br | CH$_3$O | CH$_2$ | Z-6 wherein n and p are 0 | | 128-130 |
| 17 | Br | CH$_3$O | CH$_2$ | Z-9 wherein n and p are 0 | | 124-126 |
| 19 | CH$_3$ | CH$_3$O | CH$_2$ | Z-9 wherein n and p are 0 | | 138-139 |
| 20 | CH3 | CH$_3$O | CH$_2$ | Z-6 wherein n and p are 0 | | 161-162 |
| 23 (Ex. 8) | Cl | CH$_3$O | CH$_2$ | Z-7 wherein n and $R^{8b}$ is 3-CO$_2$CH$_3$ | | 185-187 |
| 24 (Ex. 8) | Cl | CH$_3$O | CH$_2$ | Z-7 wherein n and $R^{8b}$ is 3-CO$_2$H | | 245-247 |
| 27 | Cl | CH$_3$O | CH$_2$ | Z-7 wherein n and $R^{8b}$ is 3-CN | | 203-206 |
| 28 (Ex. 9) | Cl | CH$_3$O | CH$_2$ | Z-30 wherein n and p are 0 | | 70-73 |
| 29 (Ex. 10) | Cl | CH$_3$O | CH$_2$ | Z-8 wherein n and p are 0 | | 104-106 |
| 30 (Ex. 11) | Cl | CH$_3$O | CH$_2$ | Z-6 wherein n and $R^{8b}$ is 3-OH | | 136-138 |

** See synthesis example for $^1$H NMR data.
*** Z is defined in Exhibit 2B.

INDEX TABLE B

| Compound | $R^1$ | $R^4$ | Q | Z (***) | AP+ (M + 1) | m.p. (° C.) |
|---|---|---|---|---|---|---|
| 5 (Ex. 1) | Cl | CH$_3$O | CH$_2$ | Z-6 wherein n and p are 0 | ** | |
| 6 | Cl | CH$_3$O | CH$_2$ | Z-2 wherein n and p are 0 | * | |
| 7 | Cl | CH$_3$O | CH$_2$ | Z-9 wherein n and p are 0 | * | |
| 8 (Ex. 2) | Cl | CH$_3$ | CH$_2$ | Z-6 wherein n and p are 0 | ** | |
| 9 (Ex. 3) | Cl | CH$_3$NH | CH$_2$ | Z-6 wherein n and p are 0 | ** | |
| 10 | F | CH$_3$O | CH$_2$ | Z-9 wherein n and p are 0 | | 124-126 |

INDEX TABLE B-continued

| Compound | $R^1$ | $R^4$ | Q | Z (***) | AP+ (M + 1) | m.p. (° C.) |
|---|---|---|---|---|---|---|
| 11 | F | $CH_3O$ | $CH_2$ | Z-6 wherein n and p are 0 | | 140-144 |
| 14 | F | $CH_3O$ | $CH_2$ | Z-31 wherein n and p are 0 and $R^{9a}$ is H | | 189-191 |
| 15 | F | $CH_3O$ | $CH_2$ | Z-15 wherein n and p are 0 and $R^{9a}$ is H | | 158-160 |
| 18 | F | $CH_3O$ | $CH_2$ | Z-28 wherein n and p are 0 | | 160-162 |
| 21 | F | $CH_3O$ | $CH_2$ | Z-15 wherein n and p are 0 and $R^{9a}$ is $CH_3$ | | |
| 22 | F | $CH_3O$ | $CH_2$ | Z-6 wherein n and $R^{8b}$ is 4-F | | 146-149 |
| 25 | $CH_3$ | $CH_3O$ | $CH_2$ | Z-6 wherein n and p are 0 | | 152-154 |
| 26 | $CH_3$ | $CH_3O$ | $CH_2$ | Z-9 wherein n and p are 0 | | 153-155 |

\* See Index TABLE C for $^1$H NMR data.
\*\* See synthesis example for $^1$H NMR data.
\*\*\* Z is defined in Exhibit 2B.

INDEX TABLE C

| Compd. No. | $^1$H NMR Data (CDCl$_3$ solution unless indicated otherwise)$^a$ |
|---|---|
| 6 | δ 3.6 (s, 3H), 4.32 (d, 2H), 6.1 (s, 2H), 7.02 (m. 2H), 7.45 (m, 2H), 7.56 (dd, 1H), 7.82 (m, 2H), 7.92 (m, 1H), 8.52 (d, 1H). |
| 7 | δ 3.6 (s, 3H), 4.24 (s, 4H), 4.34 (d, 2H), 6.92 (dd, 1H), 6.96 (d, 1H), 7.4 (m, 2H), 7.56 (dd, 1H), 7.8 (m, 2H), 7.9 (d, 1H), 8.5 (d, 1H). |
| 21 | δ 7.85 (d, 1H), 7.65 (m, 1H), 7.60 (m, 1H), 7.25 (m, 1H), 7.15 (m, 2H), 6.8 (d, 1H), 6.65 (s, 1H), 5.1 (bs, 1 H), 4.45 (m, 2H), 4.25 (m, 2H), 3.65 (s, 3H), 3.25 (s, 2H), 3 (s, 3H). |

$^{a1}$H NMR data are in ppm downfield from tetramethylsilane. Couplings are designated by (s)—singlet, (d)—doublet, (t)—triplet, (m)—multiplet, (dd)—doublet of doublets, (br s)—broad singlet.

Biological Examples of the Invention

General protocol for preparing test suspensions for Tests A-G: the test compounds were first dissolved in acetone in an amount equal to 11% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-G. Spraying a 200 ppm test suspension to the point of run-off on the test plants was the equivalent of a rate of 800 g/ha.

Test A

The test suspension was sprayed to the point of run-off on wheat seedlings. The following day the seedlings were inoculated with a spore dust of *Erysiphe graminis* f. sp. *tritici*, (the causal agent of wheat powdery mildew) and incubated in a growth chamber at 20° C. for 8 days, after which time disease ratings were visually made.

Test B

The test suspension was sprayed to the point of run-off on wheat seedlings. The following day the seedlings were inoculated with a spore suspension of *Puccinia recondita* f sp. *tritici* (the causal agent of wheat leaf rust) and incubated in a saturated atmosphere at 20° C. for 24 h, and then moved to a growth chamber at 20° C. for 7 days, after which time disease ratings were visually made.

Test C

Wheat seedlings were inoculated with a spore suspension of *Puccinia recondita* f. sp. *tritici* (the causal agent of wheat leaf rust) and incubated in a saturated atmosphere at 20° C. for 24 h. The following day, the test suspension was sprayed to the point of run-off on the wheat seedlings and then moved to a growth chamber at 20° C. for 5 days, after which time disease ratings were visually made.

Test D

The test suspension was sprayed to the point of run-off on wheat seedlings. The following day the seedlings were inoculated with a spore suspension of *Septoria nodorum* (the causal agent of wheat glume blotch) and incubated in a saturated atmosphere at 20° C. for 48 h, and then moved to a growth chamber at 20° C. for 7 days, after which time disease ratings were visually made.

Test E

The test suspension was sprayed to the point of run-off on wheat seedlings. The following day the seedlings were inoculated with a spore suspension of *Septoria tritici* (the causal agent of wheat leaf blotch) and incubated in a saturated atmosphere at 24° C. for 48 h, and then moved to a growth chamber at 20° C. for 19 days, after which time disease ratings were visually made.

Test F

The test suspension was sprayed to the point of run-off on tomato seedlings. The following day the seedlings were inoculated with a spore suspension of *Botrytis cinerea* (the causal agent of tomato *botrytis*) and incubated in saturated atmosphere at 20° C. for 48 h, and then moved to a growth chamber at 27° C. for 3 additional days, after which time disease ratings were visually made.

Test G

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 24° C. for 5 days, after which time disease ratings were visually made.

Results for Tests A-G are given in Table A. In the Table, a rating of 100 indicates 100% disease control and a rating of 0 indicates no disease control (relative to the controls). A dash (-) indicates no test results. All results are for 200 ppm except where followed by an "*", which indicates 40 ppm.

TABLE A

RESULTS OF BIOLOGICAL TESTS

| | Percentage Disease Control | | | | | | |
|---|---|---|---|---|---|---|---|
| Compound | Test A | Test B | Test C | Test D | Test E | Test F | Test G |
| 1 | 100 | 100 | — | 100 | 92 | 0 | 100 |
| 2 | 84 | 100 | 88 | 100 | 97* | 0 | 53 |
| 3 | 0 | 97 | 0 | 99 | 78 | 0 | 0 |
| 4 | 0 | 97 | 53 | 82 | 0 | 0 | 0 |
| 5 | 100 | 100 | 100 | 100 | 100 | 98 | 0 |
| 6 | 100 | 100 | 100 | 100 | 99 | 91 | 95 |
| 7 | 100 | 100 | 100 | 100 | 100 | 98 | 97 |
| 8 | 0 | 100 | 26 | 100 | 98 | 73 | 91 |
| 9 | 0 | 88 | 8 | 100 | 79 | 0 | 9 |
| 10 | 100 | 100 | 100 | 100 | 98 | 94 | 84 |
| 11 | 100 | 100 | 100 | 100 | 100 | 0 | 40 |
| 12 | 100 | 100 | 100 | 100 | 100 | 0 | 88 |
| 13 | 90 | 100 | 28 | 97 | 24 | 7 | 54 |
| 14 | 0 | 54 | 0 | 0 | 44 | 0 | 0 |
| 15 | 0 | 100 | 38 | 100 | 99 | 80 | 12 |
| 16 | 100 | 100 | 100 | 100 | 100 | 99 | 85 |
| 17 | 100 | 100 | 100 | 100 | 99 | 87 | 93 |
| 18 | 90 | 100 | 74 | 99 | 97 | 79 | 50 |
| 19 | 100 | 100 | 100 | 100 | 100 | 99 | 73 |
| 20 | 99 | 100 | 100 | 100 | 100 | 95 | 90 |
| 21 | 13 | 100 | 98 | 100 | 96 | 99 | 99 |
| 22 | 100 | 100 | 100 | 100 | 94 | 33 | 8 |
| 23 | 0 | 94 | 0 | 73 | 0 | 0 | 0 |
| 24 | 0 | 96 | 0 | 89 | 0 | 0 | 0 |
| 25 | 100 | 100 | 100 | 100 | 100 | 0 | 0 |
| 26 | 100 | 100 | 100 | 100 | 99 | 33 | 9 |
| 27 | 0 | 99 | 0 | 100 | 0 | 66 | 86 |
| 28 | 99 | 100 | 100 | 99 | 93 | 0 | 90 |
| 29 | 72 | 99 | 0 | 99 | 10 | 0 | 17 |
| 30 | 98 | 100 | 9 | 99 | 78 | 0 | 94 |

What is claimed is:

1. A compound selected from Formula 1, N-oxides, and salts thereof,

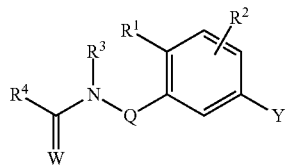

wherein
Y is

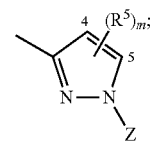

Z is an 10-membered fused heterobicyclic ring system containing ring members selected from carbon atoms and 1 to 4 heteroatoms independently selected from up to 2 O, up to 2 S and up to 4 N atoms, wherein up to 3 carbon atom ring members are independently selected from C(=O) and C(=S), and the sulfur atom ring members are independently selected from S(=O)$_u$(=NR$^7$)$_z$, the ring system optionally substituted with substituents independently selected from R$^8$ on carbon atom ring members and from R$^9$ on nitrogen atom ring members;

W is O;
Q is CR$^{10a}$R$^{10b}$;
R$^1$ is halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_6$ cycloalkyl;
R$^2$ is H, halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_6$ cycloalkyl;
R$^3$ is H, $C_1$-$C_3$ alkyl, $C_1$-$C_3$ haloalkyl, $C_3$-$C_4$ cycloalkyl, $C_3$-$C_4$ halocycloalkyl, $C_2$-$C_6$ alkylcarbonyl, $C_2$-$C_6$ haloalkylcarbonyl, $C_2$-$C_6$ alkoxycarbonyl or $C_2$-$C_6$ haloalkoxycarbonyl;
R$^4$ is H, $C_1$-$C_2$ alkyl, $C_1$-$C_2$ alkoxy, $C_1$-$C_2$ haloalkoxy, $C_1$-$C_2$ alkylamino or $C_2$-$C_4$ dialkylamino;
each R$^5$ is independently halogen, cyano, hydroxy, amino, nitro, $C_1$-$C_6$ alkyl, $C_3$-$C_5$ cycloalkyl, $C_3$-$C_5$ halocycloalkyl, $C_2$-$C_6$ alkenyl, $C_2$-$C_6$ alkynyl or $C_1$-$C_6$ haloalkyl;
m is 0, 1 or 2;
each R$^8$ is independently halogen, cyano, hydroxy, amino, nitro, —CH(=O), —C(=O)OH, —C(=O)NH$_2$, —C(R$^{12}$)=N—O—R$^{13}$, —C(R$^{12}$)=N—R$^{13}$, $C_1$-$C_4$ alkyl, $C_1$-$C_4$ haloalkyl, $C_3$-$C_4$ cycloalkyl, $C_2$-$C_4$ alkenyl, $C_2$-$C_4$ alkynyl, $C_2$-$C_5$ alkylcarbonyl, $C_2$-$C_5$ haloalkylcarbonyl, $C_4$-$C_5$ cycloalkylcarbonyl, $C_2$-$C_5$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_5$ cycloalkylaminocarbonyl, $C_1$-$C_4$ alkoxy, $C_1$-$C_4$ haloalkoxy, $C_3$-$C_4$ cycloalkoxy, $C_3$-$C_4$ halocycloalkoxy, $C_4$-$C_5$ cycloalkylalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_2$-$C_8$ alkylcarbonyloxy, $C_2$-$C_8$ halo alkylcarbonyloxy, $C_4$-$C_{10}$ cycloalkylcarbonyloxy, $C_1$-$C_4$ alkylthio, $C_1$-$C_4$ haloalkylthio, $C_3$-$C_6$ cycloalkylthio, $C_1$-$C_4$ alkylsulfinyl, $C_1$-$C_4$ haloalkylsulfinyl, $C_1$-$C_4$ alkylsulfonyl, $C_1$-$C_4$ haloalkylsulfonyl, $C_3$-$C_5$ cycloalkylsulfonyl, $C_3$-$C_7$ trialkylsilyl, $C_1$-$C_4$ alkylamino, $C_2$-$C_8$ dialkylamino, $C_1$-$C_4$ haloalkylamino, $C_2$-$C_8$ halodialkylamino, $C_3$-$C_6$ cycloalkylamino, $C_2$-$C_5$ alkylcarbonylamino or $C_2$-$C_5$ haloalkylcarbonylamino;
each R$^9$ is independently cyano, hydroxy, —CH(=O), —C(=O)NH$_2$, —C(R$^{12}$)=N—O—R$^{13}$, —C(R$^{12}$)=N—R$^{13}$, $C_1$-$C_4$ alkyl, $C_3$-$C_4$ cycloalkyl, $C_2$-$C_4$ alkenyl, $C_2$-$C_4$ alkynyl, $C_1$-$C_4$ haloalkyl, $C_2$-$C_5$ alkylcarbonyl, $C_2$-$C_5$ haloalkylcarbonyl, $C_4$-$C_5$ cycloalkylcarbonyl, $C_2$-$C_5$ alkoxycarbonyl, $C_4$-$C_{10}$ cycloalkoxycarbonyl, $C_2$-$C_8$ alkylaminocarbonyl, $C_3$-$C_{10}$ dialkylaminocarbonyl, $C_4$-$C_5$ cycloalkylaminocarbonyl, $C_1$-$C_4$ alkoxy, $C_1$-$C_4$ haloalkoxy, $C_3$-$C_4$ cycloalkoxy, $C_3$-$C_4$ halocycloalkoxy, $C_4$-$C_5$ cycloalkylalkoxy, $C_2$-$C_4$ alkenyloxy, $C_2$-$C_4$ haloalkenyloxy, $C_2$-$C_4$ alkynyloxy, $C_3$-$C_4$ haloalkynyloxy, $C_2$-$C_4$ alkoxyalkoxy, $C_2$-$C_8$ alkylcarbonyloxy, $C_2$-$C_8$ halo alkylcarbonyloxy, $C_4$-$C_{10}$ cycloalkylcarbonyloxy, $C_1$-$C_6$ alkylthio, benzylthio, $C_1$-$C_6$ haloalkylthio, $C_3$-$C_8$ cycloalkylthio, $C_1$-$C_4$ alkylsulfonyl, $C_1$-$C_4$ haloalkylsulfonyl, $C_3$-$C_6$ cycloalkylsulfonyl or $C_3$-$C_{10}$ trialkylsilyl;

each $R^7$ and $R^{13}$ is independently H, $C_1$-$C_3$ alkyl, $C_1$-$C_3$ haloalkyl, $C_2$-$C_3$ alkylcarbonyl or $C_2$-$C_3$ haloalkylcarbonyl;

$R^{10}$a is H, OH, halogen, cyano, $C_1$-$C_3$ alkyl, $C_1$-$C_3$ haloalkyl, $C_2$-$C_3$ alkoxyalkyl, $C_1$-$C_3$ alkoxy, $C_1$-$C_3$ haloalkoxy or $C_1$-$C_3$ alkylsulfonyl;

$R^{10b}$ is H, $C_1$-$C_3$ alkyl, $C_1$-$C_3$ haloalkyl, $C_2$-$C_3$ alkoxyalkyl, $C_1$-$C_3$ alkoxy or $C_1$-$C_3$ haloalkoxy; or $R^{10a}$ and $R^{10b}$ are taken together with the carbon atom to which they are attached to form a $C_3$-$C_4$ cycloalkyl or $C_3$-$C_4$ halocycloalkyl ring;

each $R^{12}$ is independently H, $C_1$-$C_3$ alkyl, $C_3$-$C_5$ cycloalkyl or $C_1$-$C_3$ haloalkyl; and u and z in each instance of $S(=O)_u(=NR^7)_z$ are independently 0, 1 or 2, provided that the sum of u and z in each instance of $S(=O)_u(=NR^7)_z$ is 0, 1 or 2.

2. A compound of claim 1 wherein
$R^1$ is halogen, CN, $C_1$-$C_3$ alkyl, $C_1$-$C_3$ alkoxy, $C_1$-$C_3$ haloalkyl, $C_1$-$C_3$ haloalkoxy or $C_3$-$C_4$ cycloalkyl;
$R^2$ is H, halogen, CN, $C_1$-$C_3$ alkyl, $C_1$-$C_3$ alkoxy or $C_1$-$C_3$ haloalkyl;
$R^3$ is H, $C_1$-$C_2$ alkyl, $C_1$-$C_2$ haloalkyl, $C_2$-$C_3$ alkylcarbonyl or $C_2$-$C_3$ haloalkylcarbonyl;
$R^4$ is H, $C_1$-$C_2$ alkyl, $C_1$-$C_2$ alkoxy or $C_1$-$C_2$ haloalkoxy;
each $R^5$ is independently halogen, cyano, $C_1$-$C_2$ alkyl or $C_1$-$C_2$ haloalkyl;
each $R^8$ is independently halogen, cyano, hydroxy, amino, —CH(=O), —C(=O)NH$_2$, $C_1$-$C_4$ alkyl, $C_1$-$C_4$ haloalkyl, $C_3$-$C_4$ cycloalkyl, $C_2$-$C_5$ alkylcarbonyl, $C_2$-$C_5$ haloalkylcarbonyl, $C_1$-$C_4$ alkoxy, $C_1$-$C_4$ haloalkoxy or $C_3$-$C_4$ cycloalkoxy;
each $R^9$ is independently cyano, hydroxy, —CH(=O), —C(=O)NH$_2$, $C_1$-$C_4$ alkyl, $C_1$-$C_4$ haloalkyl, $C_3$-$C_4$ cycloalkyl, $C_2$-$C_5$ alkylcarbonyl, $C_2$-$C_5$ haloalkylcarbonyl, $C_1$-$C_4$ alkoxy, $C_1$-$C_4$ haloalkoxy or $C_3$-$C_4$ cycloalkoxy;
$R^{10a}$ is H;
$R^{10b}$ is H or methyl; or
$R^{10a}$ and $R^{10b}$ are taken together with the carbon atom to which they are attached to form a cyclopropyl ring; and
wherein in the fused heterobicyclic ring system of Z the ring that is directly bonded to Y is aromatic and is identified as a first ring, the ring that is fused to the first ring is identified as a second ring, the second ring includes an O atom as a ring member directly bonded to a ring fusion atom shared with the first ring, and said ring fusion atom is connected through no less than one intervening ring member atom to the ring member atom directly bonded to Y.

3. A compound of claim 2 wherein
$R^1$ is halogen, CN, $C_1$-$C_2$ alkyl, $C_1$-$C_2$ alkoxy, $C_1$-$C_2$ haloalkyl or $C_1$-$C_2$ haloalkoxy;
$R^2$ is H, halogen, CN, methyl or trifluoromethyl;

$R^3$ is H or methyl;
each $R^5$ is independently halogen or methyl;
$R^{10a}$ is H;
$R^{10b}$ is H or methyl;
Z is

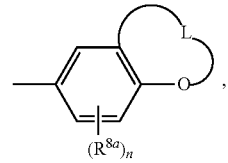

Z-A

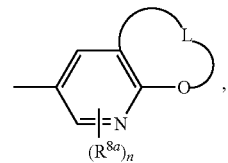

Z-B

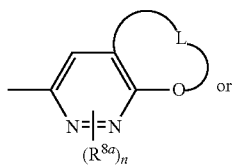

Z-C

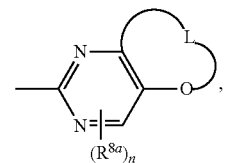

Z-D

L is a linking chain containing 3 chain members selected from carbon atoms and up to 1 heteroatoms independently selected from up to 1 O, up to 1 S and up to 1 N atoms, wherein up to 2 carbon atom ring members are independently selected from C(=O) and C(=S), and the sulfur atom ring members are independently selected from $S(=O)_u(=NR^7)_z$, the linking chain optionally substituted with up to 4 substituents independently selected from $R^{8b}$ on carbon atom ring members and from $R^9$ on nitrogen atom ring members;

each $R^{8a}$ and $R^{8b}$ is independently $R^8$;

$R^9$ is hydroxy, $C_1$-$C_2$ alkyl or $C_1$-$C_2$ alkoxy; and n is 0, 1 or 2.

4. A compound of claim 3 wherein
$R^1$ is halogen, CN, $C_1$-$C_2$ alkyl or $C_1$-$C_2$ haloalkyl;
$R^2$ is H or halogen;
$R^3$ is H;
$R^4$ is H, $C_1$-$C_2$ alkyl or methoxy;
each $R^{8a}$ is independently halogen, $C_1$-$C_2$ alkyl or $C_1$-$C_2$ alkoxy;

each $R^{8b}$ is independently F, Cl, $C_1$-$C_3$ alkyl or $C_2$-$C_3$ alkylcarbonyl;

$R^{10b}$ is H or methyl;

Z is

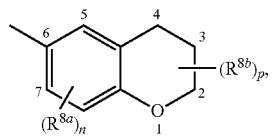
Z-6

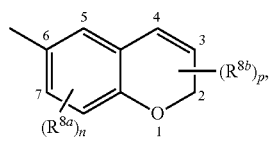
Z-7

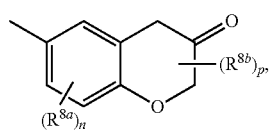
Z-8

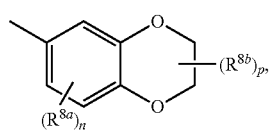
Z-9

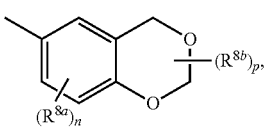
Z-10

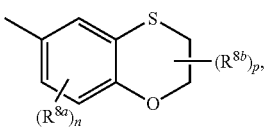
Z-11

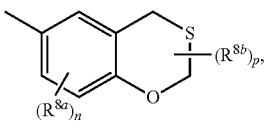
Z-12

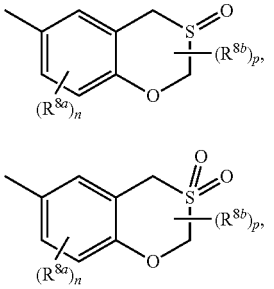
Z-13

Z-14

Z-15

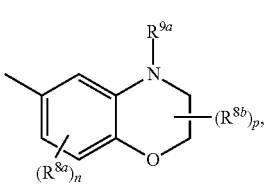

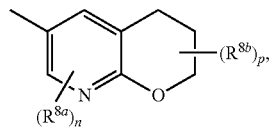
Z-23

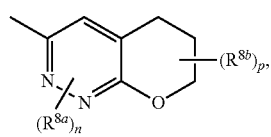
Z-24

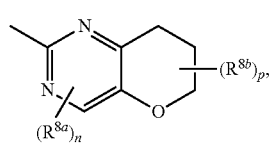
Z-25

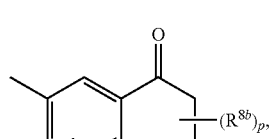
Z-28

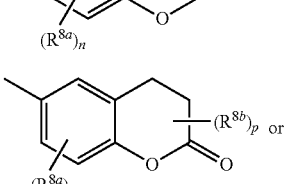
Z-29

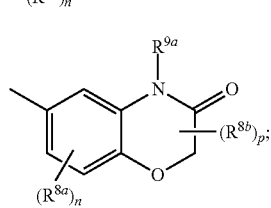
Z-31

$R^9a$ is H or $C_1$-$C_2$ alkyl;

m is 0;

n is 0, 1 or 2; and p is 0, 1 or 2.

5. A compound of claim 4 wherein $R^1$ is F, Cl, Br or methyl;

$R^2$ is H, F or Cl;

$R^4$ is H, methyl or methoxy;

each $R^{8a}$ is independently F, Cl, Br, methyl or methoxy;

each $R^{8b}$ is independently F or methyl;

$R^{10b}$ is H; and

Z is Z-6, Z-9 or Z-10.

6. The compound of claim 1 which is selected from the group:

methyl N-[[2-chloro-5-[1-(3,4-dihydro-2H-1-benzopyran-6-yl)-1H-pyrazol-3-yl]-phenyl]methyl]carbamate;

methyl N-[[5-[1-(3,4-dihydro-2H-1-benzopyran-6-yl)-1H-pyrazol-3-yl]-2-fluorophenyl]methyl]carbamate; and methyl N-[[5-[1-(3,4-dihydro-2H-1-benzopyran-6-yl)-1H-pyrazol-3-yl]-2-methylphenyl]methyl]carbamate.

7. A fungicidal composition comprising (a) a compound of claim 1; and (b) at least one other fungicide.

8. A fungicidal composition comprising (a) a compound of claim 1; and (b) at least one additional component selected from the group consisting of surfactants, solid diluents and liquid diluents.

9. A method for controlling plant diseases caused by fungal plant pathogens comprising applying to the plant or portion thereof, or to the plant seed, a fungicidally effective amount of a compound of claim 1, wherein Z is a 10-membered fused heterobicyclic ring system containing ring members selected from carbon atoms and 1 to 4 heteroatoms independently selected from up to 2 O and up to 4 N atoms, wherein up to 3 carbon atom ring members are independently selected from C(=O) and C(=S), the ring system optionally substituted with substituents independently selected from $R^9$ on carbon atom ring members and from $R^9$ on nitrogen atom ring members.

10. The fungicidal composition of claim 7 wherein component (b) comprises at least one compound selected from the group consisting of: azoxystrobin, kresoxim-methyl, trifloxystrobin, pyraclostrobin, picoxystrobin, dimoxystrobin, metominostrobin/fenominostrobin, carbendazim, chlorothalonil, quinoxyfen, metrafenone, cyflufenamid, fenpropidine, fenpropimorph, bromuconazole, cyproconazole, difenoconazole, epoxiconazole, fenbuconazole, flusilazole, hexaconazole, ipconazole, metconazole, penconazole, propiconazole, proquinazid, prothioconazole, tebuconazole, triticonazole, famoxadone, prochloraz, penthiopyrad and boscalid.

\* \* \* \* \*